(12) United States Patent
Ittah et al.

(10) Patent No.: US 12,030,919 B2
(45) Date of Patent: Jul. 9, 2024

(54) COMPOSITE MATERIALS COMPRISING SYNTHETIC DRAGLINE SPIDER SILK

(71) Applicant: SEEVIX MATERIAL SCIENCES LTD., Jerusalem (IL)

(72) Inventors: Shmulik Ittah, Mevaseret Zion (IL); Meni Shimel, Kiryat Ono (IL); Ella Sklan, Jerusalem (IL); Dganit Stern, Kibbutz Lavi (IL)

(73) Assignee: SEEVIX MATERIAL SCIENCES LTD., Jerusalem (IL)

( * ) Notice: Subject to any disclaimer, the term of this patent is extended or adjusted under 35 U.S.C. 154(b) by 0 days.

(21) Appl. No.: 17/827,920

(22) Filed: May 30, 2022

(65) Prior Publication Data
US 2023/0042322 A1     Feb. 9, 2023

Related U.S. Application Data

(63) Continuation of application No. 16/076,770, filed as application No. PCT/IL2017/050175 on Feb. 12, 2017, now Pat. No. 11,345,727.
(Continued)

(30) Foreign Application Priority Data

Aug. 10, 2016   (WO) .................. PCT/IL2016/050874

(51) Int. Cl.
*C07K 14/435*     (2006.01)
*C12N 5/00*       (2006.01)
(Continued)

(52) U.S. Cl.
CPC ...... *C07K 14/43518* (2013.01); *C12N 5/0068* (2013.01); *C12N 5/0602* (2013.01);
(Continued)

(58) Field of Classification Search
CPC ........ C07K 14/43518; C07K 14/43586; D01F 4/02; D10B 2211/04; A61L 27/227
See application file for complete search history.

(56) References Cited

U.S. PATENT DOCUMENTS 3,755,560 A    8/1973  Dickert et al.
4,421,769 A   12/1983  Dixon et al.
(Continued)

FOREIGN PATENT DOCUMENTS

CA    3014537 A1    8/2017
CN   101133080 A    2/2008
(Continued)

OTHER PUBLICATIONS

Stothard, P. Protein Molecular Weight. Protein molecular weight. https://www.bioinformatics.org/sms/prot_mw.html (Year: 2022).*
(Continued)

*Primary Examiner* — Marla D Mcconnell
*Assistant Examiner* — Christine X Nisula
(74) *Attorney, Agent, or Firm* — The Roy Gross Law Firm, LLC; Roy Gross

(57) ABSTRACT

Composites based on a polymer and a mixture of proteins derived from a MaSp (major ampullate spidroin) protein are provides. Further, methods for preparation of same, and method of use of the composites are provided.

4 Claims, 62 Drawing Sheets

Specification includes a Sequence Listing.

Related U.S. Application Data

(60) Provisional application No. 62/317,572, filed on Apr. 3, 2016, provisional application No. 62/293,880, filed on Feb. 11, 2016.

(51) Int. Cl.

| | |
|---|---|
| *C12N 5/071* | (2010.01) |
| *D01D 5/00* | (2006.01) |
| *D01F 1/10* | (2006.01) |
| *D01F 4/00* | (2006.01) |
| *D01F 4/02* | (2006.01) |
| *D01F 6/88* | (2006.01) |

(52) U.S. Cl.
CPC ............. *D01D 5/0038* (2013.01); *D01F 1/10* (2013.01); *D01F 4/00* (2013.01); *D01F 4/02* (2013.01); *D01F 6/88* (2013.01); *C12N 2533/30* (2013.01); *C12N 2533/50* (2013.01); *D10B 2211/01* (2013.01); *D10B 2211/04* (2013.01); *D10B 2331/00* (2013.01); *D10B 2331/02* (2013.01); *D10B 2331/041* (2013.01); *D10B 2331/10* (2013.01); *D10B 2401/061* (2013.01); *D10B 2401/063* (2013.01)

(56) References Cited

U.S. PATENT DOCUMENTS

| | | | |
|---|---|---|---|
| 5,011,681 | A | 4/1991 | Ciotti et al. |
| 7,057,023 | B2 | 6/2006 | Islam et al. |
| 7,521,228 | B2 | 4/2009 | Lewis et al. |
| 7,674,882 | B2 | 3/2010 | Kaplan et al. |
| 7,754,851 | B2 | 7/2010 | Scheibel et al. |
| 8,030,024 | B2 | 10/2011 | Scheibel et al. |
| 8,222,479 | B2 | 7/2012 | Zhao et al. |
| 8,461,301 | B2 | 6/2013 | Gat et al. |
| 9,233,067 | B2 | 1/2016 | Lammel et al. |
| 9,475,852 | B2 | 10/2016 | Bogush et al. |
| 9,993,525 | B2 | 6/2018 | Nazhat et al. |
| 11,142,553 | B2 | 10/2021 | Taniike et al. |
| 11,376,329 | B2 | 7/2022 | Kluge et al. |
| 2005/0054830 | A1 | 3/2005 | Islam et al. |
| 2007/0196429 | A1 | 8/2007 | Scheibel et al. |
| 2010/0143487 | A1 | 6/2010 | Masters |
| 2010/0317587 | A1 | 12/2010 | Chung et al. |
| 2011/0020409 | A1 | 1/2011 | Altman et al. |
| 2011/0189292 | A1 | 8/2011 | Lebreton et al. |
| 2012/0022005 | A1 | 1/2012 | Gat et al. |
| 2015/0056256 | A1 | 2/2015 | Essaidi |
| 2015/0087046 | A1 | 3/2015 | Hedhammar |
| 2015/0165092 | A1 | 6/2015 | Kaplan et al. |
| 2015/0284565 | A1 | 10/2015 | Scheibel et al. |
| 2016/0046679 | A1 | 2/2016 | Kluge et al. |
| 2016/0298265 | A1 | 10/2016 | Lewis et al. |
| 2019/0002510 | A1 | 1/2019 | Ittah et al. |
| 2020/0270316 | A1 | 8/2020 | Römer et al. |
| 2021/0101946 | A1 | 4/2021 | Lo et al. |
| 2021/0138071 | A1 | 5/2021 | Santos et al. |
| 2022/0127768 | A1 | 4/2022 | Yoshioka et al. |
| 2022/0177530 | A1 | 6/2022 | Altman |
| 2022/0235099 | A1 | 7/2022 | Kamikubo et al. |
| 2023/0042322 | A1 | 2/2023 | Ittah et al. |

FOREIGN PATENT DOCUMENTS

| | | |
|---|---|---|
| CN | 101395178 A | 3/2009 |
| CN | 102475909 A | 5/2012 |
| CN | 101253193 B | 11/2012 |
| CN | 101018806 B | 5/2014 |
| CN | 107595661 B | 1/2018 |
| CN | 111214385 A | 6/2020 |
| EP | 1558444 B1 | 8/2005 |
| EP | 1609801 A1 | 12/2005 |
| EP | 1773875 B1 | 9/2014 |
| JP | 2002369878 B2 | 12/2002 |
| JP | 2008507260 A | 3/2008 |
| JP | 2015532690 A | 11/2015 |
| JP | 2019510541 A | 4/2019 |
| JP | 2021054819 A | 4/2021 |
| JP | 2021155361 A | 10/2021 |
| WO | 2004090205 A2 | 10/2004 |
| WO | 2006002827 A1 | 1/2006 |
| WO | 2006002843 A1 | 1/2006 |
| WO | 2006002853 A1 | 1/2006 |
| WO | 2006008163 A2 | 1/2006 |
| WO | 2007025719 A1 | 3/2007 |
| WO | 2007078239 A3 | 12/2007 |
| WO | 2011063990 A2 | 6/2011 |
| WO | 2011069643 A2 | 6/2011 |
| WO | 2011113592 A1 | 9/2011 |
| WO | 2012175153 A2 | 12/2012 |
| WO | 2013071107 A1 | 5/2013 |
| WO | 2014037453 A1 | 3/2014 |
| WO | 2016038387 A1 | 3/2016 |
| WO | 2016057851 A1 | 4/2016 |
| WO | 2017025964 A1 | 2/2017 |
| WO | 2017138002 A1 | 8/2017 |
| WO | 2019067737 A1 | 4/2019 |
| WO | 2020183465 A1 | 9/2020 |
| WO | 2021001840 A1 | 1/2021 |
| WO | 2021011431 A1 | 1/2021 |
| WO | 2021121647 A1 | 6/2021 |
| WO | 2022020212 A2 | 1/2022 |

OTHER PUBLICATIONS

Yang, Yan-Xiang & Qian, Zhi-Gang & Zhong, Jian-Jiang & Xia, Xiao-Xia. (2016). Hyper-production of large proteins of spider dragline silk MaSp2 by *Escherichia coli* via synthetic biology approach. Process Biochemistry. 51. 10.1016/j.procbio.2016.01.006.

Murphy AR, Kaplan DL. Biomedical applications of chemically-modified silk fibroin. J Mater Chem. Jun. 23, 2009;19(36):6443-6450. doi: 10.1039/b905802h. PMID: 20161439; PMCID: PMC2790051.

Hardy JG, Bertin A, Torres-Rendon JG, Leal-Egana A, Humenik M, Bauer F, Walther A, Cölfen H, Schlaad H, Scheibel TR. Facile Photochemical Modification of Silk Protein-Based Biomaterials. Macromol Biosci. Nov. 2018;18(11):e1800216. doi: 10.1002/mabi.201800216. Epub Sep. 19, 2018. PMID: 30230222.

B. Liebmann, D. Hümmerich, T. Scheibel, M. Fehr, Formulation of poorly water-soluble substances using self-assembling spider silk protein, Colloids and Surfaces A: Physicochemical and Engineering Aspects, vol. 331, Issues 1-2, 2008, pp. 126-132, ISSN 0927-7757, https://doi.org/10.1016/j.colsurfa.2008.04.005.

Chen, J., Venkatesan, H. and Hu, J. (2018), Chemically Modified Silk Proteins. Adv. Eng. Mater., 20: 1700961. https://doi.org/10.1002/adem.201700961.

Doblhofer E, Heidebrecht A, Scheibel T. To spin or not to spin: spider silk fibers and more. Appl Microbiol Biotechnol. Nov. 2015;99(22):9361-80. doi: 10.1007/s00253-015-6948-8. Epub Sep. 11, 2015. PMID: 26362683.

An, B. et al; "Physical and biological regulation of neuron regenerative growth and network formation on recombinant dragline silks", Biomaterials, vol. 48, pp. 137-146. Feb. 11, 2015. DOI: 10.1016/j.biomaterials.2015.01.044.

Knight, E. et al; "Advances in 3D cell culture technologies enabling tissue-like structures to be created in vitro", Journal of Anatomy, vol. 227, No. 6, pp. 746-756. Nov. 20, 2014. DOI: 10.1111/joa.12257.

Ewicka, M. et al; "Recombinant spider silk matrices for neural stem cell cultures", Biomaterials, vol. 33, No. 31, pp. 7712-7717, Aug. 3, 2012. https://doi.org/10.1016/j.biomaterials.2012.07.021.

Ittah, S. et al; "A proposed model for dragline spider silk self-assembley: Insights from the effect of the repetitive domain size on fiber properties"; Biopolymers, vol. 93, No. 5, pp. 458-468, 2010. DOI: 10.1002/bip.21362.

(56) References Cited

OTHER PUBLICATIONS

Ittah, S. et al; "A model for the structure of the C-terminal domain of dragline spider silk and the role of its conserved cysteine"; Biomacromolecules, vol. 8, No. 9, pp. 2768-2773, 2007. DOI: 10.1021/bm7004559.

Ittah, S. et al; "An Essential Role for the C-Terminal Domain of A Dragline Spider Silk Protein in Directing Fiber Formation"; Biomacromolecules, vol. 7, No. 6, pp. 1790-1795, 2006. DOI: 10.1021/bm060120k.

Huemmerich, D. et al; "Novel assembly properties of recombinant spider dragline silk proteins"; Current Biology, vol. 14, pp. 2070-2074, 2004. DOI: 10.1016/j.cub.2004.11.005.

Rising, A. et al; "Spider silk proteins: recent advances in recombinant production, structure-function relationships and biomedical applications"; Cell Mol Life Sci. Jan. 2011;68(2):169-84. DOI: 10.1007/s00018-010-0462-z.

https://www.bioinformatics.org/sms/prot_mw.html, The Sequence Manipulation Suite: Protein Molecular Weight, accessed on Dec. 2, 2019.

Gatesy, J. et al., "Extreme Diversity, Conservation, and Convergence of Spider Silk Fibroin Sequences" Science vol. 291, pp. 2603-2605, Mar. 30, 2001; DOI: 10.1126/science.1057561.

Sequence—Reference Material 1—Cited in a Third Party Observation in Japan, Oct. 2021.

Sequence—Reference Material 2—Cited in a Third Party Observation in Japan, Oct. 2021.

Sequence—Reference Material 3—Cited in a Third Party Observation in Japan, Oct. 2021.

PCT International Search Report for International Application No. PCT/IL2016/050874, dated Nov. 14, 2016, 4pp.

PCT Written Opinion for International Application No. PCT/IL2016/050874, dated Nov. 14, 2016, 4pp.

PCT International Search Report for International Application No. PCT/IL2017/050175, dated Mar. 29, 2017, 5 pp.

PCT Written Opinion for International Application No. PCT/IL2017/050175, dated Mar. 29, 2017, 6pp.

Lammel A .et al "Recombinant spider silk particles as drug delivery vehicles," Biomaterials, vol. 32, Issue 8, 2011, pp. 2233-2240, ISSN 0142-9612 https://doi.org/10.1016/j.biomaterials.2010.11.060.

Lammel A et al, "Controlling silk fibroin particle features for drug delivery," Biomaterials, vol. 31, Issue 16, 2010, pp. 4583-4591, ISSN 0142-9612 https://doi.org/10.1016/j.biomaterials.2010.02.024.

Huemmerich D et al, "Primary Structure Elements of Spider Dragline Silks and Their Contribution to Protein Solubility." Biochemistry 2004, 43, 42, 13604-13612, Publication Date:Sep. 29, 2004 https://doi.org/10.1021/bi048983q.

Ayoub et al., "Blueprint for a High-Performance Biomaterial: Full-Length Spider Dragline Silk Genes." PLoS One 2(6):, Jun. (2007), e514 , https://doi.org/10.1371/journal.pone.0000514—p. 13.

Scheibel, "Spider silks: recombinant synthesis, assembly, spinning, and engineering of synthetic proteins." Microb Cell Fact 3, 14 (2004). https://doi.org/10.1186/1475-2859-3-14—p. 10.

Huemmerich D, Helsen CW, Quedzuweit S, Oschmann J, Rudolph R, Scheibel T. Primary structure elements of spider dragline silks and their contribution to protein solubility. Biochemistry. Oct. 26, 2004;43(42): 13604-12. doi: 10.1021/bi048983q. PMID: 15491167.

Galarneau A, Mehlhorn D, Guenneau F, Coasne B, Villemot F, Minoux D, Aquino C, Dath JP. Specific Surface Area Determination for Microporous/Mesoporous Materials: The Case of Mesoporous FAU-Y Zeolites. Langmuir. Nov. 27, 2018;34(47): 14134-14142. doi: 10.1021/acs.langmuir.8b02144. Epub Nov. 14, 2018. PMID: 30379547.

\* cited by examiner

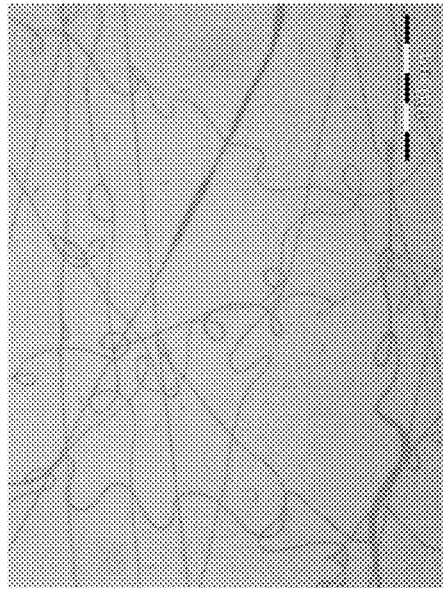
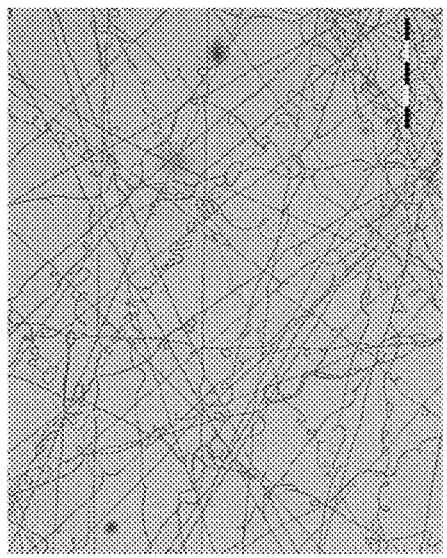
FIG. 11

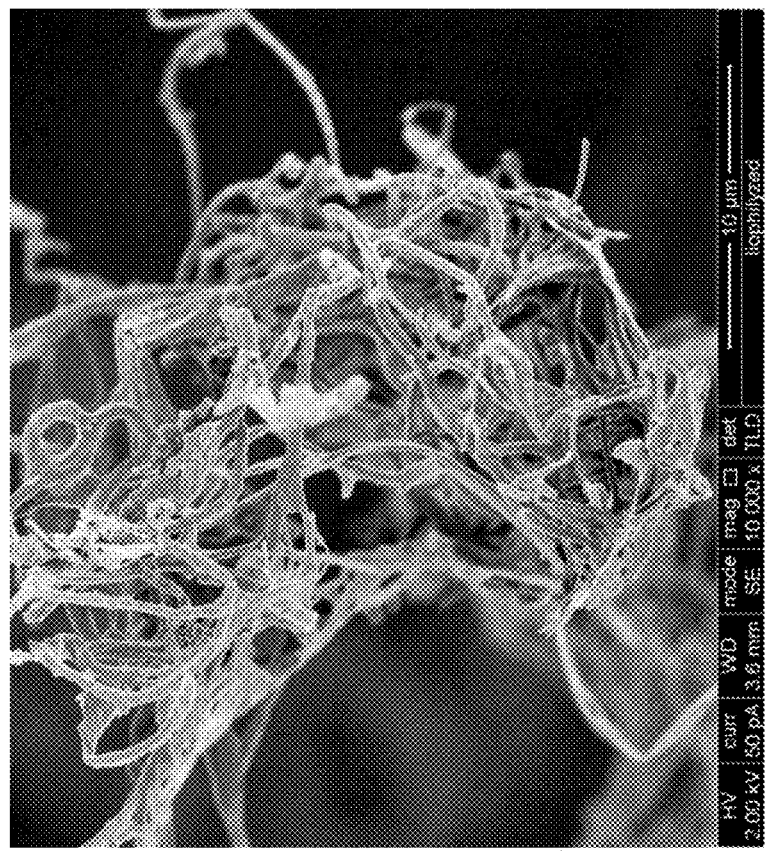
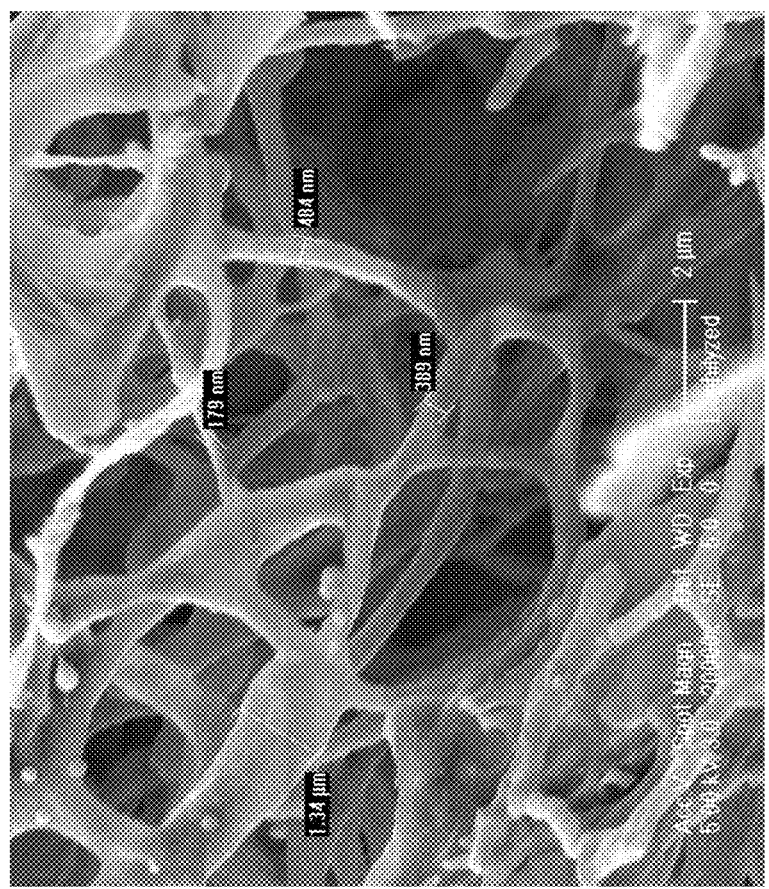
FIG. 28

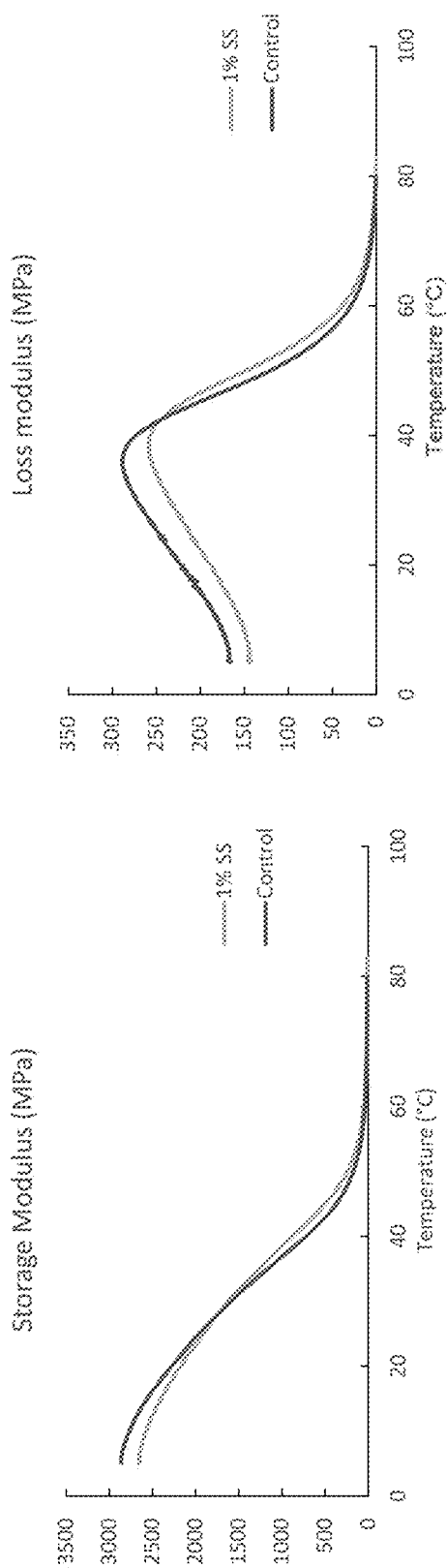

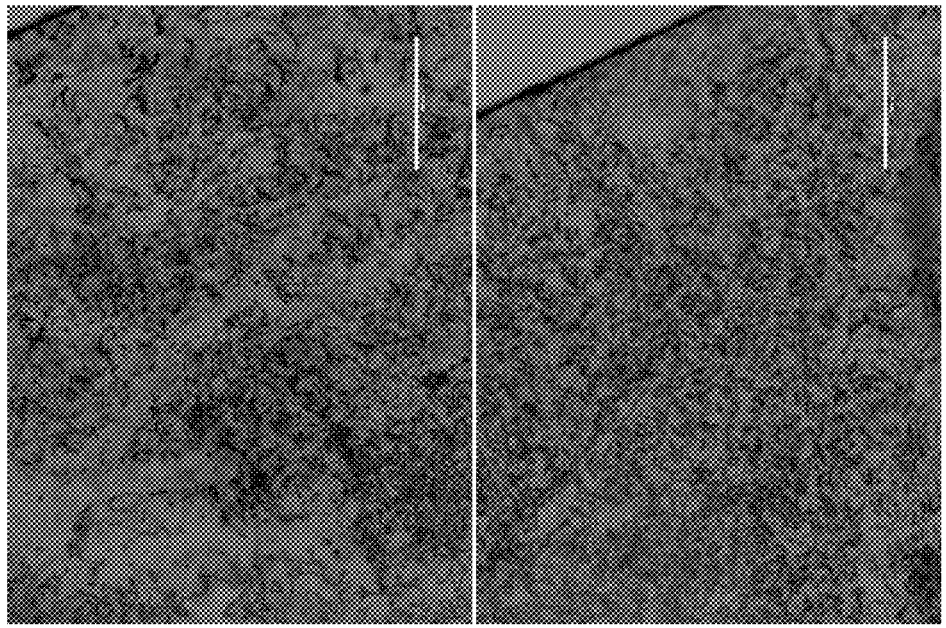
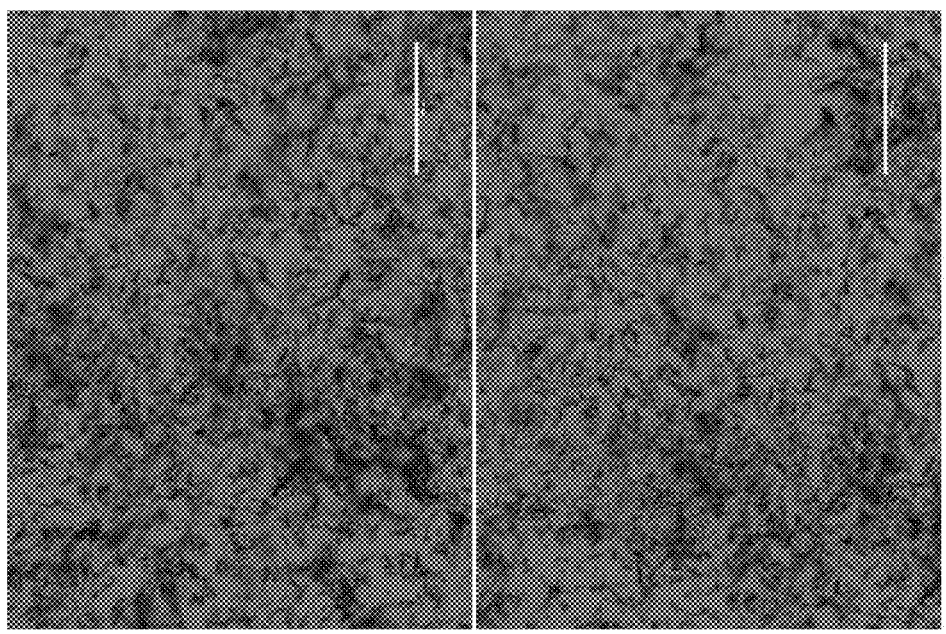
FIG. 34

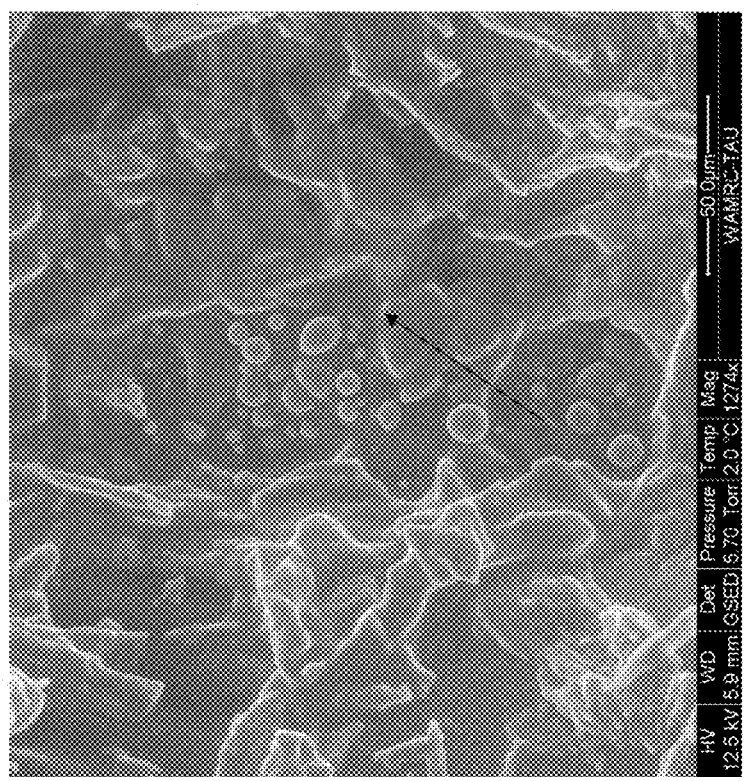
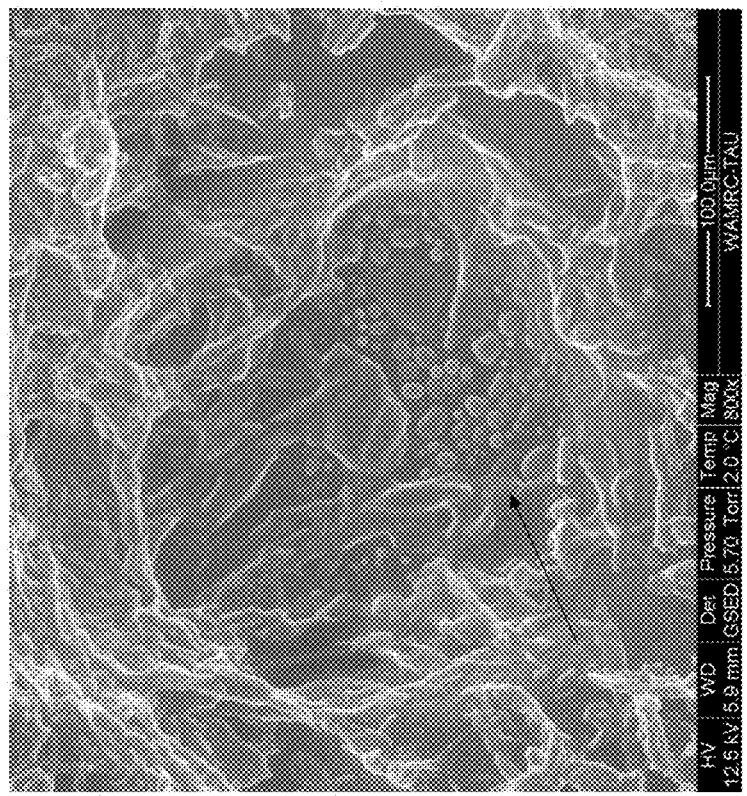
FIG. 37

COMPOSITE MATERIALS COMPRISING SYNTHETIC DRAGLINE SPIDER SILK

CROSS REFERENCE TO RELATED APPLICATIONS

This application is a continuation of U.S. patent application Ser. No. 16/076,770 filed Aug. 9, 2018, which is a National Phase of PCT Patent Application No. PCT/IL2017/050175 having International filing date of Feb. 12, 2017, which claims the benefit of priority of U.S. Provisional Patent Application No. 62/317,572, filed Apr. 3, 2016, U.S. Provisional Patent Application No. 62/293,880, filed Feb. 11, 2016, and PCT Patent Application No. PCT/IL2016/050874 filed on Aug. 10, 2016, all of which are herby incorporated by reference in their entirety.

This application incorporates by reference the sequence listing which is submitted together with this application in computer readable form which has the file name 06939-P0001C-SVX-P-002-US1_Corrected-SQL_ST25.txt, created on Jun. 20, 2022 and is 16 KB.

FIELD OF INVENTION

The present invention, in some embodiments thereof, is directed to composite materials based on proteins derived from a MaSp (major ampullate spidroin) protein, and the preparation of same.

BACKGROUND OF THE INVENTION

Dragline spider silk is known in the art as the silk used by the orb-web weaving spiders to construct the frame and radii of their webs as well a life line when they fall or escape danger. To be able to perform these tasks, the dragline fiber displays a remarkably high toughness due to combination of high elasticity and strength, which places it as the toughest fiber, whether natural or man-made. For instance, dragline is six times as strong as high-tensile steel in its diameter and three times tougher than Kevlar that is one of the strongest synthetic fibers ever made.

Dragline silk consists of two main polypeptides, mostly referred to as major ampullate spidroin (MaSp) 1 and 2, and also to ADF-3 and ADF-4 in *Araneus diadematus*. These proteins have apparent molecular masses in the range of 200-720 kDa, depending on sample age and conditions of analysis. The known dragline silk spidroins are composed of highly iterated blocks of alternating alanine-rich segments, forming crystalline β-sheets in the fiber, and glycine-rich segments which are more flexible and mainly lack ordered structure. The C-terminal region is non-repetitive, highly conserved between species, and adopts α-helical conformation. The N-terminal region of dragline silk proteins was also found to be highly conserved between different spidroins, and also between different spider species.

Numerous attempts have been made to synthetically create spider silk, such as through genetic engineering using bacteria, yeast, plants and mammalian cells in tissue culture and even transgenic goats.

U.S. Pat. No. 8,461,301 relates to, inter alia, isolated amino acid sequence comprising multiple repeats of a semi-synthetic spider silk protein domain, or any functional homolog, variant, derivative, fragment or mutant thereof. This publication is incorporated herein by reference in its entirety.

Additional publications relating to dragline spider silk include Ittah, S., et al. Biopolymers, 93 (5), 458-468, 2010; Ittah, S., et al. Biomacromolecules, 8 (9), 2768-2773, 2007; Ittah, S., et al., Biomacromolecules, 7 (6), 1790-1795, 2006; and Huemmerich, D., Ittah, S., et al., Current Biology, 14, 2070-2074, 2004. These publications are incorporated herein by reference in their entirety.

Various applications have been proposed for using composite materials based on spider silk, including for the coating of stents and implants, textile as well as ballistics applications.

There is an unmet need for improved compositions and methods for producing fibers with mechanical properties similar to the natural spider silk.

SUMMARY OF THE INVENTION

The present invention is directed to, inter alia, composite materials based on proteins derived from a MaSp (major ampullate spidroin) protein, and the preparation of same.

According to some aspects, there is provided a composite comprising a mixture of proteins and at least one polymer, wherein: the mixture of proteins comprises "m" types of proteins of differing molecular weight, wherein each protein in the mixture comprises, independently, "n" repeats of a repetitive region of a major ampullate spidroin (MaSp) protein, or a functional homolog, variant, derivative or fragment thereof, wherein m and n are, independently, an integer between 2 to 70.

In some embodiments, the mixture of proteins is characterized by one or more properties selected from the group consisting of:

(a) each repeat has a molecular weight in the range of 2 kDa to 3.5 kDa;

(b) the ratio of 'n' to 'm' is in the range of 2:1 to 1:2.

In some embodiments, the mixture of proteins is in the form of a fiber. In some embodiments, the fiber is attached to the polymer via a linker. In some embodiments, the mixture of proteins is attached to at least one surface of the polymer.

In some embodiments, the ratio of 'n' to 'm' is in the range of 2:1 to 1:2. In some embodiments, the ratio of 'n' to 'm' is in the range of 1.8:1 to 1:1.8. In some embodiments, the ratio of 'n' to 'm' is in the range of 1.6:1 to 1:1.6. In some embodiments, the ratio of 'n' to 'm' is in the range of 1.5:1 to 1:1.5. In some embodiments, the ratio of 'n' to 'm' is in the range of 1.3:1 to 1:1.3. In some embodiments, the ratio of 'n' to 'm' is in the range of 1.2:1 to 1:1.2. In some embodiments, the ratio of 'n' to 'm' is in the range of 1.1:1 to 1:1.1. In some embodiments, at least one polymer is a non MaSp protein derived polymer.

In some embodiments, each of the proteins comprise, independently, an amino acid sequence as set forth in SEQ ID NO: 1

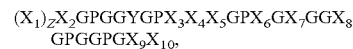

$(X_1)_Z X_2 GPGGYGPX_3 X_4 X_5 GPX_6 GX_7 GGX_8 GPGGPGX_9 X_{10}$, wherein $X_1$ is, independently, at each instance A or G wherein at least 50% of $(X_1)_Z$ is A, Z is an integer between 5 to 30; $X_2$ is S or G; $X_3$ is G or E; $X_4$ is G, S or N; $X_5$ is Q or Y; $X_6$ is G or S; $X_7$ is P or R; $X_8$ is Y or Q; $X_9$ is G or S; and $X_{10}$ is S or G.

In some embodiments, the repetitive region comprises the amino acid sequence as set forth in SEQ ID NO: 3 (AAAAAAAASGPGGYGPGSQGPSGPGGYGPGGP-GSS).

In some embodiments, the composite is characterized by at least one improved mechanical property as compared to the property for the polymer free of the mixture of proteins. In some embodiments, the property is selected from the group consisting of: Young's modulus, tensile strength, fracture strain, yield point, toughness, work to failure, impact, tear strength, flexural modulus, flexural strain and stress at elongation.

In some embodiments, the at least one property selected from Young's modulus, tensile strength, yield point, and stress at elongation, is enhanced by at least 5%. In some embodiments, the Young's modulus is enhanced by at least 200%. In some embodiments, the tensile strength is enhanced by at least 40%. In some embodiments, the yield point is enhanced by at least 40%.

In some embodiments, the composite is characterized by a structural strength, wherein more than 10% of the structural strength results from the mixture of proteins.

In some embodiments, the composite is characterized by a tensile strength, wherein more than 10% of the tensile strength results from the mixture of proteins.

In some embodiments, the polymer is a synthetic polymer. In some embodiments, the polymer is a thermoplastic polymer. In some embodiments, the polymer is a thermoset. In some embodiments, the polymer is an epoxy. In some embodiments, the polymer is polyester. In some embodiments, the polymer is selected from the group consisting of polyamides, polyurethane, Nylon, and polyacrylate, polycarbonate, and silicon. In some embodiments, the polymer is a cross-linked polymer. In some embodiments, the polymer is copolymer. In some embodiments, the polymer is in the form of a hydrogel.

In some embodiments, the polymer is selected from the group consisting of liquid crystal polymers, maleic anhydride grafted polypropylene, polyamides, Nylon 4,6, Nylon 6, Nylon 6,6, Nylon 11, Nylon 12, poly(arylamide), polyethylene, polybutylene terephthalate, polyethylene terephthalate, polyphenylene sulfide, polyphthalamide, polypropylene, poly(vinylidene fluoride), Poly(2-hydroxyethyl methacrylate) (pHEMA), polyurethane, polyvinyl butyral, ethylene vinyl alcohol copolymer, polylactide acid (PLA), polycaprolactone (PCL), xanthan, cellulose, collagen, elastin, keratin, cotton, rubber, cellulose, wool and any combination or mixture thereof.

In some embodiments, the polymer is selected from the group consisting of adhesive and cohesive materials. In some embodiments, the adhesive and cohesive materials are selected from the group consisting of epoxy, cyanoacrylates, polyesters, polyols, polyurethanes, and polyimides.

In some embodiments, a total concentration of the proteins ranges from about 0.1 weight percent to about 10 weight percent of the total weight of the composite. In some embodiments, the concentration ranges from about 0.5 weight percent to about 3 weight percent.

In some embodiments, the mixture of proteins and the polymer are substantially in a contiguous contact.

In some embodiments, the disclosed composite has a layer of at least 0.5 micron thick.

According to some aspects, there is provided a fiber comprising a mixture of proteins, wherein the mixture of proteins comprises "m" types of proteins of differing molecular weight, wherein each protein in the mixture comprises, independently, "n" repeats of a repetitive region of a major ampullate spidroin (MaSp) protein, or a functional homolog, variant, derivative or fragment thereof, wherein m and n are, independently, an integer between 2 to 70, and wherein the fiber is attached to at least one linker.

In one embodiment, "m" types of proteins or a mixture of proteins are in the form of a fiber as described herein. In one embodiment, "m" types of proteins or a mixture of proteins are inter-molecularly bound. In one embodiment, "m" types of proteins or a mixture of proteins are inter-molecularly bound in the form of a fiber as described herein. In one embodiment, inter-molecularly bound is non-covalent bound. In one embodiment, inter-molecularly bound is via Van-der-Waals bond, ionic bond, electrostatic bond, hydrogen bond, or any combination thereof. In one embodiment, "mixture of proteins" comprises or consists "m" types of proteins and/or a fiber. In one embodiment, "m" types of proteins is "m" types of peptides or m" types of polypeptides or m" types of a mixture of polypeptides and peptides.

In some embodiments, a plurality of the fiber is attached to one another via the linker.

According to some aspects, there is provided an article comprising the disclosed composite. In some embodiments, the article is stable in a physiological condition. In some embodiments, the article is a medical device. In some embodiments, the medical device is an implantable medical device. In some embodiments, the implantable medical device is selected from an artificial vascular graft, an artificial heart pump diaphragm, a tissue scaffold, an orthopedic implant, a catheter and a stent.

In some embodiments, the article is selected from the group consisting of: a pill, a tablet, a capsule, and a gel-cap. In some embodiments, the article comprises a fabric.

In some embodiments, the article is characterized by one or more properties selected from thermal insulation, thermal conductivity, electrical insulation, optical conductivity and refraction.

According to some aspects, there is provided a process of making the comprising a mixture of proteins and at least one polymer, wherein: the mixture of proteins comprises "m" types of proteins of differing molecular weight, wherein each protein in the mixture comprises, independently, "n" repeats of a repetitive region of a major ampullate spidroin (MaSp) protein, or a functional homolog, variant, derivative or fragment thereof, wherein m and n are, independently, an integer between 2 to 70, the process comprising the step of attaching the mixture of proteins to the polymer so as to form the composite.

In some embodiments, the process comprises a step of melting the polymer to yield a molten polymer and transforming the mixture of proteins into the molten polymer.

In some embodiments, the process comprises a step of dissolving the polymer to yield a dissolved polymer and transforming the mixture of proteins into the molten polymer.

In some embodiments, the process comprises a step of extruding the polymer.

In some embodiments, the process comprises forming one or more layers of the proteins by continuous electrospinning.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 9A-B refer to nylon 12 wires after extrusion). FIG. 9B presents representative SEM images of protein fibers in Nylon 12 at 2% enrichment. FIGS. 9C-E present Young's modulus (FIG. 9C), yield point (FIG. 9D), and stress-strain curves of 2% enrichment (upper graph) (FIG. 9E) of dogbones of injection molded nylon 12. FIG. 9F shows improvement of stress-strain graph (upper curve at strain=1) for the 2% SS enriched polylactic acid (PLA) sample.

FIG. 11 presents images of electrospun fibers ~10.5% (w/w) TPU+~2% (w/w) fillers (SS) (bar: in left panel—200 μm; in right panel—100 μm).

FIG. 28 presents SEM images showing SS lyophilized fibers. Scale bar in μm, from left to right: 2 and 10. Numbers in left figure indicate diameter size (179 nm to 1.34 μm)

FIGS. 29A-C present graphs showing a dynamic mechanical analysis (DMA) of VeroClear enrichment. The enhancement is seen as right shift in Tan delta peak. FIG. 29A shows storage modulus. FIG. 29B shows Loss modulus FIG. 29B presents Tan delta tests.

FIG. 34 presents microscopic images of the coated silicon (organic phase on the left, aqueous phase on the right).

FIG. 37 presents ESEM images showing droplets formed around the fibers but not on the fibers. Arrow on left image displays droplets on the substrate which are not seen on the fiber surface. Arrow on right image shows the rise of water level immersing the fiber surface with no droplets formed on the surface.

FIG. 46A shows that Live:dead cell ratio is 75% higher in SS spheroids; FIG. 46B shows that the volume of SS-containing spheroids is 3.5-4.8-times larger than that of control spheroids. FIG. 46C shows that the volume of live area in SS-containing spheroids is 4.7-times larger than that of control spheroids. In each triplet of bars, from left to right: control (untreated), collagen, and SS.

DETAILED DESCRIPTION OF THE INVENTION

Figure 1:
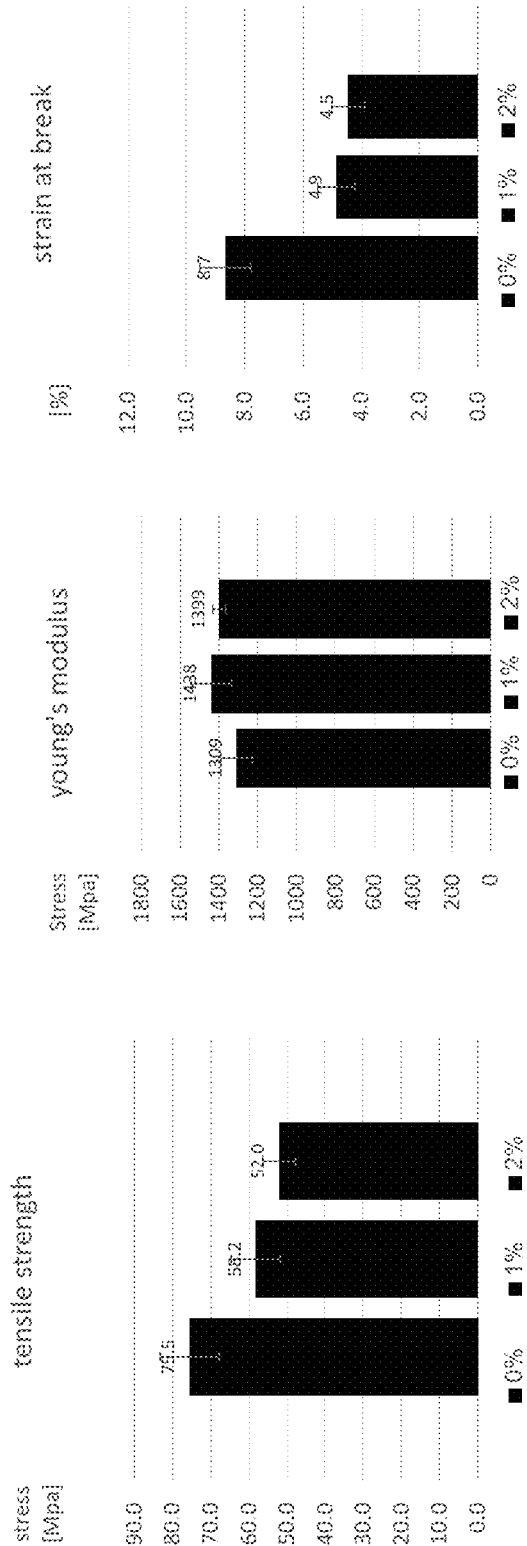
FIG. 1 presents bar graphs showing the tensile strength (left panel), Young's modulus (middle panel), and strain at break (right panel) of Epoxy—EP-520, having different (0%, 1%, 2%) concentration (wt.) of enrichment with the disclosed proteins.

The present invention, in some embodiments thereof, is directed to composites comprising a polymer and a mixture of proteins derived from a MaSp (major ampullate spidroin) protein, their improved mechanical properties, and the preparation of same.

The present invention provides, in some embodiments, composites comprising: (a) a mixture of proteins having a differing molecular weight useful for the preparation of synthetic dragline spider silk; and (b) a polymer.

In some embodiments, the term "composite" refers to a material which is composed of two or more substances having different characteristics and in which each substance retains its identity while contributing desirable properties to the whole.

In some embodiments, the term "material" refers to a solid material. In some embodiments, the term "material" refers to a semi-solid material (e.g., a gel).

In some embodiments, the disclosed composites exhibit superior mechanical properties.

In some embodiments, there is provided fiber comprising the mixture of proteins.

In some embodiments, a plurality of the disclosed fiber in some embodiments thereof, is attached to one another via the linker. Embodiments of the linker are described hereinbelow.

The Proteins

The present invention is based, in part, on the unexpected finding that artificial dragline spider silk, synthesized using a mixture of proteins of differing molecular weight and derived from a MaSp protein, has exceptional mechanical properties similar to the natural dragline spider silk.

In some embodiments, each protein in the mixture comprises, independently, "n" repeats of a repetitive region of a major MaSp protein, or a functional homolog, variant, derivative or fragment thereof, wherein m and n are, independently, an integer between 2 to 70.

As used herein, the term "mixture of proteins" or "protein mixture" refers to a plurality of proteins, such as, without limitation, at least 2, at least 3, at least 4, at least 5, at least 6, at least 7, at least 8, at least 9 or at least 10 types of proteins, wherein each type of protein has a unique and uniform molecular weight.

In some embodiments, the term "mixture of proteins" or "protein mixture" refers to 20 to 40 types of proteins or 20 to 35 types of proteins. In some embodiments, the protein refers to a single folded protein.

The terms "major ampullate spidroin protein" and "spidroin protein" are used interchangeably throughout the description and encompass all known major ampullate spidroin proteins, typically abbreviated "MaSp", or "ADF" in the case of *Araneus diadematus*. These major ampullate spidroin proteins are generally of two types, 1 and 2. These terms furthermore include non-natural proteins, as disclosed herein, with a high degree of identity and/or similarity to at least the repetitive region of the known major ampullate spidroin proteins. Additional suitable spider silk proteins include MaSp2, MiSp, MiSp2, AcSp, FLYS, FLAS, and flabelliform.

As used herein, the term "repetitive region", "repetitive sequence" or "repeat" refer to a recombinant protein sequence derived from repeat units which naturally occur multiple times in spider silk amino acid sequences (e.g., in the MaSp-1 protein). One skilled in the art will appreciate that the primary structure of the spider silk proteins is considered to consist mostly of a series of small variations of a unit repeat. The unit repeats in the naturally occurring proteins are often distinct from each other. That is, there is little or no exact duplication of the unit repeats along the length of the protein. In some embodiments, the synthetic spider silks of the invention are made wherein the primary structure of the protein comprises a number of exact repetitions of a single unit repeat. In additional embodiments, synthetic spider silks of the invention comprise a number of repetitions of one unit repeat together with a number of repetitions of a second unit repeat. Such a structure would be similar to a typical block copolymer. Unit repeats of several different sequences may also be combined to provide a synthetic spider silk protein having properties suited to a particular application. The term "direct repeat" as used herein is a repeat in tandem (head-to-tail arrangement) with a similar repeat. In another embodiment, the repeat used to form the synthetic spider silk of the invention is a direct repeat. In some embodiments, the repeat is not found in nature (i.e., is not a naturally occurring amino acid sequences).

An exemplary sequence comprising repetitive sequences is ADF-4: AAAAAAASGSGGYGPENQGPSGPVAYG-PGGPVSSAAAAAAAGSGPGGYGPENQGPSGPGGYG-PGGSGSSAAAAAAAASGPGGYGPGSQGPSGPGGSG-GYGPGSQGPSGPGASSAAA AAAAASGPGGYGPG-SQGPSGPGAYGPGGPGSSAAASGPGGYGPGSQGPS-GPGGSGGYGP GSQGPSGPGGPGASAAAAAAAAA-SGPGGYGPGSQGPSGPGAYGPGGPGSSAAASGPGG YGPGSQGPSGPGAYGPGGPGSSAAAAAAAGSGPG-GYGPGNQGPSGPGGYGPGGPGSSA AAAAAASGPG-GYGPGSQGPSGPGVYGPGGPGSSAAAAAAAGSGPG-GYGPGNQGPSGPG GYGPGGSGSSAAAAAAAAS-GPGGYGPGSQGPSGPGGSGGYGPGSQGPSGPGAS-SAAAA AAAASGPGGYGPGSQGPSGPGAYGPGGPGS-SAAASGPGGYGPGSQGPSGPGAYGPGGPG SSAAA-AAAASGPGGYGPGSQGPSGPGGSRGYGPGSQGP-GGPGASAAAAAAAASGPGG YGPGSQGPSGPGY-QGPSGPGAYGPSPSASAS (SEQ ID NO: 10). In some embodiments, the synthetic repetitive sequence of the invention is based on (e.g., has a high percentage identity, as defined hereinbelow) one or more repetitive sequences derived from ADF-4 (SEQ ID NO: 10). As used herein, the term "based on" refers to a sequence having a high percentage of homology to a repetitive sequence.

In some embodiments, each repetitive sequence comprises up to 60 amino acids, up to 55 amino acids, up to 50 amino acids, up to 49 amino acids, up to 48 amino acids, up to 47 amino acids, up to 46 amino acids, up to 45 amino acids, up to 44 amino acids, up to 43 amino acids, up to 42 amino acids, up to 41 amino acids, up to 40 amino acids, up to 39 amino acids, up to 38 amino acids, up to 37 amino acids, up to 36 amino acids or up to 35 amino acids, wherein possibility represents a separate embodiment of the present invention. In some embodiments, each repetitive sequence comprises 5 to 60 amino acids, 10 to 55 amino acids, 15 to 50 amino acids, 20 to 45 amino acids, 25 to 40 amino acids, acids, 25 to 39 amino acids or 28 to 36 amino acids, wherein possibility represents a separate embodiment of the present invention. In some embodiments, each repetitive sequence comprises 30 to 40 amino acids, 31 to 39 amino acids, 32 to 38 amino acids, 33 to 37 amino acids, 34 to 36 amino acids, wherein each possibility represents a separate embodiment of the present invention. In an additional embodiment, each repetitive sequence comprises 35 amino acids.

In some embodiments, n is an integer equal to any one of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 and 70.

In some embodiments, m is an integer equal to any one of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 and 70.

In another embodiment, the ratio of 'n' to 'm' is in the range of 2:1-1:2. In another embodiment, the ratio of 'n' to 'm' is in the range of 1.8:1-1:1.8. In another embodiment, the ratio of 'n' to 'm' is in the range of 1.5:1-1:1.5. In another embodiment, the ratio of 'n' to 'm' is in the range of 1.25:1-1:1.25. In another embodiment, the ratio of 'n' to 'm' is in the range of 1.2:1-1:1.2. The ratio of 'n' to 'm' is in the range of 1.1:1-1:1.1, in some embodiments. In another embodiment, 'n' and 'm' are equal.

In some embodiments, the n is identical for each type of protein in the mixture. The term "n is identical for each type of protein in the mixture" as used herein relates to the number of repetitive sequence for each type of protein, i.e., for one or more proteins having an identical molecular weight. As a non-limiting example, for a mixture of proteins having 16 types of proteins of differing molecular weight, each group of proteins has a different number of repetitive sequences.

In some embodiments, the various groups of proteins of the mixture have an inverse proportion between the number of repetitive sequence for each type of protein and the molar ratio of the group. In some embodiments, for each group of proteins (e.g., having an identical number of repeats), the lower the molecular weight of the proteins, the higher the molar ratio of the group.

In some embodiments, by "differing molecular weight" it is meant to refer to a molecular weights having a value that differs by at least e.g., 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 25%, or at least 30%.

In another embodiment, each repeat has a molecular weight in the range of 1.5 kDa to 4.5 kDa, in the range of 2 kDa to 3.5 kDa, in the range of 2.1 kDa to 3.4 kDa, in the range of 2.2 kDa to 3.3 kDa, in the range of 2.4 kDa to 3.2 kDa, in the range of 2.5 kDa to 3.1 kDa, in the range of 2.6 kDa to 3 kDa, or in the range of 2.7 kDa to 2.9 kDa, wherein each possibility represents a separate embodiment of the present invention. In another embodiment, each repeat has a molecular weight in the range of about 2.8 kDa.

In another embodiment, the composition comprises two or more proteins of the mixture having molecular weight increment of 2 kDa to 3.5 kDa, of 2.1 kDa to 3.4 kDa, of 2.2 kDa to 3.3 kDa, of 2.4 kDa to 3.2 kDa, of 2.5 kDa to 3.1 kDa, of 2.6 kDa to 3 kDa, or of 2.7 kDa to 2.9 kDa, wherein each possibility represents a separate embodiment of the present invention. In another embodiment, the composition comprises two or more proteins of the mixture having molecular weight increment of about 2.8 kDa.

In some embodiments, the repetitive region has a first moiety and a second moiety, wherein the first moiety and the second moiety are contiguous (i.e., immediately adjacent to each other). Typically, the first moiety and the second moiety are linked by a peptide bond.

In some embodiments, the first moiety of the repetitive region is an amino acid sequence of 5-30 amino acids comprising at least 95%, at least 90%, at least 85%, at least 80%, at least 75%, at least 60%, at least 55%, or at least 50% alanine residues. In some embodiments, the first moiety may comprise one or more glycine residues. In some embodiments, the first moiety comprises up to 5%, up to 10%, up to 15%, up to 20%, up to 25%, up to 30%, up to 45%, or up to 50% glycine residues.

In some embodiments, the first moiety comprises between one to fifty "n" repeats of an alanine-glycine dipeptide, such as in the formula of: $(AG)_{1-15}$. In some embodiments, the first moiety comprises between one to fifty "n" repeats of a glycine-alanine dipeptide, such as in the formula of: $(GA)_{1-15}$.

In some embodiments, the second moiety of the repetitive region is an amino acid sequence of 20-60 amino acids comprising at least 80% residues selected from the group consisting of glycine, serine, proline and tyrosine.

In some embodiments, the second moiety of the repetitive region is an amino acid sequence of 20-60 amino acids comprising at least 50%, at least 55%, at least 60%, at least 65%, at least 70%, at least 75%, at least 80%, at least 85%, at least 90%, at least 95% residues selected from the group consisting of glycine, serine, proline and tyrosine. In some embodiments, the second moiety of the repetitive region comprises not more than one or two glutamine residues. One skilled in the art will appreciate that the exact quantity and order of the glycine, serine, proline and tyrosine residues in the repetitive region may differ as long as the sequence forms self-assembling fibers.

In some embodiments, the repetitive region comprises:
(i) 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or 50% alanine residues;
(ii) 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or 50%, 51%, 52%, 53%, 54%, 55%, 56%, 57%, 58%, 59% or 60% glycine residues;
(iii) 10%, 11%, 12%, 13%, 14%, 15%, 16%, 17%, 18%, 19%, 20%, 21%, 22%, 23%, 24%, 25%, 26%, 27%, 28%, 29% or 30% serine residues;
(iv) 10%, 11%, 12%, 13%, 14%, 15%, 16%, 17%, 18%, 19%, 20%, 21%, 22%, 23%, 24%, 25%, 26%, 27%, 28%, 29% or 30% proline residues;
(v) 1%, 2%, 3%, 4%, 5%, 6%, 7%, 8%, 9% or 10% tyrosine residues;
(vi) 1%, 2%, 3%, 4%, 5%, 6%, 7%, 8%, 9% or 10% glutamine residues; and
(vii) 0%, 1%, 2%, 3%, 4%, 5%, arginine residues.

In some embodiments, the repetitive region comprises 13-42% of alanine residues, 25-55% glycine residues, 10-18% serine residues, 12-21% proline residues, 4-7% tyrosine residues, 4-7% glutamine residues, and 0-3% arginine residues.

In some embodiments, each of the proteins comprise, independently, an amino acid sequence as set forth in SEQ ID NO: 1

wherein $X_1$ is, independently, at each instance A or G.

In some embodiments, at least 50% of $(X_1)_Z$ is A, Z is an integer between 5 to 30; $X_2$ is S or G; $X_3$ is G or E; $X_4$ is G, S or N; $X_5$ is Q or Y; $X_6$ is G or S; $X_7$ is P or R; $X_8$ is Y or Q; $X_9$ is G or S; and $X_{10}$ is S or G.

In some embodiments, the mixture of proteins is characterized by one or more properties selected from the group consisting of:
(a) each repeat has a molecular weight in the range of 2 kDa to 3.5 kDa, and
(b) the ratio of 'n' to 'm' is in the range of 2:1 to 1:2.

In some embodiments, the n is identical for each type of protein in the mixture.

In another embodiment, n is an integer equal to or between 4 and 32. In another embodiment, m is an integer equal to or between 4 and 32. In another embodiment, the ratio of 'n' to 'm' is in the range of 1.8:1-1:1.8. In another embodiment, 'n' and 'm' are equal.

In some embodiments, Z is an integer between 6 to 11, an integer between 6 to 10 or an integer between 7 to 9. In one embodiment, Z is an integer selected from 5, 6, 7, 8, 9, 10, 11, and 12. In another embodiment, Z is 8.

In another embodiment, the repetitive region of a MaSP1 protein comprises the amino acid sequence as set forth in SEQ ID NO: 2 (SGPGGYGPGSQGPSGPG-GYGPGGPGSS). In another embodiment, the repetitive region of a MaSP1 protein comprises the amino acid sequence as set forth in SEQ ID NO: 3 (AAAAAAAASGPGGYGPGSQGPSGPGGYGPGGP-GSS).

In another embodiment, the homolog shares at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology with SEQ ID NO: 1.

In another embodiment, the homolog shares at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology with SEQ ID NO: 2.

In another embodiment, the homolog shares at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology with SEQ ID NO: 3.

In another embodiment, the repetitive region of a MaSP1 protein comprises the amino acid sequence as set forth in SEQ ID NO: 4. In another embodiment, the repetitive region of a MaSP1 protein has the amino acid sequence as set forth in SEQ ID NO: 10.

In another embodiment, each protein of the mixture further comprises a single N-terminal region selected from the group consisting of: SEQ ID NO: 5 (MSYYHEIR-EITIHDYDIPTTENLYFQGAMDPEFKGLRRRAQLV); SEQ ID NO: 6 (MSYYHEIREITIHDYDIPTTEN-LYFQGAMDPEFKGLRRRAQLVRPLSNLDNAP); SEQ ID NO: 7 (MSYYHEIREITIHDYDIPTTEN-LYFQGAMDPEFKGLRRRAQLVDPPGCRNSARAGS S), or any functional homolog, variant, derivative, or fragment thereof. In another embodiment, the homolog of the C-terminal region shares at least 70% homology with any one of SEQ ID NOs: 5-7.

In another embodiment, each protein of the mixture further comprises a single C-terminal region selected from the group consisting of: SEQ ID NO: 8 (VAAS-RLSSPAASSRVSSAVSSLVSSGPTNGAAVSGAL-NSLVSQISASNPGLSGCDALVQA LLELVSALVAILS-SASIGQVNVSSVSQSTQMISQALS); and SEQ ID NO: 9 (GPSGPGAYGPSPSASASVAASRLSSPAASSRVS-SAVSSLVSSGPTNGAAVSGALNSLVSQI SASNPGL-SGCDALVQALLELVSALVAILSSASIGQVNVSSVSQ-STQMISQALS), or any functional homolog, variant, derivative, fragment or mutant thereof. In another embodiment, the homolog of the N-terminal region shares at least 70% homology with SEQ ID NO: 8-9.

In some embodiments, one or more proteins of the mixture further comprises at least one tag sequence. Non-limiting examples of tags which may be used in the present invention include a His tag, a HA tag, a T7 tag, and the like. An exemplary His tag comprises six His residues or consists of six His residues as set forth in SEQ ID NO: 11 (HHHHHH). In another embodiment, the tag is a HA tag comprising or consisting of the amino acid sequence as set forth in SEQ ID NO: 12 (YPYDVPDYA). In another embodiment, the tag is a T7 tag comprising or consisting of the amino acid sequence as set forth in SEQ ID NO: 13 (MASMTGGQQMG). The skilled person is well aware of alternative suitable tags or other fusion partners.

"Amino acid" as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

"Amino acid sequence" or "peptide sequence" is the order in which amino acid residues, connected by peptide bonds, lie in the chain in peptides and proteins. The sequence is generally reported from the N-terminal end containing free amino group to the C-terminal end containing free carboxyl group Amino acid sequence is often called peptide, protein sequence if it represents the primary structure of a protein, however one must discern between the terms "Amino acid sequence" or "peptide sequence" and "protein", since a protein is defined as an amino acid sequence folded into a specific three-dimensional configuration and that had typically undergone post-translational modifications, such as phosphorylation, acetylation, glycosylation, sulfhydryl bond formation, cleavage and the likes.

As used herein, "isolated" or "substantially purified", in the context of synthetic spider silk amino-acid sequences or nucleic acid molecules encoding the same, as exemplified by the invention, means the amino-acid sequences or polynucleotides have been removed from their natural milieu or have been altered from their natural state. As such "isolated" does not necessarily reflect the extent to which the amino-acid sequences or nucleic acid molecules have been purified. However, it will be understood that such molecules that have been purified to some degree are "isolated". If the molecules do not exist in a natural milieu, i.e. it does not exist in nature, the molecule is "isolated" regardless of where it is present. By way of example, amino-acid sequences or polynucleotides that do not naturally exist in humans are "isolated" even when they are present in humans.

The term "isolated" or "substantially purified", when applied to an amino acid sequence or nucleic acid, denotes that the amino acid sequence or nucleic acid is essentially free of other cellular components with which they are associated in the natural state. It may be in a homogeneous state, or alternatively in either a dry or aqueous solution. Purity and homogeneity are typically determined using analytical chemistry techniques such as polyacrylamide gel electrophoresis or high performance liquid chromatography. An amino acid sequence or nucleic acid which is the predominant species present in a preparation is substantially purified.

In some embodiments, the repeats are of a homolog, variant, derivative of a repetitive region of a MaSp1 protein or fragment thereof. In some embodiments, the repeats are of a homolog, variant, derivative of a repetitive region of an ADF-4 protein or fragment thereof.

As used herein, the term "functional" as in "functional homolog, variant, derivative or fragment", refers to an amino acid sequence which possesses biological function or activity that is identified through a defined functional assay. More specifically, the defined functional assay is the formation of self-assembling fibers in cells expressing the functional homolog, variant, derivative or fragment.

An amino acid sequence or a nucleic acid sequence is the to be a homolog of a corresponding amino acid sequence or a nucleic acid, when the homology is determined to be at least 50%, at least 55%, at least 60%, at least 65%, at least 70%, at least 75%, at least 80%, at least 85%, at least 90%, at least 92%, at least 94%, at least 96%, at least 98% or at least 99%.

Homology, as used herein, may be determined on the basis of percentage identity between two amino acid (peptide) or DNA sequences. In general the two sequences to be compared are aligned to give a maximum correlation between the sequences. The alignment of the two sequences is examined and the number of positions giving an exact amino acid (or nucleotide) correspondence between the two sequences determined, divided by the total length of the alignment multiplied by 100 to give a percentage identity figure. This percentage identity figure may be determined over the whole length of the sequences to be compared, which is particularly suitable for sequences of the same or very similar lengths and which are highly homologous, or over shorter defined lengths, which is more suitable for sequences of unequal length or which have a lower level of homology. Methods for comparing the identity of two or more sequences are well known in the art. Thus for instance, programs available in the Wisconsin Sequence Analysis Package, version 9.1, for example the programs GAP and BESTFIT, may be used to determine the percentage identity between two amino acid sequences and the percentage identity between two polynucleotides sequences. BESTFIT uses the "local homology" algorithm of Smith and Waterman and finds the best single region of similarity between two sequences. BESTFIT is more suited to comparing two polypeptide or two polynucleotide sequences which are dissimilar in length, the program assuming that the shorter sequence represents a portion of the longer. In comparison, GAP aligns two sequences finding a "maximum similarity" according to the algorithm of Needleman and Wunsch. GAP is more suited to comparing sequences which are approximately the same length and an alignment is expected over the entire length. Preferably the parameters "Gap Weight" and "Length Weight" used in each program are 50 and 3 for polynucleotide sequences and 12 and 4 for polypeptide sequences, respectively. Preferably, percentage identities and similarities are determined when the two sequences being compared are optimally aligned.

The terms "identical", "substantial identity", "substantial homology" or percent "identity", in the context of two or more amino acids or nucleic acids sequences, refer to two or more sequences or subsequences that are the same or have a specified percentage of amino acid residues or nucleotides that are the same (i.e., about 60% identity, or at least 65%, at least 70%, at least 75%, at least 80%, at least 85%, at least 90%, at least 91%, at least 92%, at least 93%, at least 94%, at least 95%, at least 96%, at least 97%, at least 98%, or 99% identity over a specified region (e.g., amino acid sequence SEQ ID NO: 2 or 3), when compared and aligned for maximum correspondence over a comparison window or designated region) as measured using a BLAST or BLAST 2.0 sequence comparison algorithms with default parameters described below, or by manual alignment and visual inspection. Such sequences are then to be "substantially identical". This definition also refers to, or may be applied to, the compliment of a test sequence. The definition also includes sequences that have deletions and/or additions, as well as those that have substitutions. The preferred algorithms can account for gaps and the like.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

It should be appreciated that the invention further encompasses amino acid sequence comprising "n" repeats of a variant of any one of SEQ ID NO: 1, 2, or 3. As used herein, the term "variant" or "substantially similar" comprises sequences of amino acids or nucleotides different from the specifically identified sequences, in which one or more (e.g., 1, 2, 3, 4, 5, 6, 7, 8, 9, 10, 20 or 25) amino acid residues or nucleotides are deleted, substituted or added. The variants may be allelic variants occurring naturally or variants of non-natural origin. The variant or substantially similar sequences refer to fragments of amino acid sequences or nucleic acids that may be characterized by the percentage of the identity of their amino acid or nucleotide sequences with the amino acid or nucleotide sequences described herein, as determined by common algorithms used in the state-of-the-art. The preferred fragments of amino acids or nucleic acids are those having a sequence of amino acids or nucleotides with at least around 40 or 45% of sequence identity, preferentially around 50% or 55% of sequence identity, more preferentially around 60% or 65% of sequence identity, more preferentially around 70% or 75% of sequence identity, more preferentially around 80% or 85% of sequence identity, yet more preferentially around 90%, 91%, 92%, 93%, 94%, 95%, 96%, 97%, 98% or 99% of sequence identity when compared to the sequence of reference.

In one embodiment, a mixture of proteins is a fiber. In one embodiment, a fiber comprises a mixture of proteins. In one embodiment, a fiber comprises "m" types of proteins. In one embodiment, "m" types of proteins is a fiber. In one embodiment, "m" types of proteins is a mixture of proteins. In one embodiment, a fiber or a mixture of proteins comprises "m" types of proteins of differing molecular weight, wherein each protein in the "m" types of proteins comprises, independently, "n" repeats of a repetitive region of a major ampullate spidroin (MaSp) protein, or a functional homolog, variant, derivative or fragment thereof. In one embodiment, a mixture of proteins comprises "m" types of proteins of differing molecular weight, wherein each protein in the mixture of proteins comprises, independently, "n" repeats of a repetitive region of a major ampullate spidroin (MaSp) protein, or a functional homolog, variant, derivative or fragment thereof.

In one embodiment, a mixture of proteins or a fiber is composed of monomers. In one embodiment, a plurality of monomers are arranged in a nanofibril. In one embodiment, a plurality of nanofibrils are arranged in a fiber or make-up a fiber. In one embodiment, a monomer or a nanofibril within a mixture of proteins or a fiber has a diameter of 4 to 16 nm. In one embodiment, a monomer or a nanofibril within a mixture of proteins or a fiber has a diameter of 6 to 14 nm. In one embodiment, a monomer or a nanofibril within a mixture of proteins or a fiber has a diameter of 8 to 12 nm.

In one embodiment, a fiber or a mixture of proteins has a diameter of 70 to 450 nm. In one embodiment, a fiber or a mixture of proteins has a diameter of 80 to 350 nm. In one embodiment, a fiber or a mixture of proteins has a diameter of 80 to 300 nm. In one embodiment, a fiber or a mixture of proteins has a diameter of 150 to 250 nm. In one embodiment, a fiber or a mixture of proteins is arranged as a coil. In one embodiment, a single fiber or one mixture of proteins is arranged as a coil. In one embodiment, a coil has a diameter of 5 to 800 micrometers. In one embodiment, a coil has a diameter of 5 to 500 micrometers. In one embodiment, a coil has a diameter of 5 to 30 micrometers. In one embodiment, a coil has a diameter of 5 to 20 micrometers. In one embodiment, a fiber or a mixture of proteins has a length of 5 to 800 micrometers. In one embodiment, a fiber or a mixture of proteins has a length of 30 to 300 micrometers.

In one embodiment, a composite and/or a composition as described herein comprises an amount of less than 5% or 3% fibers equal to or shorter than 5 micrometers (in length) from the total number of fibers within the composite and/or a composition. In one embodiment, a composite and/or a composition as described herein comprises an amount of less than 5% or 3% fibers equal to or shorter than 8 micrometers (in length) from the total number of the total content of fibers within the composite and/or a composition.

In one embodiment, a composite and/or a composition as described herein comprises less than 5% or 3% w/w fibers equal to or shorter than 5 micrometers (in length) from the total weight of fibers within the composite and/or a composition. In one embodiment, a composite and/or a composition as described herein comprises an amount of less than 5% or 3% w/w fibers equal to or shorter than 8 micrometers (in length) from the total weight of the total content of fibers within the composite and/or a composition.

In one embodiment, fibers equal to or shorter than 5 or 8 micrometers cause instability. In one embodiment, fibers equal to or shorter than 5 or 8 micrometers reduce the integrity of a composition or a composite as described herein. In one embodiment, fibers equal to or shorter than 5 or 8 micrometers reduce the physical strength of a composition or a composite as described herein.

In one embodiment, a fiber or a mixture of proteins is branched. In one embodiment, a fiber or a mixture of proteins comprises 1 to 10 branches. In one embodiment, a fiber or a mixture of proteins is free of carbohydrates. In one embodiment, a fiber or a mixture of proteins is non-glycosylated. In one embodiment, a fiber or a mixture of proteins is free of fat or fatty acids. In one embodiment, a fiber or a mixture of proteins is free of phosphorus. In one embodiment, "free of" is "devoid of" or essentially "devoid of".

In one embodiment, at least 50% of proteins within a fiber or a mixture of proteins are bigger/larger/heavier (in kDa) than the median weight of the proteins within a fiber or a mixture of proteins. In one embodiment, at least 55% of proteins within a fiber or a mixture of proteins are bigger/larger/heavier (in kDa) than the median weight of the proteins within a fiber or a mixture of proteins. In one embodiment, at least 60% of proteins within a fiber or a mixture of proteins are bigger/larger/heavier (in kDa) than the median weight of the proteins within a fiber or a mixture of proteins. In one embodiment, at least 65% of proteins within a fiber or a mixture of proteins are bigger/larger/heavier (in kDa) than the median weight of the proteins within a fiber or a mixture of proteins. In one embodiment, at least 70% of proteins within a fiber or a mixture of proteins are bigger/larger/heavier (in kDa) than the median weight of the proteins within a fiber or a mixture of proteins. In one embodiment, at least 75% of proteins within a fiber or a mixture of proteins are bigger/larger/heavier (in kDa) than the median weight of the proteins within a fiber or a mixture of proteins.

In one embodiment, the aspect ratio of length to diameter of a fiber or a mixture of proteins is at least 1:10. In one embodiment, the aspect ratio of length to diameter of a fiber or a mixture of proteins is at least 1:10 to 1:1500. In one embodiment, the aspect ratio of length to diameter of a fiber or a mixture of proteins is at least 1:50 to 1:1000. In one embodiment, the aspect ratio of length to diameter of a fiber or a mixture of proteins is at least 1:100 to 1:1200. In one embodiment, the aspect ratio of length to diameter of a fiber or a mixture of proteins is at least 1:100 to 1:1000. In one embodiment, the aspect ratio of length to diameter of a fiber or a mixture of proteins is at least 1:500 to 1:1000.

The terms derivatives and functional derivatives as used herein mean the amino acid sequence of the invention with any insertions, deletions, substitutions and modifications.

It should be appreciated that by the term "insertions", as used herein it is meant any addition of amino acid residues to the sequence of the invention, of between 1 to 50 amino acid residues, specifically, between 20 to 1 amino acid residues, and more specifically, between 1 to 10 amino acid residues. Most specifically, 1, 2, 3, 4, 5, 6, 7, 8, 9 and 10 amino acid residues. Further, the amino acid sequence of the invention may be extended at the N-terminus and/or C-terminus thereof with various identical or different amino acid residues.

Amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

In another embodiment, the repeat sequence of the invention has 17 or fewer, 16 or fewer, 15 or fewer, 14 or fewer, 13 or fewer, 12 or fewer, 11 or fewer, 10 or fewer, 9 or fewer, 8 or fewer, or 7 or fewer amino acid substitutions to the sequence of any one of SEQ ID NO: 2 or 3. In one embodiment, the repeat sequence of the invention has at least 2, at least 3, at least 4, at least 5, at least 6, at least 7, at least 8, at least 9, at least 10, at least 11, at least 12, or at least 13 amino acid substitutions to the sequence of any one of SEQ ID NO: 2 or 3.

With respect to amino acid sequences, one of skill will recognize that individual substitutions, deletions or additions to an amino acid, nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

Conservative nucleic acid substitutions are nucleic acid substitutions resulting in conservative amino acid substitutions as defined above.

Variants of the amino acid sequences of the invention may have at least 80% sequence similarity, at least 85% sequence similarity, 90% sequence similarity, or at least 95%, 96%, 97%, 98%, or 99% sequence similarity at the amino acid level, with a repeating unit denoted by any one of SEQ ID NO: 2 or 3.

The amino acid sequence of the invention may comprise "n" repeats of SEQ ID NO. 1 or SEQ ID NO. 3 or of any fragment thereof. A "fragment" constitutes a fraction of the amino acid or DNA sequence of a particular region. A fragment of the peptide sequence is at least one amino acid shorter than the particular region, and a fragment of a DNA sequence is at least one base-pair shorter than the particular region. The fragment may be truncated at the C-terminal or N-terminal sides, or both. An amino acid fragment may comprise at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 24, at least 26, at least 27, at least 28, at least 29, at least 30, at least 31, at least 32, at least 33 or at least 34 amino acids of SEQ ID NO: 1 or 3.

Mutants of the amino acid sequences of the invention are characterized in the exchange of one (point mutant) or more, about up to 10, of its amino acids against one or more of another amino acid. They are the consequence of the corresponding mutations at the DNA level leading to different codons.

Still further, the invention concerns derivatives of the amino acid sequence of the invention. Derivatives of the amino acid sequences of the invention are, for example, where functional groups, such as amino, hydroxyl, mercapto or carboxyl groups, are derivatised, e.g. glycosylated, acylated, amidated or esterified, respectively. In glycosylated derivatives an oligosaccharide is usually linked to asparagine, serine, threonine and/or lysine. Acylated derivatives are especially acylated by a naturally occurring organic or inorganic acid, e.g. acetic acid, phosphoric acid or sulphuric acid, which usually takes place at the N-terminal amino group, or at hydroxy groups, especially of tyrosine or serine, respectively. Esters are those of naturally occurring alcohols, e.g. methanol or ethanol. Further derivatives are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

According to some aspects, the invention concerns an isolated nucleic acid sequence encoding two or more proteins of the mixture of proteins of the present invention. According to some embodiments, the invention provides an isolated nucleic acid sequence encoding the protein mixture of the present invention.

"Nucleic acid" refers to a molecule which can be single stranded or double stranded, composed of monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

Due to the degenerative nature of the genetic code it is clear that a plurality of different nucleic acid sequences can be used to code for the amino acid sequences of the invention. It should be appreciated that the codons comprised in the nucleic acid sequence of the invention may be optimized for expression in Sf9 host cells.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Within the context of the present invention, genes and DNA coding regions are codon-optimized for optimal expression in host cells, and in a specific example, Sf9 *Spodoptera frugiperda* insect cells.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

In some embodiments, the invention relates to one or more expression vectors comprising a nucleic acid sequence encoding the proteins mixture of the invention. In some embodiments, the invention relates to one or more expression vectors comprising a nucleic acid sequence encoding at least a portion of the proteins mixture of the invention (e.g., two or more group of proteins having a differing molecular weight). The amino acid sequence encoded by the nucleic acid sequence comprised within the expression vector of the invention may optionally further comprise at least one of a C-terminal region (e.g., denoted as SEQ ID NO: 8 or 9); and an N-terminal region (e.g., selected from SEQ ID NO: 5-7). It should be noted that the nucleic acid sequence is under expression control of operably linked promoter and, optionally, regulatory sequences.

As used herein, a "vector", "expression vector" or "plasmid" as referred to herein is an extra-chromosomal element often carrying genes which are not part of the central metabolism of the cell, and usually in the form of circular double-stranded DNA molecules. It may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. As used herein, "transformation" or "transfection" is the acquisition of new genes in a cell by the incorporation of nucleic acid. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined, namely, the expression of the synthetic spider silk proteins.

In specific embodiments, the vector is a viral vector, most specifically a baculovirus vector system or a vaccinia virus vector system. Examples of such commercially available baculovirus systems Baculo-Gold®, Flash-Bac® and the bac to bac system. Further viral vector systems may also be used in this invention. From case to case, a modification of the vector may be needed. Examples for further viral vectors are adenoviruses and all negative-strand RNA-viruses, e.g. rabies, measles, RSV, etc.

In one embodiment, a baculovirus system as used for expressing the synthetic silk protein of the invention. Baculoviruses are a family of large rod-shaped viruses that can be divided to two genera: nucleopolyhedroviruses and granuloviruses. They have a restricted range of hosts that they can infect that is typically restricted to a limited number of closely related insect species. Because baculoviruses are not harmful to humans they are a safe option for use in research and commercial or industrial applications. Baculovirus expression in insect cells represents a robust method for producing recombinant glycoproteins, a significant advantage over prokaryotic expression which is lacking in terms of glycosylation, and consequently, proper protein folding.

As indicated above, the expression vector of the invention is operably linked to a promoter. The terms "promoter" and "promoter region" refer to a sequence of DNA, usually upstream of (5' to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene. Theterm "suitable promoter" will refer to any eukaryotic or prokaryotic promoter capable of driving the expression of a synthetic spider silk variant gene.

Promoters which are useful to drive expression of heterologous DNA fragments in Sf9 are numerous and familiar to those skilled in the art. Virtually any promoter capable of driving the gene encoding a silk variant protein is suitable for the present invention. For example, polyhedrin, basic protein, p10, OpIE2 and gp4 promoters may be suitable promoters for the expression.

A coding sequence and regulatory sequences are the to be "operably linked" or "operably joined" when they are covalently linked in such a way as to place the expression or transcription of the coding sequence under the influence or control of the regulatory sequences. If the regulatory sequence is positioned relative to the gene such that the regulatory sequence is able to exert a measurable effect on the amount of gene product produced, then the regulatory sequence is operably linked to the gene. If it is desired that the coding sequences be translated into a functional protein, two DNA sequences are the to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence. Especially, such 5' non-transcribing regulatory sequences will include a promoter region which includes a promoter sequence for transcriptional control of the operably joined gene. Regulatory sequences may also include enhancer sequences or upstream activator sequences, as desired.

"Regulation" and "regulate" refer to the modulation of gene expression controlled by DNA sequence elements located primarily, but not exclusively upstream of (5' to) the transcription start of a gene. Regulation may result in an all or none response to stimulation, or it may result in variations in the level of gene expression.

In a further aspect, the invention concerns a host cell transformed with the expression vector according to the invention.

"Cells", "host cells" or "recombinant host cells" are terms used interchangeably herein. It is understood that such terms refer not only to the particular subject cells but to the progeny or potential progeny of such a cell. Because certain modification may occur in succeeding generation due to either mutation or environmental influences, such progeny may not, in fact, be identical to the parent cell, but are still included within the scope of the term as used herein.

"Host cell" as used herein refers to cells which can be recombinantly transformed with naked DNA or expression vectors constructed using recombinant DNA techniques. A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which require the induced phenotype for survival.

The host cells of the invention are transformed or transfected with the expression vector descried herein to express the synthetic spider silk protein of the invention. "Transformation", as used herein, refers to a process in which a cell's genotype is changed as a result of the cellular uptake of exogenous DNA or RNA, and, for example, the transformed cell expresses a recombinant form of the desired synthetic spider silk protein. The term "transfection" means the introduction of a nucleic acid, e.g., naked DNA or an expression vector, into a recipient cells by nucleic acid-mediated gene transfer.

In one specific embodiment, the host cells transformed with the expression vector according to the invention are insect cells. As insect cells, Lepidoptera insect cells may be used, more specifically cells from *Spodoptera frugiperda* and from *Trichoplusia ni*. Most specifically, the insect cell is a Sf9, Sf21 or high 5 cells.

In some embodiments, the silk protein of the invention is devoid of post translational modifications.

In some embodiments, the silk protein of the invention is biodegradable. This characteristic may be of importance, for example, in the field of medicine, whenever the silk proteins are intended for an in vivo use, in which biological degradation is desired. This characteristic may in particular find application in suture materials and wound closure and coverage systems.

According to some aspects, the invention concerns an expression vector comprising the nucleic acid sequence of the present invention, wherein the nucleic acid sequence is under expression control of an operably linked promoter and, optionally, regulatory sequences.

In some embodiments, the mixture of proteins results in a self-assembled forming a defined structure. In some embodiments, the mixture of proteins is in the form of a network. In some embodiments, the mixture of proteins is in the form of a complex. In some embodiments, the mixture of proteins induce a defined secondary structure, e.g., a beta turn, gamma turn, beta sheet, alpha helix conformation, and the like.

According to some aspects, the disclosed mixture of proteins is in the form of a fiber. A "fiber" as used herein, is meant a fine cord of fibrous material composed of two or more filaments twisted together. By "filament" is meant a slender, elongated, threadlike object or structure of indefinite length, ranging from microscopic length to lengths of a mile or greater. Specifically, the synthetic spider silk filament is microscopic, and is proteinaceous. By "biofilament" is meant a filament created from a protein, including recombinantly produced spider silk protein. In some embodiments, the term "fiber" does not encompass unstructured aggregates or precipitates.

In some embodiments, the fiber of the proteins is characterized by size of at least one dimension thereof (e.g., diameter, length). For example, and without limitation, the diameter of the fiber is between 10 nm-1 µm, 20-100 nm, or 10-50 nm.

In some embodiments, the fiber is composed of nanofibrils. In some embodiments, the nano-fibrils have a diameter of e.g., 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 40 nm, about 42 nm, about 44 nm, about 46 nm, about 48 nm, or about 50 nm, including any value or range therebetween. In one embodiment, the nano-fibrils have a diameter of 3-7 nm. In one embodiment, the nano-fibrils have a diameter of 4-6 nm.

In some embodiments, the length of the disclosed fiber is between 1-200 µm, 10-100 µm, 100 to 500 µm or 200-500 µm.

In some embodiments of any one of the embodiments described herein, the disclosed fiber is characterized by a porous structure. In some embodiments, the porous structure is characterized by a porosity of at least 30% (e.g., from 30 to 99%). In some embodiments, the porous structure is characterized by a porosity of at least 50% (e.g., from 50 to 99%). In some embodiments, the porous structure is characterized by a porosity of at least 60% (e.g., from 60 to 99%). In some embodiments, the porous structure is characterized by a porosity of at least 70% (e.g., from 70 to 99%). In some embodiments, the porous structure is characterized by a porosity of at least 80% (e.g., from 80 to 99%). In some embodiments, the porous structure is characterized by a porosity of at least 90% (e.g., from 90 to 99%). In some embodiments, the porous structure is characterized by a porosity of about 90%.

Herein, the term "porosity" refers to a percentage of the volume of a substance (e.g., a "sponge-like" material) which consists of voids. In another embodiment, porosity is measured according to voids within the surface area divided to the entire surface area (porous and non-porous).

In some embodiments, the porous structure of the disclosed fibers allows absorbing water efficiently on the fiber surface. That is, and without being bound by any particular theory, this surprising discovery can be explained in view of the disclosed fiber structure and its porosity which is in sharp distinction from native spider silk found in nature.

In some embodiments of any one of the embodiments described herein, the disclosed fiber is characterized by a mean diameter is nanosized.

In some embodiments, the disclosed fiber is characterized by a mean diameter is in a range of from 1 to 50 nm. In some such embodiments, the mean diameter is in a range of from 3 to 50 nm. In some such embodiments, the mean diameter is in a range of from 5 to 50 nm. In some such embodiments, the mean diameter is in a range of from 1 to 40 nm. In some such embodiments, the mean diameter is in a range of from 1 to 30 nm. In some such embodiments, the mean diameter is in a range of from 5 to 40 nm. As further exemplified in the Examples section below, in some embodiments, a plurality of the disclosed fibers may be in the form of self-assembled structure or matrix. In some embodiments, this matrix can be rendered suitable for biomaterial applications.

In some embodiments, a fiber or a mixture of proteins comprises "m" types of proteins of differing molecular weight, wherein each protein in said "m" types of proteins comprises, independently, "n" repeats of a repetitive region of a major ampullate spidroin (MaSp) protein, or a functional homolog, variant, derivative or fragment thereof, wherein m is an integer between 2 to 70 and n is an integer between 6 to 70. In some embodiments, a fiber or a mixture of proteins comprises "m" types of proteins of differing molecular weight, wherein each protein in said "m" types of proteins comprises, independently, "n" repeats of a repetitive region of a major ampullate spidroin (MaSp) protein, or a functional homolog, variant, derivative or fragment thereof, wherein m is an integer between 2 to 70 and n is an integer between 7 to 70. In some embodiments, a fiber or a mixture of proteins comprises "m" types of proteins of differing molecular weight, wherein each protein in said "m" types of proteins comprises, independently, "n" repeats of a repetitive region of a major ampullate spidroin (MaSp) protein, or a functional homolog, variant, derivative or fragment thereof, wherein m is an integer between 2 to 70 and n is an integer between 8 to 70. In one embodiment "n" repeats of a repetitive region of a major ampullate spidroin (MaSp) protein must be equal or greater than 6 in order to efficiently support cell growth, cell expansion and proliferation, multi-layer cell assembly, cell migration, reduced cell death, tissue regeneration and/or healing processes. In one embodiment "n" repeats of a repetitive region of a major ampullate spidroin (MaSp) protein must be equal or greater than 7 in order to efficiently support cell growth, cell expansion and proliferation, multi-layer cell assembly, cell migration, reduced cell death, tissue regeneration and/or healing processes. In one embodiment "n" repeats of a repetitive region of a major ampullate spidroin (MaSp) protein must be equal or greater than 8 in order to efficiently support cell growth, cell expansion and proliferation, multi-layer cell assembly, cell migration, reduced cell death, tissue regeneration and/or healing processes. In one embodiment "n" repeats of a repetitive region of a major ampullate spidroin (MaSp) protein must be equal or greater than 9 in order to efficiently support cell growth, cell expansion and proliferation, multi-layer cell assembly, cell migration, reduced cell death, tissue regeneration and/or healing processes. In one embodiment "n" repeats of a repetitive region of a major ampullate spidroin (MaSp) protein must be equal or greater than 10 in order to efficiently support cell growth, cell expansion and proliferation, multi-layer cell assembly, cell migration, reduced cell death, tissue regeneration and/or healing processes.

In some embodiments, one or more fibers in the disclosed matrix comprise at least 6, at least 7, least 8, at least 9, at least 10, at least 11, or at least 12, repeats ("n" as defined hereinabove). In some embodiments, one or more fibers in the disclosed matrix comprise are: 6-70, 7, 8-70, 9-70, 10-70, 11-70, 12-70, 13-70, 14-70, 15-70, 16-70, 17-70, 18-70, 19-70, or 20-70 repeats ("n" as defined hereinabove). In some embodiments, the cell, medical and biological compositions and methods as described herein require at least 6 repeats. In some embodiments, the cell, medical and biological compositions and methods as described herein require at least 7 repeats. In some embodiments, the cell, medical and biological compositions and methods as described herein require at least 8 repeats. In some embodiments, the cell, medical and biological compositions and methods as described herein require: 6-70, 7, 8-70, 9-70, 10-70, 11-70, 12-70, 13-70, 14-70, 15-70, 16-70, 17-70, 18-70, 19-70, or 20-70 repeats ("n" as defined hereinabove).

In some embodiments, this matrix is suitable for cell growth, and for maintaining or promoting cellular activity, as further demonstrated hereinbelow.

In some embodiments, the term "self-assembled" refers to a resulted structure of a self-assembly process (e.g., spontaneous self-assembly process) based on a series of associative chemical reactions between at least two domains of the fiber(s), which occurs when the associating groups on one domain are in sufficient proximity and are oriented so as to allow constructive association with another domain. In other words, an associative interaction means an encounter that results in the attachment of the domains of a fiber or fibers to one another. In some embodiments, attached domains are not parallel to each other. Also contemplated are arrangements in which there are more than two domains of the self-assembled structure, each engaging a different plane.

In some embodiments, the density of the nano-fibril also affects the properties of the self-assembled fibers. In some embodiments, the density (in $g/cm^3$) of the nano-fibril is from 0.5 to 1.5, e.g., 0.5, 0.6, 0.7, 0.8, 0.9, 1, 1.1, 1.2, 1.3, 1.4, 1.5, including any value and range therebetween. In exemplary embodiments, the density of a single nano-fibril is about 1.3 $g/cm^3$.

It is noteworthy, that in some embodiments, the density of the self-assembled fiber (e.g., about 80% voids) is in the range of from 0.1 $g/cm^3$ to 0.4 $g/cm^3$ or from 0.2 $g/cm^3$ to 0.3 $g/cm^3$. In exemplary embodiments, the density of the self-assembled fiber is about 0.26 $g/cm^3$.

Wettability study of surfaces at nano-scale spatial resolution and high temporal resolution is an emerging field from both theoretical and practical aspects.

As demonstrated in the Examples section that follows, the disclosed fiber exhibited a high degree of surface's wettability exhibiting a remarkable ability to absorb fluids in comparison with their volume and weight.

The Composites and Mechanical Properties

In some embodiments, the disclosed composite is characterized by an improved mechanical property as compared to a reference material. In some embodiments, the term "reference material" refers to a same chemical composition as in the composite, being free of the one or more proteins. In some embodiments, the term "reference material" refers to a plain polymer (i.e. not comprising the proteins) having polymeric molecular weight ($M_w$) as in the composite.

In some embodiments, the term "reference material" refers to a plain polymer having same monomer and molecular configuration (e.g., degree and type of crystallinity). In some embodiments, the term "reference material" refers to a plain polymer having same molecular configuration (e.g., degree and type of crystallinity). In some embodiments, the term "reference material" refers to a plain polymer having a backbone derived from the same monomeric units. In some embodiments, the term "reference material" refers to the corresponding monomer.

By "improved mechanical property" it is meant to refer to having a more desirable mechanical property.

In some embodiments, the composite is in the form of a matrix. Herein, the term "matrix" (including "core matrix"), may refer to a multi-layer matrix. In some embodiments, the term "matrix" refers to one or more layers of one or more polymers which further include the mixture of proteins incorporated within the layer(s) and/or interposed between the layers.

In some embodiments, the improved mechanical property refers to an elastic modulus. In some embodiments, the phrase "elastic modulus" refers to Young's modulus. In some embodiments, the phrase "elastic modulus" is determined by response of a material to application of tensile stress (e.g., according to procedures known in the art).

In some embodiments, as further shown in the Examples section below, the improved mechanical property refers to Flexural modulus. As used herein and in the art, the flexural modulus (also referred to as "bending modulus") is the ratio of stress to strain in flexural deformation, or the tendency for a material to bend. Flexural modulus may be determined from the slope of a stress-strain curve.

In some embodiments, the property is selected from, without being limited thereto, Young's modulus, tensile strength, fracture strain, yield point, toughness, stiffness, creep resistance, work-to-failure, stress and percentage of elongation.

Stiffness refers to the slope of the linear portion of a load-deformation curve. Work to failure refers to the area under the load-deformation curve before failure. Each of these can be measured and calculated by methods standard known in the art.

In some embodiments, the tensile strength of a material refers the maximum amount of tensile stress that it can take before failure, for example breaking.

In some embodiments, the term "tensile strength" as used herein is the maximum amount of force as measured e.g., in Newton's that a material can bear without or prior to tearing, breaking, necking forming microcracks or fractures.

By "tearing, breaking, necking forming microcracks or fractures" it is meant to refer to a permanent deformation. In some embodiments, the term "permanent deformation" does not include microcracks or fractures. In some embodiments, by "permanent deformation" it is meant to refer to relative to at least 0.1%, 0.2%, 0.3%, 0.4%, 0.5%, or 1% of the original dimension or structure, including any value therebetween.

In some embodiments, the term "fracture strain" means the strain (displacement) at fracture, as determined e.g., by the stress-strain curve in a tensile test.

In some embodiments, the term "yield point" refers to the stress at which the stress-strain curve has a plateau and the elastic limit is reached. As used herein, "creep" is a measure of the change in tensile strain when a polymer sample is subjected to a constant tensile stress, for instance, gravity or applied mechanical or physical stress. Put differently, creep is the tendency of a solid material to slowly move or deform permanently under the influence of a constant tensile stress. As used herein, the term "creep resistance" refers to a polymer's ability to resist any kind of distortion when under a load over an extended period of time. "Improved creep resistance" refers to improvement by e.g., 20 percent of the time to e.g., 5% tensile strain.

In some embodiments, the term "stress at elongation" refers to the force that acts on the material in the stretched condition. For example, "stress at 100% elongation" refers to the force that acts on the material stretched to twice its length.

In some embodiments, one or more properties selected from Young's modulus, tensile strength, yield point, and stress at elongation, is enhanced by e.g., at least 1%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 50%, at least 100%, at least 200%, or at least 500%.

In some embodiments, at least two properties selected from Young's modulus, tensile strength, yield point, and stress at elongation, is enhanced by e.g., at least 1%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 50%, at least 100%, at least 200%, or at least 500%.

In some embodiments, at least three properties selected from Young's modulus, tensile strength, yield point, and stress at elongation, are enhanced by e.g., at least 1%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 50%, at least 100%, at least 200%, or at least 500%.

In some embodiments, the Young's modulus is enhanced by e.g., at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 50%, at least 100%, at least 200%, or at least 500%.

In some embodiments, the tensile strength is enhanced by e.g., at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, or at least 50%.

In some embodiments, the yield point is enhanced by e.g., at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, or at least 50%.

In some embodiments, the composite is characterized by a structural strength, wherein more than 1% of the structural strength results from the protein fiber.

Without being bound by any particular theory it is to be understood that the mixture of proteins results in a successful self-assembly which in turn results in a protein fiber. The enforcement of a polymeric composite is derived from the fiber(s) incorporated therein. In some embodiments, the composite is characterized by a structural strength, wherein more than 5% of the structural strength results from the incorporation of the protein fiber(s). In some embodiments, the composite is characterized by a structural strength, wherein more than 10% of the structural strength results from the incorporation of the protein fiber.

In some embodiments, the composite is characterized by a structural strength, wherein more than 20% of the structural strength results from the incorporated protein fiber(s). In some embodiments, the composite is characterized by a structural strength, wherein more than 30% of the structural strength results from the incorporated protein fiber(s).

In some embodiments, the composite is characterized by a structural strength, wherein more than 1% of the tensile strength results from the incorporated protein fiber(s). In some embodiments, the composite is characterized by a structural strength, wherein more than 5% of the tensile strength results from the incorporated protein fiber(s). In some embodiments, the composite is characterized by a structural strength, wherein more than 10% of the tensile strength results from the incorporated protein fiber(s). In some embodiments, the composite is characterized by a structural strength, wherein more than 20% of the tensile strength results from the incorporated protein fiber(s). In some embodiments, the composite is characterized by a tensile strength, wherein more than 30% of the structural strength results from the incorporated protein fiber(s).

In some embodiments, the phrase "structural strength", as used herein, refers to the mechanical properties such as, without being limited thereto, elastic modulus, tensile stress, elongation (strain) and toughness [e.g., combination of tensile stress and elongation (strain)].

In some embodiments, the term "polymer", as used hereinthroughout, describes a substance, e.g., an organic substance, but alternatively an inorganic substance, composed of a plurality of repeating structural units (referred to interchangeably as backbone units or monomeric units) covalently connected to one another and forming the polymeric backbone of the polymer. The term "polymer" as used herein encompasses organic and inorganic polymers and further encompasses one or more of a homopolymer, a copolymer or a mixture thereof (e.g., a blend). The term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone units can differ from one another by the pendant groups thereof.

For the sake of simplicity, the terms "polymer" and "polymeric backbone" as used hereinthroughout interchangeably, relate to both homopolymers, copolymers and mixtures thereof.

In some embodiments, the polymer is hydrophobic. In some embodiments the polymer is UV cured.

In some embodiments, the disclosed composite is biostable. In some embodiments, the disclosed composite is biocleavable. In some embodiments, the disclosed composite is biodegradable.

In some embodiments, the term "biostable" describes a compound or a polymer that remains intact under physiological conditions (e.g., is not degraded in vivo, and hence is non-biodegradable or non-biocleavable).

In some embodiments, the term "biodegradable" describes a substance which can decompose under physiological and/or environmental condition(s) into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percent of the substance decompose within a time period shorter than one year.

In some embodiments, the term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

The Polymers

In some embodiments, the polymer is or comprises a synthetic polymer. In some embodiments, the polymer is or comprises a natural polymer. A natural polymer may refer to a polymer made of, without limitation, a natural source such as plants, animal and mineral sources, or can be woven from natural fibers such as cotton, linen, jute, flax, ramie, sisal and hemp, a structure of the keratin fibers (hair), and wool.

Further exemplary natural polymer comprises polylactide, collagen, Keratin, cellulose, actine, myosine, chitin, *Bombyx mori* silk.

In some embodiments, the polymer is a thermoplastic polymer. In some embodiments, the polymer is a thermoset. In some embodiments, the polymer is an epoxy. In some embodiments, the polymer is polyester (e.g., aliphatic polyesters). In some embodiments, the polymer is selected from the group consisting of polyamides, polyurethane, and Nylons. In some embodiments, the polymer is a cross-linked polymer. In some embodiments, the polymer is copolymer. In some embodiments, the polymer is in the form of a hydrogel.

In some embodiments, the polymeric materials are two or more component-materials (e.g., copolymer). As demonstrated in the Example section that follows, component (also referred to as "part") A may be the main (base) polymer, and part B may be e.g., a hardener or a catalyst.

Hardener chemical families vary with the polymer base, but includes amines, isocyanates, peroxides and few others.

Copolymer may be produced by a mechanism selected from radical polymerization process (e.g., using Azobisisobutyronitrile (abbreviated AIBN)), a step-growth polymerization and a chain growth polymerization.

The term "epoxy", as used herein, refers to a reactive group which is a three membered heterocyclic molecule with one oxygen and two methylene groups, having a molecular formula of —$C_2H_3O$.

In some embodiments, the polymer is selected from, without being limited thereto, liquid crystal polymers, maleic anhydride grafted polypropylene, polyamides Nylon 4,6, Nylon 6, Nylon 6,6, Nylon 11, Nylon 12, polyacrylates such as PMMA (polymethylmetacrylate), poly(arylamide), polyethylene (PE), high density PE (HDPE), low density PE (LDPE), Ultra-high-molecular-weight polyethylene (UHMWPE), polybutylene terephthalate, polyethylene terephthalate, polyphenylene sulfide, polyphthalamide, polypropylene, polystyrene, poly(vinylidene fluoride), Poly(2-hydroxyethyl methacrylate) (pHEMA), thermoset and thermoplastic polyurethane, polycarbonate, polyvinyl butyral, ethylene vinyl alcohol copolymer, polyvinyl chloride (PVC), Fluroinated polymers such as polytetrafluoroethylene (PTFE), polylactic acid (PLA) or a copolymer thereof (e.g., poly(lactic-co-glycolic acid) (PLGA)), polycaprolactone (PCL) or a copolymer thereof, polyethylene glycol, latex, rubber (e.g., natural rubber, synthetic rubber, butadiene rubber, styrene-butadiene rubber, chloroprene rubber, butyl rubber, nitrile rubber, isoprene rubber, polyurethane rubber, acrylonitrile-butadiene-styrene (ABS)), polyetherketone (PEK), polyetheretherketone (PEEK), polyetherketoneketone (PEKK) and polyetheretherketoneketone (PEEKK). thermoplastic elastomers, styrene-butadiene copolymer rubber (SBR)), xanthan, cellulose, collagen, elastin, keratin, cotton, wool, silk and any combination or mixture thereof.

By "cellulose" it is also meant to include a derivative thereof, including, without being limited thereto, cellulose nitrate, triacetyl cellulose (TAC), and cellulose acetate propionate (CAP).

In some embodiments, the polymer is selected from, without being limited thereto, materials used as adhesives, selected from, without being limited thereto, epoxy, cyanoacrylates, polyesters, polyols, polyurethanes, and polyimides.

In some embodiments, the polymer is a protein derived polymer. In some the protein derived polymer is not derived from MaSp protein.

In some embodiments, the polymer is a non-protein derived polymer.

As used herein, the term "hydrogel" refers to a three-dimensional fibrous network containing from about 50%, or from about 80%, and up to 99.9% (by mass) water. A hydrogel can be regarded as a material which is mostly water, yet behaves like a solid or semi-solid due to a three-dimensional crosslinked network within the liquid, made of natural and/or synthetic polymeric chains.

According to some embodiments of the present invention, a hydrogel may contain polymeric chains of various lengths and chemical compositions which may stem from monomers, oligomers, block-polymeric units, which are interconnected (crosslinked) by chemical bonds (e.g., covalent, hydrogen and ionic/complex/metallic bonds).

In some embodiments, the hydrogel may contain macromolecular polymeric and/or fibrous elements which are not chemically connected to the main crosslinked network but are rather mechanically intertwined therewith and/or immersed therein. Such macromolecular fibrous elements can be woven (as in, for example, a mesh structure), or non-woven, and can, in some embodiments, serve as reinforcing materials of the hydrogel's fibrous network. Non-limiting examples of such macromolecules include polycaprolactone, gelatin, gelatin methacrylate, alginate, alginate methacrylate, chitosan, chitosan methacrylate, glycol chitosan, glycol chitosan methacrylate, hyaluronic acid (HA), HA methacrylate, and other non-crosslinked natural or synthetic polymeric chains and the likes.

In some embodiments, the hydrogel may contain additional elements which render it useful for specific applications, such as therapeutic and labeling agents, as these are discussed below, scaffold and other structural elements, live cells, cellular components and the like.

In some embodiments, the polymeric material, e.g., hydrogel further comprises one or more surfactants builders, thickeners and one or more enzymes.

In some embodiments, hydrogels may take a physical form that ranges from soft, brittle and weak to hard, elastic and tough material. Soft hydrogels may be characterized by rheological parameters including elastic and viscoelastic parameters, while hard hydrogels are more suitably characterized by tensile strength parameters, elastic, storage and loss moduli, as these terms are defined hereinabove or are known in the art.

In some embodiments, the term "thermoset" refers to a synthetic polymer that has been irreversibly cured by any technique, including curing by heating, by chemical reaction (e.g., as in epoxies) or irradiation. Examples of thermoset polymers include, without limitation, thermoset polyesters (e.g., as used in fiberglass), polyurethanes, vulcanized rubbers, phenol-formaldehydes (e.g., Bakelite® polymer), Duroplast, urea-formaldehydes (e.g., as used in plywood), melamine resins, epoxy resins, polyimides, cyanate esters and polycyanurates.

In some embodiments, the term "thermoplastic" refers to a polymer which is sufficiently soft above a certain temperature so as to readily allow plastic deformation of the polymer, and which is sufficiently stiff below a certain temperature so as to retain a desired shape. The softening of a thermoplastic polymer often occurs at temperatures near and/or above a transition temperature (e.g., a glass transition temperature, a melting point) of the polymer. Such a transition temperature may be determined, for example, by calorimetry.

The phrase "softening temperature", as used herein, refers to the lowest temperature among the glass transition temperature range of a thermoplastic polymer.

In some embodiments, a total concentration (also referred to as "% loading" or "% enrichment") of the proteins within the composite ranges from about 0.1 weight percent to about 10 weight percent of the total weight of the composite. In some embodiments, a total concentration of the proteins within the composite ranges from about 0.5 weight percent to about 3 weight percent.

In some embodiments, a total concentration of the proteins within the composite is e.g., about 0.1 weight percent, about 0.5 weight percent, about 1 weight percent, about 1.5 weight percent, about 2 weight percent, about 2.5 weight percent, about 3 weight percent, about 3.5 weight percent, about 4 weight percent, about 4.5 weight percent, about 5 weight percent, about 5.5 weight percent, about 6 weight percent, about 6.5 weight percent, about 7 weight percent, about 7.5 weight percent, about 8 weight percent, about 8.5 weight percent, about 9 weight percent, about 10 weight percent, about 20 weight percent, about 30 weight percent, about 40 weight percent, about 50 weight percent, including any value or range therebetween.

In some embodiments, the polymer comprises one or more additives other than the disclosed proteins. In some embodiments, the term "additive" may refer to a material which can be added to a polymeric material without being detrimental to its intended use. In some embodiments, the additives are selected from the group consisting of, and without being limited thereto, an antioxidant, a pigment, an antistatic additive, and a flame retarder. In some embodiments, additives are used to facilitate and/or control the loading of the mixture of protein therein/thereon. In some embodiments, the term "additive" refers to a surfactant or a dispersant.

In some embodiments, the enhancement of one or more mechanical properties as described hereinabove (e.g., Young's modulus, tensile strength, yield point, and stress at elongation) correlates with the total concentration of the proteins. The term "correlates" or "correlating" as used herein refers to an association between instances of two event, e.g., having a causal, complementary, parallel, or reciprocal relationship, between the % loading and the mechanical properties of the composite.

In some embodiments, the mixture of proteins and the polymer are substantially in a contiguous contact.

In some embodiments, the polymer is transparent and is thus suitable for use where vision is a requirement, e.g. vehicle windows, etc.

In some embodiments, the polymer is substantially a plate, whether curved, flat, comprising one or more substantially planar surfaces, or a combination thereof, e.g., so as to avoid formation of weak points, and/or allow substantially contiguous contact with the proteins.

In some embodiments, the mixture of proteins and the polymer are at least partially in a contiguous contact. In some embodiments, the mixture of proteins and the polymer are substantially in a contiguous contact.

In some embodiments, the disclosed mixture of proteins and/or the disclosed fiber derived from the mixture of proteins is defined as further comprising a linker. Such a linker may be a chemical moiety that serves to couple another agent, target moiety, or a surface while not adversely affecting either the targeting function, or targeting moiety.

In some embodiments, a plurality of the disclosed mixture of proteins and/or the disclosed fiber derived from the mixture of proteins are non-covalently attached to one another (e.g., by electrostatic bond).

In some embodiments, a plurality of the disclosed mixture of proteins and/or the disclosed fiber derived from the mixture of proteins are covalently cross-linked to one another. In some embodiments, the cross-linked form of the fiber is reversible (e.g. by heating).

In some embodiments, the covalent cross-linking is affected in vivo. Alternatively, the covalent cross-linking is affected ex vivo.

In some embodiments, the presence of covalent cross-linking is associated with a stronger mechanical property as described herein.

In some embodiments, the mixture of proteins is attached to or deposited on at least one surface of a polymer.

In some embodiments, the mixture of proteins is attached to or deposited on at least one surface of an inorganic substrate. Exemplary inorganic substrate substrates comprise one or more materials selected from, but not limited to, silicon, ceramics like alumina, titania, nickel, glass, nitinol etc.

In some embodiments, the mixture of proteins is attached to or deposited on at least one surface of the polymer via a linker. In some embodiments, the linker is an organic linker. In some embodiments, the linker is an inorganic linker. In one embodiment, the organic linker is a single, straight chain linker. In some embodiments, the linker may also include branched chains.

In some embodiments, the linker may also include non-cleavable cross linkers (e.g., comprising by disulfide bonds).

Additional exemplary Linkers may be water soluble agents including, without limitation, heterofunctional bridges such as 3-Aminopropyltriethoxysilane (APTES), NHS (N-hydroxysuccinimide), pegylated amino acid of the form carboxy-PEG-amine containing four or more polyethylene glycol units, and $BS^3$ (bis[sulfosuccinimidyl] suberate).

Additional exemplary Linkers may be water in-soluble agents including, without limitation, N'-Diisopropylcarbodiimide (DIC), Carbonyldiimidazole (CDI), 4-(Dimethylamino)pyridine (DMAP), Glutaraldehyde (GA).

In some embodiments, a linker functionalizes the fibers with other functional groups e.g., for further attachment or creating covalent bonds with the matrices of polymers tested.

In some embodiments, the term "linker" refers to a bond, e.g., a covalent bond. In one embodiment, the organic linker comprises reactive group that forms a part of the linker.

As used herein, the phrase "reactive group" describes a chemical group that is capable of undergoing a chemical reaction that typically leads to a bond formation. Chemical reactions that lead to a bond formation include, for example, nucleophilic and electrophilic substitutions, nucleophilic and electrophilic addition reactions, alkylations, addition-elimination reactions, cycloaddition reactions, rearrangement reactions and any other known organic reactions that involve a functional group, as well as combinations thereof.

The reactive group may optionally comprise a non-reactive portion (e.g., an alkyl) which may serve, for example, to attach a reactive portion of the reactive group to a moiety.

In exemplary embodiments, the linker comprises selected from a carbonyl group, amine, or sulfhydryl, or carboxylic group.

In some embodiments, the linker may create an intermediate group that facilitates other functional groups to act as a nucleophile group otherwise.

In some embodiments, the term "inorganic linker" refers to an inorganic binding entity, such as, without limitation, a silanol group.

In some embodiments, the composite is characterized by a thickness of e.g., 100 nm, 200 nm, 300 nm, 400 nm, 500 nm, 600 nm, 700 nm, 800 nm, 900 nm, 1 µm, 5 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 10 mm, 50 mm, 100 mm, including any value or range therebetween.

In some embodiments, the composite is characterized by a thickness of e.g., at least 100 nm, at least 200 nm, at least 300 nm, at least 400 nm, at least 500 nm, at least 600 nm, at least 700 nm, at least 800 nm, at least 900 nm, at least 1 µm, at least 5 µm, at least 10 µm, at least 20 µm, at least 30 µm, at least 40 µm, or at least 50 µm.

In some embodiments, the disclosed fibers are attached to a surface of a metal or to a polymeric material. In some embodiments, the disclosed fibers coat a metal or a polymeric material.

As used herein, the term "coat" is used to identify at least 10%, 20%, 30% 50, 60%, 70%, 80%, 90%, or 100% covering of an outer coated part (substrate).

In some embodiments, a coating process is applied to deposit the disclosed fiber on at least a portion of a surface of the substrate.

Non-limiting examples of coating method include dip coating, spray coating, brush coating, knife coating, roller coating, reel-to-reel coating, spin coating, print coating, screen printing and film casting. As further described in the Example section below, in some embodiment, the coating of the disclosed fiber on a metric (a stent) is applied by an electro spinning process.

The Articles

According to an aspect of some embodiments of the present invention there is provided an article (e.g., an article of manufacturing) comprising the composite described herein.

In some embodiments, the article is a medical device. In some embodiments, the phrase "medical device" refers to any device utilizable in treatment of a subject, preferably a human subject.

In some embodiments, the medical device is an implantable medical device. The medical device can be used for implantation, injection, or otherwise placed totally or partially within the body, and hence it is desirable that the device will be a drug-eluting device. In some embodiments, the medical device is for transdermal and/or topical applications in a subject. Such medical device should cause minimal tissue irritation when used to treat a given tissue and hence the inclusion of drugs therewith is beneficial. In some embodiments, the medical device is an implantable medical device, for being implanted in a bodily organ of a subject.

The phrase "implantable device" is used herein to describe any medical device that is suited for being placed within a bodily cavity for a prolonged (e.g., from a few hours, to a few years and even for lifetime) time period.

Exemplary non-limiting implantable devices include, a plate, a mesh, a screw, a pin, a tack, a rod, a suture anchor, aortic grafts, arterial tubing, artificial joints, blood oxygenator membranes, blood oxygenator tubing, bodily implants, catheters, dialysis membranes, drug delivery systems, endoprostheses, endotracheal tubes, guide wires, heart valves, intra-aortic balloons, pacemakers, pacemaker leads, stents, ultrafiltration membranes, vascular grafts, vascular tubing, venous tubing, wires, orthopedic implants, implantable diffusion pumps and injection ports.

Exemplary devices which can be used for transdermal application include, without limitation, a suture, an adhesive plaster and a skin patch. Further exemplary devices which can be used for topical application include, without limitation, a suture, an adhesive strip, a bandage, an adhesive plaster, a wound dressing and a skin patch.

Additional non-limiting exemplary devices include an anastomosis clip or plug, a dental implant or device, an aortic aneurysm graft device, an atrioventricular shunt, a hemodialysis catheter, a bone-fracture healing device, a bone replacement device, a joint replacement device, a tissue regeneration device, a hemodialysis graft, an indwelling arterial catheter, an indwelling venous catheter, a needle, a septal closure device, a stent e.g., vascular stent, a tracheal stent, an esophageal stent, a urethral stent, a rectal stent, a stent graft, a suture, a thread, a tube, a vascular aneurysm occluder, a vascular clip, a vascular prosthetic filter, a vascular sheath and a drug delivery port, a venous valve and a wire.

Examples of bodily sites where a medical device can be implanted include, without limitation, skin, scalp, hair, a dermal layer, an eye, an ear, a small intestines tissue, a large intestines tissue, a kidney, a pancreas, a liver, a digestive tract tissue or cavity, a respiratory tract tissue or cavity, a bone, a joint, a bone marrow tissue, a brain tissue or cavity, a mucosal membrane, a nasal membrane, the blood system, a blood vessel, a muscle, a pulmonary tissue or cavity, an abdominal tissue or cavity, an artery, a vein, a capillary, a heart, a heart cavity, a male reproductive organ, a female reproductive organ and a visceral organ.

As noted hereinabove, in some embodiments, the implantable medical device is a stent. The stent can be of various types, shapes and materials. Any commercially available stent, presently or in the future, can be used according to embodiments of the invention.

In some embodiments, the implantable medical device is an artificial vascular graft. In some embodiments, the implantable medical device is an artificial heart pump diaphragm, implantable heart valve leaflets. In some embodiments, the implantable medical device is a tissue scaffold.

In some embodiments, the implantable medical device is an orthopedic implant. In some embodiments, the implantable medical device is selected from, without being limited thereto, dental implant, cavity filling, and orthodontic device.

The composites of the invention and articles comprising same may be further used for protection from a kinetic threat. The article may have a shape selected from, without being limited thereto, an armor sheet, a bullet-proof vest, a body armor, a door panel, a floor panel, a wall panel, a reinforced window, a tube, a helmet, glass, a seat, an aircraft, an armored vehicle, and a motor vehicle. For example, the article is useful for protecting an object from a kinetic threat. That the, the disclosed composite (and/or article comprising the same) may provide protection from multiple hits of kinetic threats such as rifle bullets. The method of protecting an object from a kinetic threats comprising providing the object with the article described herein, i.e., comprising the composite as described above.

In some embodiments, the article is selected from the group consisting of: a pill, a tablet, a capsule, and a gel-cap. Other non-limiting examples of articles according to the invention include medical adhesive strips, skin grafts, replacement ligaments, and surgical mesh; and in a wide range of industrial and commercial products, such as clothing fabric, bullet-proof vest lining, container fabric, bag or purse straps, cable, rope, fishing line, adhesive binding material, non-adhesive binding material, strapping material, automotive covers and parts, aircraft construction material, weatherproofing material, flexible partition material, sports equipment; and, in fact, in nearly any use of fiber or fabric for which high tensile strength and elasticity are desired characteristics. Adaptability and use of the stable fiber product in other forms, such as a dry spray coating, bead-like particles, or use in a mixture with other compositions is also contemplated by the present invention.

In some embodiments, the article is stable in a physiological condition as described hereinabove (e.g., being biostable).

In some embodiments, the article comprises a fabric. In some embodiments, the term "fabric" refers to a woven or non-woven artifact made of the protein fiber of the invention. Optionally, the fabric is made with a controlled shape, dimension, porosity and/or pore size.

In some embodiments, the article is characterized by a thermal insulation. In some embodiments, the article is composed of rigid, polyurethane plastic material having a high degree of thermal resistance and therefore acting as thermal insulation. The use of this material as thermal insulation is known in the art, as in the thermal insulation included in refrigerated appliances and vehicles.

In yet further embodiments, the disclosed article or composite may be a cosmetic composition. The term "cosmetic composition" relates to a composition having beneficial skin or other superficial tissue esthetic properties, such as improving or enhancing skin tone and color, strengthening keratin structures, improving hair and nails and eye lashes smoothness, thickness, hair color and shine, hair straightening, hiding superficial tissue imperfections such as blemishes and scars, or preventing future or cumulative damage such as sunlight damage and skin aging. Herein by "improving" it is also meant to include strengthening, coloring, lengthening, and thickening.

Dermatological or cosmetic compositions for the treatment according to the invention are applied topically on the epidermis as ointment pomades, lotions, creams and gels, and on mucous membranes as water emulsions such as creams, lotions or gels. The cosmetic products may be produced using such a composition include products such as shaving cream, hand cream, shampoo, soap, conditioner, body cream, sun skin-protection, face cream, or body lotion. The ratio of components in the cosmetic composition may be adjusted according to the intended application of the cosmetic composition.

Further articles are selected from, but are not limited to, additive for 3D printing materials, such as ink related materials, thermoplastic polymers for FDM (Fused Deposition Modeling) and polymer powders for SLS (Selective laser sintering), diaphragms of loudspeakers, filters, and strings.

The Process

The present invention also provides a process of making the disclosed composite, comprising the step of attaching the mixture of proteins to the polymer, so as to form the composite.

In some embodiments, the process comprises a step of melting the polymer to yield a molten polymer and transforming the mixture of proteins into the molten polymer. Generally, transforming the molten polymer into a final form includes cooling the molten polymer, so that the desired structure of polymer-proteins composite or matrix is formed.

Exemplary methods for shaping the composite into the desired shape include methods known in the art of polymers such as molding, injection molding, compression molding and extrusion of the molten polymer.

In some embodiments, attaching the mixture of proteins to the polymer includes contacting the mixture of proteins with the polymer so as to cause the mixture of proteins to adhere to the polymer e.g., by compounding, as described in the Examples section below. Such embodiments are useful when the two components (i.e. the polymer and the mixture of proteins) are mutually adherent, or for example, when localized melting of only the contact surface of the polymer yields a sufficiently tenacious attachment of the proteins and the polymer, to yield e.g., a unitary composite.

In some embodiments, attaching the polymer and the mixture of proteins includes transforming of the proteins into the molten polymer and maintaining contact of the polymer and the mixture of proteins. In some embodiments, the polymer is placed inside a mold or the molten polymer is placed for molding.

In some embodiments, attaching the polymer and the mixture of proteins includes using at least one adhesive (e.g., a thermosetting resin (polymer) or a thermoplastic resin as discussed hereinabove) to assist attaching the polymer to the mixture of proteins. In some embodiments, using an adhesive includes applying the adhesive, for example by spraying the adhesive, painting the adhesive, brushing the adhesive, depositing the adhesive, pouring the adhesive or laying a sheet of adhesive onto one or both of the two components. In some embodiments, the two components are subsequently brought together and held tightly in place, typically but not exclusively with heating, until the adhesive sets.

In some embodiments, an adhesion promoter is applied to the contact surface of the polymer so as to increase the tenacity of adhesion of the adhesive to the polymer. In some embodiments, the polymer includes at least one adhesion promoter. In some embodiments, the mixture of proteins includes one or more adhesion promoters. In an embodiment, at least one adhesion promoter is added to the molten polymer. In an embodiment of the present invention, at least one adhesion promoter is added to the adhesive. In some embodiments, the polymer includes at least one impact modifier. In some embodiments, the mixture of proteins includes at least one impact modifier. In some embodiments, at least one impact modifier is added to the molten polymer. In some embodiments, the step of attaching the mixture of proteins to the polymer comprises dissolving the polymer to yield a dissolved polymer and transforming the mixture of proteins into the dissolved polymer.

In some embodiments, the process is affected by dissolving the polymer e.g., in an aqueous solution or an organic solution (or solvent) and contacting the proteins with the solution in which the polymer is dissolved, followed by solvent evaporation in order to create the final product, (referred to as "solvent casting"). In some embodiments, the process is followed by the melt extrusion.

In some embodiments, the mixture of proteins is dissolved e.g., in a water-miscible solvent, prior to contacting the plurality of peptides with the polymer and the aqueous solution.

In some embodiments, the polymer, or the polymer and the mixture of proteins, are electrospun. Electrospinning is known to be suitable for fabrication various types of polymeric structures such as, without limitation, nano- and micro-wires. One advantage of the electrospinning process for fabricating the composite of the present embodiments is that such production process can be executed in relatively low temperatures, thus enabling to incorporate the mixture of proteins in an early stage of the process. Another advantage is that the electrospun polymer is capable of carrying a relatively high amount of the mixture of proteins.

A further advantage of the present embodiments is that the electrospinning process can provide the electrospun polymer, hence also the composite of the present embodiments, with enhanced mechanical properties far exceeding the mechanical properties of traditional composites.

The mechanical properties depend on several variants, which may be controlled during the manufacturing process. One variant is the chemical nature of the polymer. This variant may be controlled by a suitable choice of the polymer(s) used in e.g., the electrospinning process. Another variant is the area of contact between the body fluids and the electrospun polymer, which can be controlled, for example, by varying the free surface of the electrospun polymer fibers.

The electrospinning process parameters, e.g., voltage, injection speed and collector speed, may allow controlling the feature of the end products which may be tailored according to demand. The electrospinning process may also be used for coating medical device (e.g., catheter) that were mentioned before. It is to be understood that various coating methods may be utilized to produce the disclosed fibers including, without limitation, spin coating, wet-spinning, dry-spinning, and gel-spinning.

Cell Growth and Culture

In one embodiment, fibers, a mixture of proteins, "m" types of proteins or any combination thereof with or without a polymer is/are used as an implantable or biocompatible material or together with an implantable or biocompatible material. In one embodiment, fibers, a mixture of proteins, "m" types of proteins or any combination thereof with or without a polymer is/are used for cell propagation. In one embodiment, fibers, a mixture of proteins, "m" types of proteins or any combination thereof with or without a polymer is/are used for maintaining, preserving and/or inducing cell viability. In one embodiment, fibers, a mixture of proteins, "m" types of proteins or any combination thereof with or without a polymer is/are used for reducing and/or minimizing cell death. In one embodiment, fibers, a mixture of proteins, "m" types of proteins or any combination thereof with or without a polymer is/are used for inducing cell migration. In one embodiment, fibers, a mixture of proteins, "m" types of proteins or any combination thereof with or without a polymer is/are used for inducing cell attachment. In one embodiment, a tissue scaffold comprises fibers, a mixture of proteins, "m" types of proteins or any combination thereof with or without a polymer. In one embodiment, fibers are fibers as described herein.

In one embodiment, provided herein a composition comprising a biocompatible material and fibers, a mixture of proteins, "m" types of proteins or any combination thereof with or without a polymer. In one embodiment, a biocompatible material is a living body implantable material. In one embodiment, a biocompatible material is a material adapted to contact cells or tissues. In one embodiment, a biocompatible material is a material which promotes the viability of cells or tissues.

In one embodiment, fibers, a mixture of proteins, "m" types of proteins or any combination thereof with or without a polymer is/are used for inducing bone regeneration. In one embodiment, a bone regeneration composition or scaffold comprises fibers, a mixture of proteins, "m" types of proteins or any combination thereof with or without a polymer. In one embodiment, provided herein a composition comprising: (1) cells; and (2) fibers, a mixture of proteins, "m" types of proteins or any combination thereof with or without a polymer. In one embodiment, provided herein a composition comprising: (1) cell-culture media; and (2) fibers, a mixture of proteins, "m" types of proteins or any combination thereof with or without a polymer. In one embodiment, provided herein a composition comprising: (1) an abiotic material; and (2) fibers, a mixture of proteins, "m" types of proteins or any combination thereof with or without a polymer.

In one embodiment, provided herein a wound healing composition comprising: fibers, a mixture of proteins, "m" types of proteins or any combination thereof with or without a polymer. In one embodiment, provided herein a pharmaceutical composition comprising: fibers, a mixture of proteins, "m" types of proteins or any combination thereof with or without a polymer.

In one embodiment, provided herein a medical device adapted to contact a bodily tissue, comprising: fibers, a mixture of proteins, "m" types of proteins or any combination thereof with or without a polymer. In one embodiment, provided herein a medical device adapted to hold body tissues together after an injury or surgery, comprising: fibers, a mixture of proteins, "m" types of proteins or any combination thereof with or without a polymer. In one embodiment, provided herein a surgical suture comprising: fibers, a mixture of proteins, "m" types of proteins or any combination thereof with or without a polymer. In one embodiment, provided herein a surgical suture coated with: fibers, a mixture of proteins, "m" types of proteins or any combination thereof with or without a polymer. In one embodiment, provided herein a wound care dressing comprising: fibers, a mixture of proteins, "m" types of proteins or any combination thereof with or without a polymer. In one embodiment, provided herein a sterile pad or compress comprising: fibers, a mixture of proteins, "m" types of proteins or any combination thereof with or without a polymer.

In one embodiment, provided herein a composition comprising: (1) cells, cell media or both; and (2) fibers, a mixture of proteins, "m" types of proteins or any combination thereof with or without a polymer. In one embodiment, provided herein a method for maintaining or growing cells comprising contacting the cells with a composition comprising: fibers, a mixture of proteins, "m" types of proteins or any combination thereof with or without a polymer. In one embodiment, provided herein a method for assembling a multi-layer cell culture, comprising contacting the cells with a composition comprising: fibers, a mixture of proteins, "m" types of proteins or any combination thereof with or without a polymer. In one embodiment, provided herein a method for assembling a multi-layer cell culture, comprising contacting the cells with a surface comprising: fibers, a mixture of proteins, "m" types of proteins or any combination thereof with or without a polymer.

In one embodiment, provided herein a method for assembling pre-defined number of cell layers comprising contacting the cells with a surface comprising: a pre-defined amount of: fibers, a mixture of proteins, "m" types of proteins or any combination thereof with or without a polymer. In one embodiment, a pre-defined amount of: fibers, a mixture of proteins, "m" types of proteins or any combination thereof with or without a polymer is a pre-defined thickness of a surface adapted to contact cells. In one embodiment, cells within a composition or a method as described herein cross-interact in 3D. In one embodiment, provided herein a method for fabrication of a set number of layers of cells wherein the cells cross interact. In one embodiment, provided herein is a method for fabrication of a set number of layers of cells wherein the cells cross interact and are bound to the fibers.

In one embodiment, "pre-defined number of cell layers" or "a set number of layers of cells" is determined per the amount of: fibers, a mixture of proteins, "m" types of proteins or any combination thereof with or without a polymer applied on a cell-growing surface such as but not limited to a cell growing plate or a cell growing dish. One embodiment, "pre-defined number of cell layers" or "a set number of layers of cells" is determined per the amount of: fibers, a mixture of proteins, "m" types of proteins or any combination thereof with or without a polymer applied on a cell-growing surface such as a biocompatible material.

In one embodiment, according to the methods and compositions as described herein $1 \times 10^3$ fibers/cm$^2$ to $8 \times 10^5$ fibers/cm$^2$ maintains only a single cell layer on at least 70% or 80% of a surface coated with fibers, a mixture of proteins, "m" types of proteins or any combination thereof with or without a polymer. In one embodiment, according to the methods and compositions as described herein $1 \times 10^2$ fibers/cm$^2$ to $1 \times 10^6$ fibers/cm$^2$ maintains only a single cell layer on at least 70% or 80% of a surface coated with fibers, a mixture of proteins, "m" types of proteins or any combination thereof with or without a polymer. In one embodiment, according to the methods and compositions as described herein $4 \times 10^5$ fibers/cm$^2$ to $18 \times 10^5$ fibers/cm$^2$ maintains a two cell layers on at least 70% or 80% of a surface coated with fibers, a mixture of proteins, "m" types of proteins or any combination thereof with or without a polymer. In one embodiment, according to the methods and compositions as described herein $8 \times 10^5$ fibers/cm$^2$ to $14 \times 10^5$ fibers/cm$^2$ maintains a two cell layers on at least 70% or 80% of a surface coated with fibers, a mixture of proteins, "m" types of proteins or any combination thereof with or without a polymer. In one embodiment, according to the methods and compositions as described herein $10 \times 10^5$ fibers/cm$^2$ to $14 \times 10^5$ fibers/cm$^2$ maintains a two cell layers on at least 70% or 80% of a surface coated with fibers, a mixture of proteins, "m" types of proteins or any combination thereof with or without a polymer. In one embodiment, according to the methods and compositions as described herein $15 \times 10^5$ fibers/cm$^2$ or more maintains three or more cell layers on at least 70% or 80% of a surface coated with fibers, a mixture of proteins, "m" types of proteins or any combination thereof with or without a polymer. In one embodiment, according to the methods and compositions as described herein $18 \times 10^5$ fibers/cm$^2$ or more maintains three or more cell layers on at least 70% or 80% of a surface coated with fibers, a mixture of proteins, "m" types of proteins or any combination thereof with or without a polymer. In one embodiment, according to the methods and compositions as described herein $20 \times 10^5$ fibers/cm$^2$ or more maintains three or more cell layers on at least 70% or 80% of a surface coated with fibers, a mixture of proteins, "m" types of proteins or any combination thereof with or without a polymer. In one embodiment, according to the methods and compositions as described herein $24 \times 10^5$ fibers/cm$^2$ or more maintains three or more cell layers on at least 70% or 80% of a surface coated with fibers, a mixture of proteins, "m" types of proteins or any combination thereof with or without a polymer. In one embodiment, multilayer, multi-cell layers or more than two layers of cells result in a 3D cell-to-cell interaction within each layer. In one embodiment, multi-layer, multi-cell layers or more than two layers of cells result in a 3D cell-to-cell interaction within each layer and between the layers.

In one embodiment, SS mechanically protects cells. In one embodiment, SS provides mechanical protection to cells bound to the SS. In one embodiment, SS provides mechanical protection to cells encapsulated with the SS.

In one embodiment, multilayer, multi-cell layers or more than two layers of cells result in a 3D cell-to-cell interaction and 3D cell-to-SS interaction within each layer. In one embodiment, multilayer, multi-cell layers or more than two layers of cells result in a 3D cell-to-cell interaction and 3D cell-to-SS interaction within each layer.

In one embodiment, provided herein a raft composed of: (1) fibers, a mixture of proteins, "m" types of proteins or any combination thereof with or without a polymer; (2) cells adhered to the raft. In one embodiment, provided herein a raft composed of: (1) fibers, a mixture of proteins, "m" types of proteins or any combination thereof with or without a polymer; (2) solitary cells adhered to the raft. In one embodiment, the raft encapsulates the cells. In one embodiment, the cells are attached to the raft.

In one embodiment, provided herein a method for growing, maintaining or expanding solitary cells, comprising mixing the cells with fibers, a mixture of proteins, "m" types of proteins or any combination thereof with or without a polymer. In one embodiment, provided herein a method for growing, maintaining or expanding solitary cells which require cell surface attachment, comprising mixing the cells with fibers, a mixture of proteins, "m" types of proteins or any combination thereof with or without a polymer. In one embodiment, a method for growing, maintaining or expanding solitary cells is an in-vitro method.

In some embodiments, fibers, a mixture of proteins, "m" types of proteins or any combination require at least 6 repeats (n). In some embodiments, fibers, a mixture of proteins, "m" types of proteins or any combination thereof require at least 7 repeats. In some embodiments, fibers, a mixture of proteins, "m" types of proteins or any combination thereof as described herein require at least 8 repeats. In some embodiments, fibers, a mixture of proteins, "m" types of proteins or any combination thereof as described herein require: 6-70, 7, 8-70, 9-70, 10-70, 11-70, 12-70, 13-70, 14-70, 15-70, 16-70, 17-70, 18-70, 19-70, or 20-70 repeats ("n" as defined hereinabove).

In one embodiment, a method as described herein is an in-vitro method. In one embodiment, a method as described herein is an ex-vivo method.

General

As used herein the term "about" refers to ±10%. The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments. The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find support in the following examples.

EXAMPLES

Materials and Methods

Plasmids: DNA sequence in a PCR-ScriptAmpSK(+) plasmid obtained from Geneart (Regensburg, Germany). pFastBacHTa obtained from Invitrogen.

Restriction Enzymes: PstI, HindIII, NsiI, obtained from (New England Biolabs, MA, USA).

Transfection and Transformation: Competent *E. coli* DH10BAC cells, containing bacmid and a helper plasmid (Invitrogen). ESCORT transfection reagent (Sigma-Aldrich).

Media: ESF 921 Insect cell culture medium, Serum free, obtained from Expression Systems, or SF-900 II SFM; Serum free, obtained from GIBCO; Propidium Iodid (SIGMA, ISRAEL); Calcein AM (Cayman, USA); and DAPI (ibidi, Germany).

Imaging: Inverse phase contrast microscope, EVOS XL, Life Technologies. For confocal pictures: Olympus BX51 fluorescence microscope. Magnafire SP camera was from Optronics.

Experimental Procedures for Forming the Protein Mixtures:

Synthesis of a Sequence Encoding for a Single Repeat Unit of a Dragline Spider Silk Protein: A 35 amino acid long sequence representing an average consensus sequence of the 15 repeats constituting the repetitive region of ADF-4 (Genbank entry U47856) was designed. The average consensus sequence peptide sequence is: SGPGGYGPGSQGPSGPG-GYGPGGPGSSAAAAAAAA (SEQ ID NO. 14), which is encoded by the 105 DNA base pair sequence: 5'-TCTGGTCCTGGAGGTTATGGCCCAGGAAGCCAA-GGACCATCTGGTCCAGGAGGATAT GGTCCAGGCG-GACCTGGCTCTAGTGCAGCAGCTGCCGCAGCAGC-TGCA-3' (SEQ ID NO: 15). The above synthetic DNA was obtained in a PCR-ScriptAmpSK(+) plasmid. The sequence was optimized for expression according to the codon usage of *Spodoptera frugiperda*, cells of which are used for the synthesis of the spider silk proteins and fibers.

Donor Plasmid Construction: The ScriptAmpSK(+) plasmid was excised with Xba I and Xho I, and a 136-bp sequence containing the basic repeat sequence flanked with Nsi I and Pst I restriction sites was isolated and cloned into the multiple cloning site (MCS) of the baculoviral donor plasmid pFastBacHTa. Thus, the basic donor plasmid coding for an artificial 49 amino acid N-terminal domain and a 35 amino acid core domain was generated.

Multimerization of the Single Repeat: The basic module coding for one repeat (monomer) of spider silk protein is flanked by the restriction enzymes sites NsiI and PstI, which are compatible. In the first step the monomer is released by double restriction and is inserted in frame into the same donor plasmid cut with PstI. Only if the insert is ligated in the correct sense orientation will a double cut release a dimer [the restriction site between the two repeats was eliminated upon ligation]. In a second step the dimer was released and then reinserted in the same fashion to obtain a vector with four repeats. In following steps, this procedure was reiterated to obtain a donor plasmid containing multiple synthetic repeats. Constraints resulting from the molecular biology tools employed and the repetitive nature of the sequence limit the maximum achievable number of identical repeats.

Ligation of the Native C-Terminal Domain Downstream to the Synthetic Repeats: Insertion of the C-terminal domain of ADF4 114 amino acids took place using PCR with the following primers: A sense primer having the sequence 5'-ATATGCTGCAGGCCCTAGTGGTCCTGGA-3' (SEQ ID NO: 16) containing a PstI restriction site (underlined) and an anti-sense primer having the sequence 5'-TCGACAAGCTTGGTACCGCA-3' (SEQ ID NO: 17) coding for a 3' HindIII restriction site (underlined). The donor plasmid vectors with different number of repeats and the PCR product were excised with PstI and HindIII, purified and ligated, resulting in a pFastBacHTa donor plasmid coding for a His6 tag which is part of an artificial N terminal domain, followed by a varied number of identical repeats (the inventors obtained constructs containing 1, 2, 4, 8, 12, 16, 20, 24, 32 repeats of the nucleic acid sequence) and the native C terminal domain.

Cell Culture: Sf9 cells were propagated at 27° C. in ESF 921 serum-free insect cell culture medium. Sf9 cells were grown either as monolayers on cover slips in 6 well plates or in shaker flasks agitated at 130 rpm.

Production of Recombinant Baculovirus: Competent *E. coli* DH10BAC cells, containing bacmid (baculovirus shuttle vector plasmid) and a helper plasmid, were used to generate recombinant bacmids according to the manufacturer's protocol (Invitrogen). Insertion of the gene into the bacmid was verified by PCR. Sf9 cells were transfected with recombinant bacmid DNA using ESCORT transfection reagent in 6-well plates. The cells were incubated for 5 h at 27° C., rinsed and incubated for another 72 h. Media were harvested, centrifuged, and the virus containing supernatant was used for 2-3 successive infections resulting in amplification of the virion titer.

Expression of Synthetic ADF-4 Based Proteins: Sf9 cells ($3*10^6$ cells/ml) were infected with the recombinant viruses at various MOIs (multiplicity of infection) ranging from 0.1 to 10. Four days post infection cells were harvested by centrifugation at 16000 g for 10 min.

Property enrichment of polymers: In the process of product development several potential materials were tested for properties enrichment with the disclosed Spider silk. The aim is to enrich certain material properties to answer industry needs and difficulties, i.e. higher toughness, higher impact resistance, higher fracture toughness and higher stress and modulus.

A variety of materials with different applications ranging from epoxy resins were used for composite materials, thermoplastic polymers and thermoset polyurethane sheets and films and biocompatible hydrogels including pHEMA, inkjet materials for 3D printing industry.

List of Tested Materials:
 1. Epoxy Resins: (a) EP-520 by Polymer Gvulot; and (b) EP-502 by Polymer Gvulot
 2. Thermoplastic polyurethanes (TPU): (a) Tecoflex®SG-93A by Lubrizol; (b) EG-72 by Lubrizol; and (c) PE399 by Huntsmann
 3. Thermoset polyurethanes (PU): (a) −2047 by Polymer Gvulot
 4. Nylon 12 in the form of pallets supplied by PolyRam
 5. Nylon 12 in the form of powder supplied by ARAN
 6. pHEMA supplied by Sigma Aldrich
 7. Butvar (B-98) supplied by Sigma Aldrich
 8. EVOH (EVAL F101B) supplied by Kuraray
 9. PLA (2003D) supplied by NatureWorks LLC.
 10. PCL (CAPA 80) supplied by CAPA 80 Perstorp
 11. PCL (80 Mn) supplied by Sigma Aldrich
 12. Silicon—Sylgard 184 supplied by Dow Corning
 13. VeroClear—Acrylic UV-cured inkjet supplied by Stratasys Several processing techniques for sample preparation and analysis were tested, including: solvent casting, mold casting, solvent electro-spinning and melt compounding.

Example 1

Composites Comprising Epoxy Resins

Dual component systems were tested as matrices for composite materials. The aim is to improve matrix properties to allow for better mechanical properties for the whole system. A custom-made PTFE molds were used for material preparation.

Experimental for Epoxy Based Dual Component Systems:

In exemplary procedures, part A—resin base and B—hardener were weighed according to manufacturer's recommendations. Spidersilk ("SS", also referred to herein throughout as "SSS") fibers were weighed in different loading percentages of 0, 1% and 2% w/w and poured into the molds. Curing profile was 24 h at room temperature followed by 3 h at 80° C. Specimens were removed from the mold and were tested for mechanical properties by tensile tester for the sample tensile strength, modulus, strain and work to failure energy. Each test set consisted of 5-6 specimens to establish statistical data.

Figure 2:
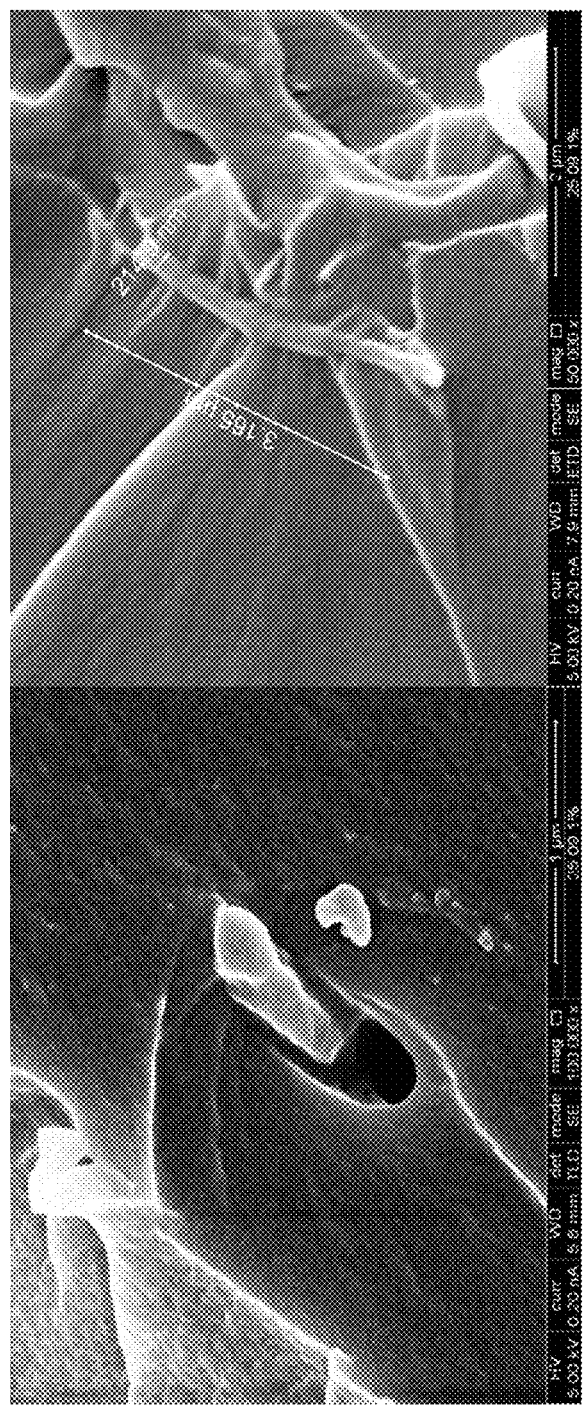
FIG. 2 presents scanning electron microscope (SEM) images showing adherence of the disclosed protein fibers onto EP-520 (at 2% enrichment). The adhesion of the fibers seems to create cavities on the polymer (left panel), while in some cases a better adhesion with no cavities around the fibers was observed (right panel, showing adhered fibers having 3.165 μm length and diameter of about 215 nm).

Epoxy—EP-520 by Polymer Gvulot: The Young modulus was improved (increased) in about 10% (FIG. 1). Adhesion of fibers-matrix seems to be poor (as shown in SEM images of FIG. 2 left panel). Although in some cases a better adhesion with no cavities around the fibers was detected (FIG. 2 right panel: showing SS fiber having a length of 3.165 µm and a diameter of about 215 nm).

The measurements were done by FEI microscope at different resolutions and at different electron acceleration speeds from 10-30 keV, HRSEM mode was used for better visualization and measurements of fiber length and diameter.

Figure 3:
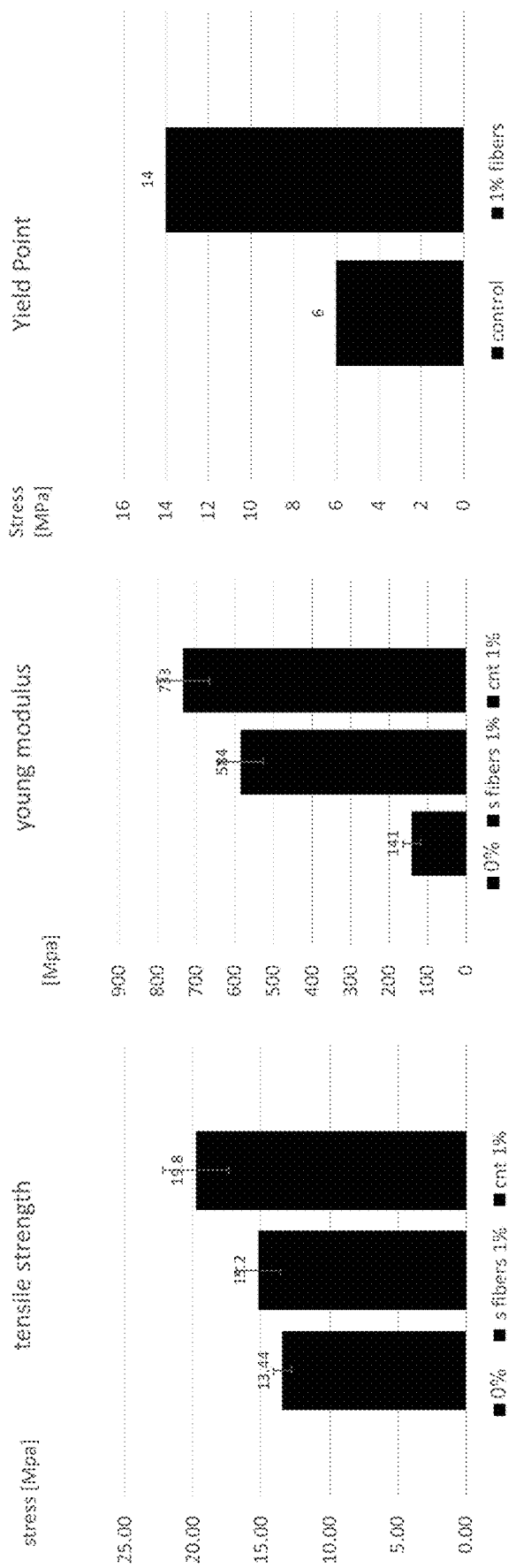
FIG. 3 presents bar graphs showing the tensile strength (left panel), Young's modulus (middle panel), and strain at break (right panel) of Epoxy—EP-502, having 1% concentrations (wt.) of protein enrichment comparing to controls (no enrichment or carbon nanotube (CNT) enrichment).

Epoxy—EP-502: The results of the mechanical tests (tensile strength, Young modulus, and Yield point; 1% enrichment with SS), are shown in FIG. 3 (also compared to 1% CNT enrichment, and summarized in Table 1 hereinbelow.

TABLE 1

| Young's Modulus improvement [%] | 314% |
|---|---|
| Tensile Strength improvement [%] | 47% |
| Yield Point improvement [%] | 133% |

Bending results: In additional exemplary procedures, the bending experiments were tested on control and 1% enriched samples.

Specimen type dimensions were 63.5*12.7*13.1 mm.

The results are summarized in Table 24 below, showing, inter alia, an enhanced Young's Modulus of bending, and a reduced work of failure of the 1% enriched specimens.

TABLE 2

| | Young's Modulus of Bending (MPa) Control | Young's Modulus of Bending (MPa) 1% SS | | Maximum Bending Stress (MPa) Control | Maximum Bending Stress (MPa) 1% SS |
|---|---|---|---|---|---|
| mean | 2943.98 | 3271 | mean | 111.40 | 73.33 |
| SD | 177.08 | 160.49 | SD | 5.64 | 1.44 |
| variance [%] | 6.01% | 5% | variance [%] | 5.06% | 1.96% |

| | Maximum Strain at break Control | Maximum Strain at break 1% SS | | Work of Failure (Nmm) Control | Work of Failure (Nmm) 1% SS |
|---|---|---|---|---|---|
| mean | 0.09 | 0.03 | mean | 1164.98 | 186.43 |
| SD | 0.00 | 0.00 | SD | 136.69 | 14.99 |
| variance [%] | 4.28% | 8.41% | variance [%] | 11.73% | 8.04% |

Example 2

Composites Comprising Thermoplastic and Thermoset Polyurethanes (Pu)

Several polyurethanes were tested. The improvements in tear resistance and tensile strength were evaluated. Thermoset PU were mainly a two-component system, while thermoplastic PUs were supplied in sheet form or pellets and dissolved in an organic solvent to which SS fibers were added. Solutions were mold casted and allowed to evaporate.

Exemplary Experimental Procedures for Thermoplastic Polymers:

The supplied sheets were dissolved in several organic solvents to test for dissolution rate. The dissolution also affected the final mechanical properties produced from the final specimens. The preparation method was uniform for all the samples.

Pe-399 from HUNTSMAN (aliphatic polyurethane polymer) was dissolved 10% by weight in 1,4 Dioxane then left to evaporate for 24 hours. After the evaporation ended the film was cut to strips of 8 mm width and 80 mm length and stretched by tensile tester. Tensile test according to ASTM D-882. Sample dimensions were strips of 7 cm length & 0.8 cm width.

Figure 4A:
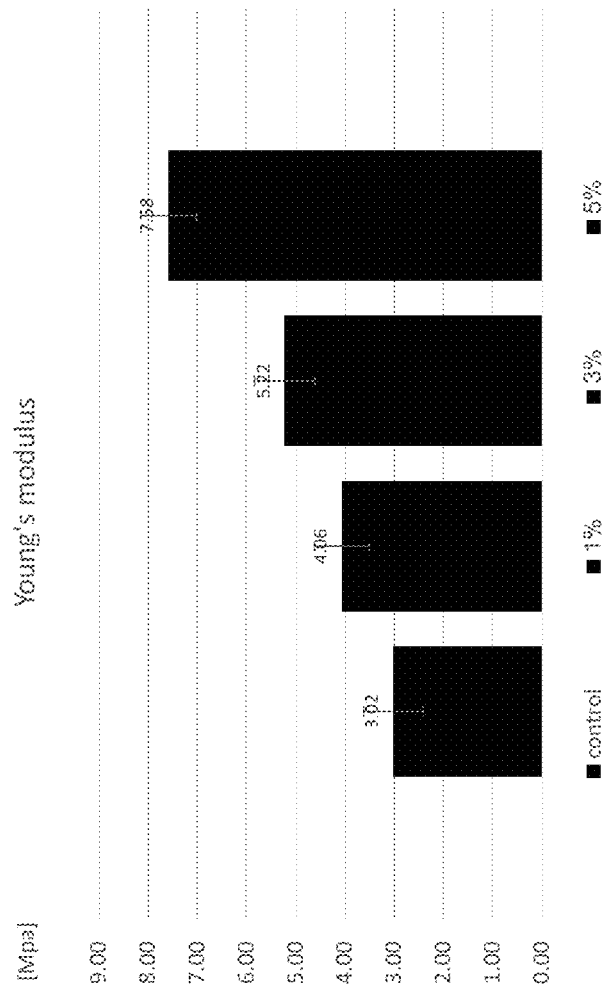
FIGS. 4A-E presents tensile test results including Young's modulus (FIG. 4A), Stress at 30% elongation (FIG. 4B) and toughness at 30% elongation (FIG. 4C), stress at 100% elongation (FIG. 4D) and the toughness at 100% elongation for thermoset PU (FIG. 4E). All performed on control and SS enriched films, as indicated in the inset of each graph (from left to right). Results are presented as mean±SD (n=5 different strips from the same film, for each condition).
Figure 4B:
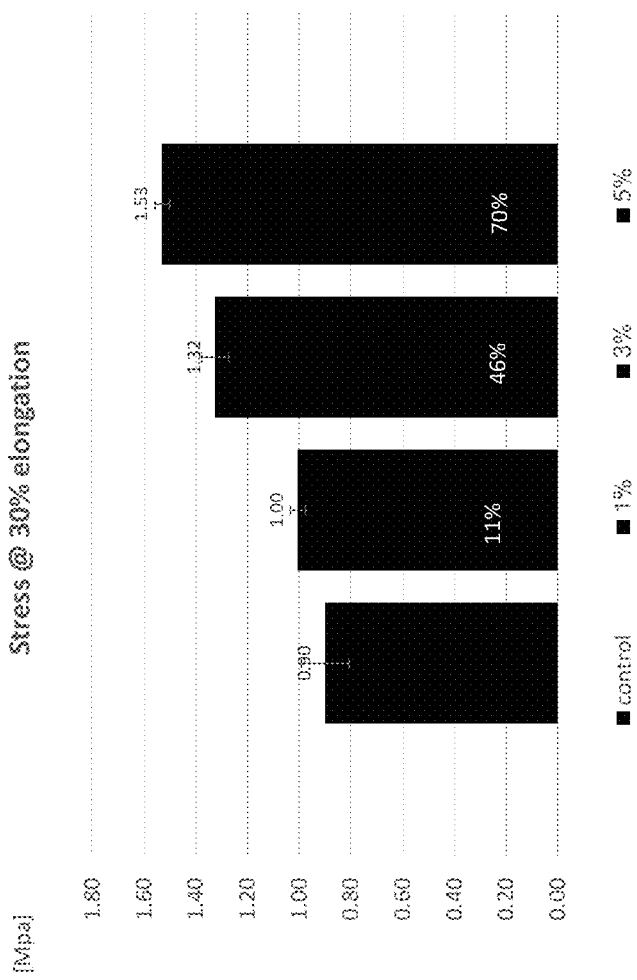
Figure 4C:
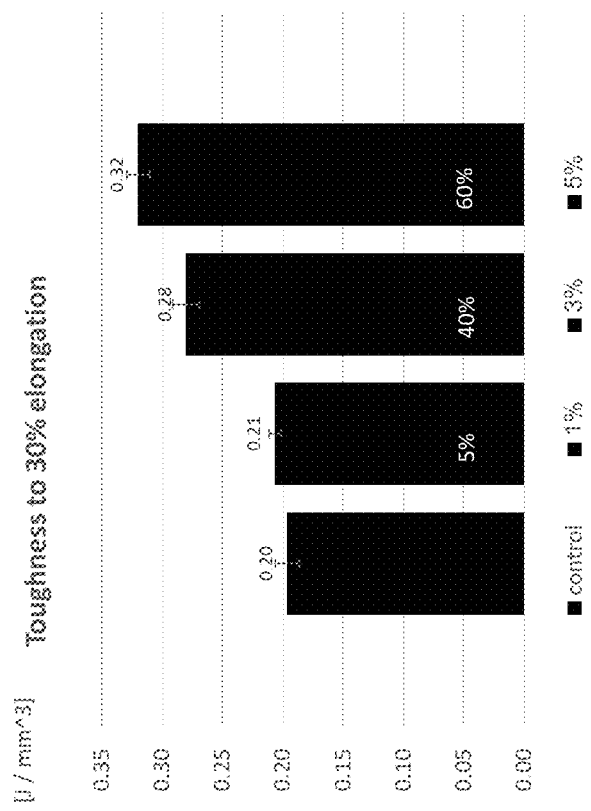
Figure 4D:
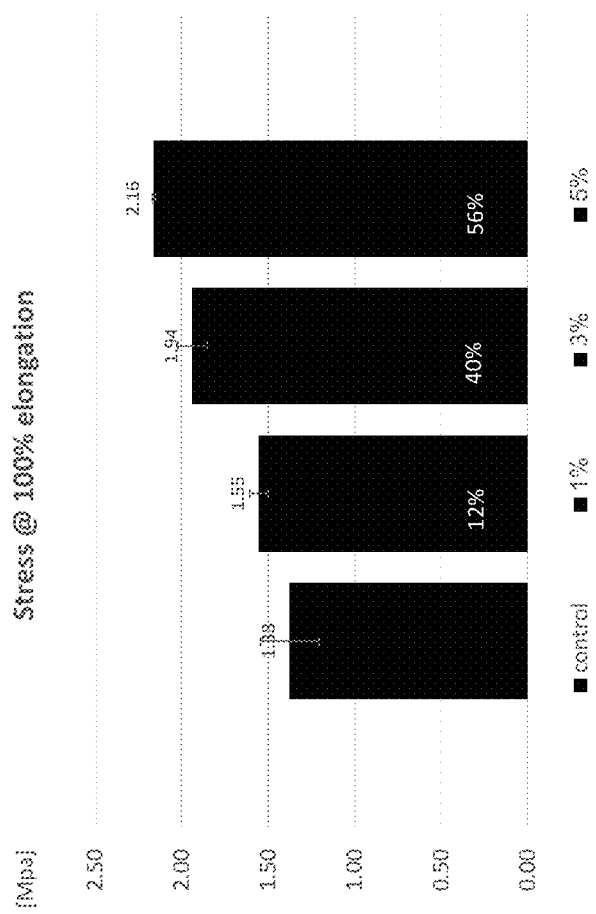
Figure 4E:
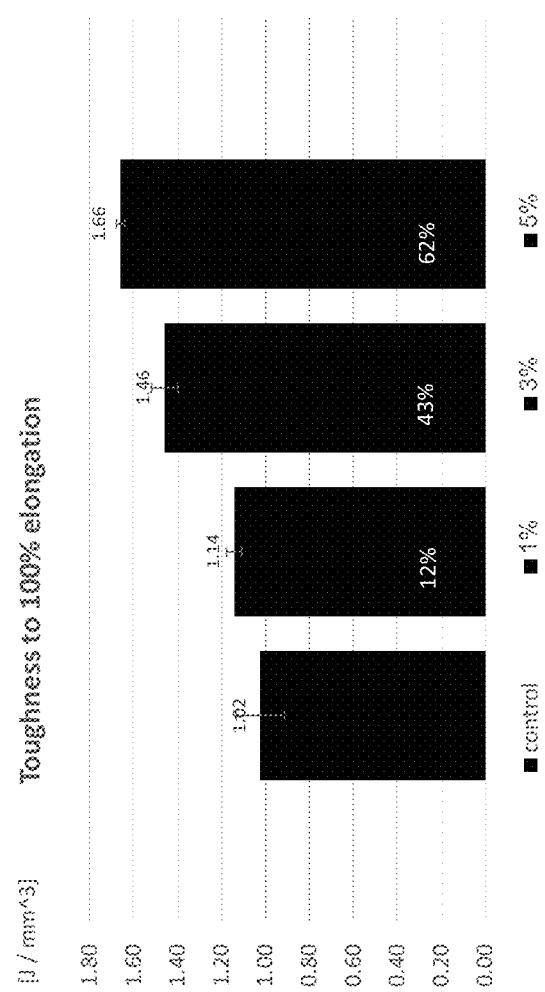

FIGS. 4A-D presents tensile test results including Young's modulus (FIG. 4A), Stress at 30% elongation (FIG. 4B) and toughness at 30% elongation (FIG. 4C) Stress at 100% elongation (FIG. 4D) and the toughness at 100% elongation FIG. 4E). All performed on control and SS enriched films, as indicated in the inset of each graph. Results are presented as mean±SD (n=5 different strips from the same film, for each condition).

Figure 5A:
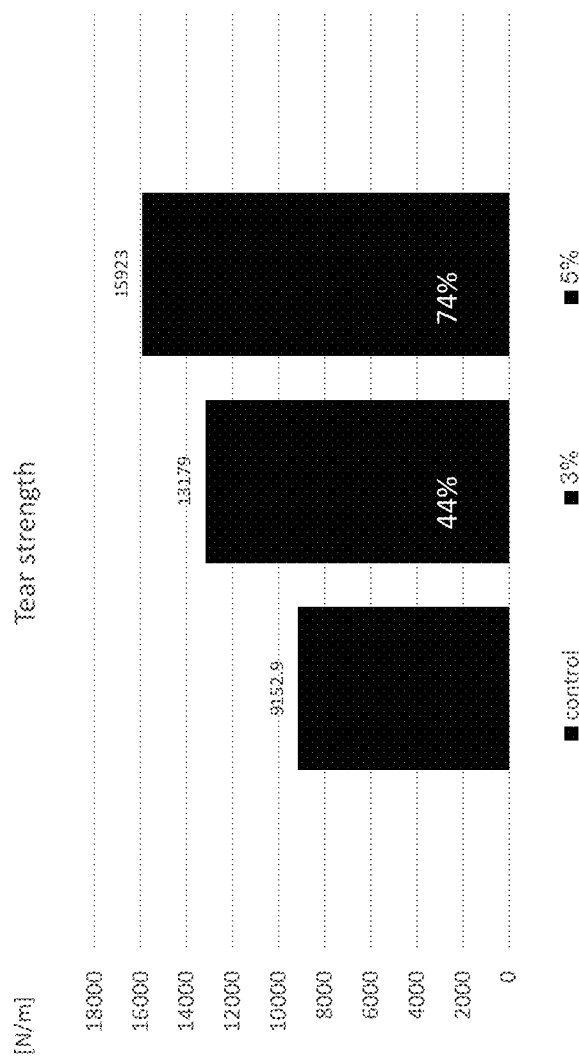
FIGS. 5A-B presents graphs showing tear strength (FIG. 5A) and curves (FIG. 5B) of enriched batches of thermoset PU with different loading percentages (control 3%, and 5% from lower to upper curve, respectively).
Figure 5B:
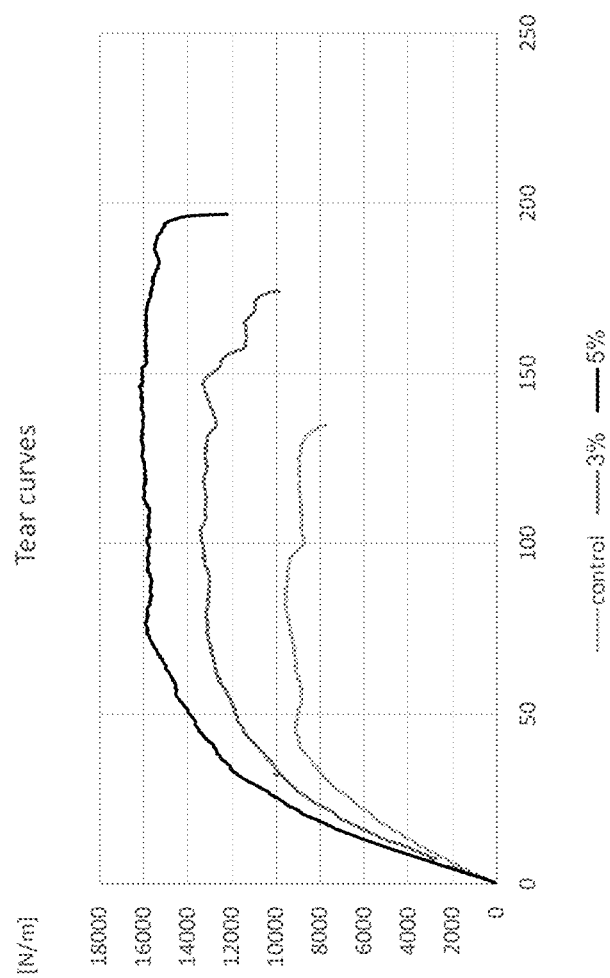

FIG. 5A presents tear strength results after enrichment with SS—each bar represents the result from one specimen. FIG. 5B presents typical tear test graph showing control, 3% and 5% enriched film.

Fibers have reached full dispersion in dope solution and cured films (see FIGS. 4A and 4B). As seen in FIG. 4A the Young's modulus has increased by 34%-150%, and the stress and the toughness behavior at 30% and at 100% elongation (FIGS. 4B-E) has increased significantly as well. As seen in FIGS. 5A-B the tear strength and the fracture toughness has increased in a dose dependent manner by 40-105% as fibers' concentration increased in the film.

Tecoflex®SG-93A (aliphatic polyether-based thermoplastic polyurethanes) from Lubrizol was dissolved 10% w/v in several solvents: THF, Toluene, Chloroform and Dioxane then left to evaporate for 24 hours. Following, the film was cut to strips of 8 mm width and 80 mm length and stretched by tensile tester.

Figures 6A, 6B, 6C:
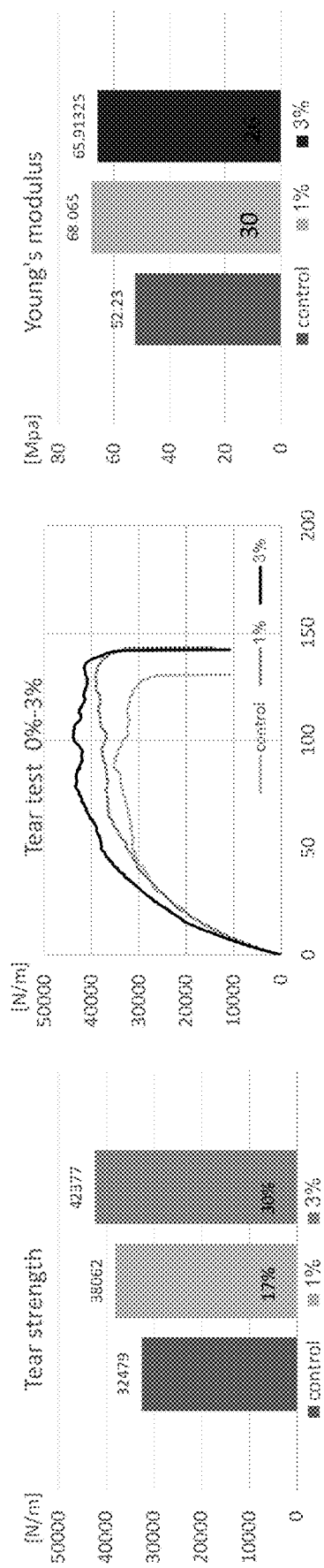
FIG. 6A-C present bar graphs showing: the Young's modulus (FIG. 6A), tear test (FIG. 6B) and tear strength (FIG. 6C) of polymer Tecoflex®SG-93A, having different (0%, 1%, 3%) concentrations (wt.) of enrichment with the disclosed proteins.

Tear test results: The results are shown in FIG. 6A-C, and the increase of the Young's Modulus and tear strength.

Exemplary Experimental Procedures for Thermoset Polyurethane:

U-2047 two-component Polyurethane compound—base (part A-Polyol) & curing agent (part B—HDI). Supplied by Polymer-G-Formulating Success. The preparation of two components according to manufacturer instructions. In case of fibers enrichment the fibers were mixed with part A before mixing with part B. The mixture was centrifuged for 4 minutes at 1000 RPM for degassing and was then vacuumed for 7 minutes at 100 mBar for additional degassing. The Curing profile was 24 h at room temperature followed by post cure for 3 h at 80° C. Experiments carried out with the following batches: control, 1%, 2% & 3% SS batches. Improved properties observed in all 4 parameters measured, tested by LLOYD tensile tester.

Figure 7:
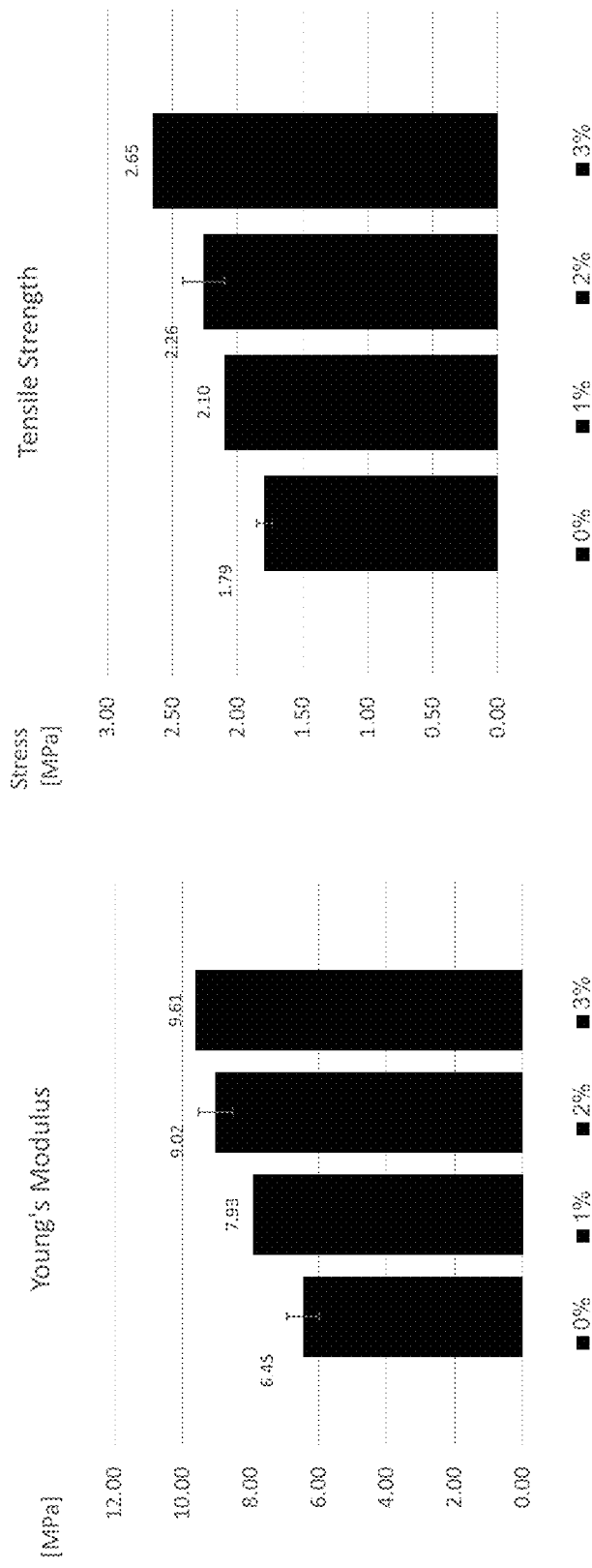
FIG. 7 presents bar graphs showing the Young's modulus (left panel), and tensile strength (right panel), of U-2047, being enriched 1% to 3% with the disclosed proteins, vis-à-vis a control of plain U-2047 (no protein enrichment).
Figure 8:
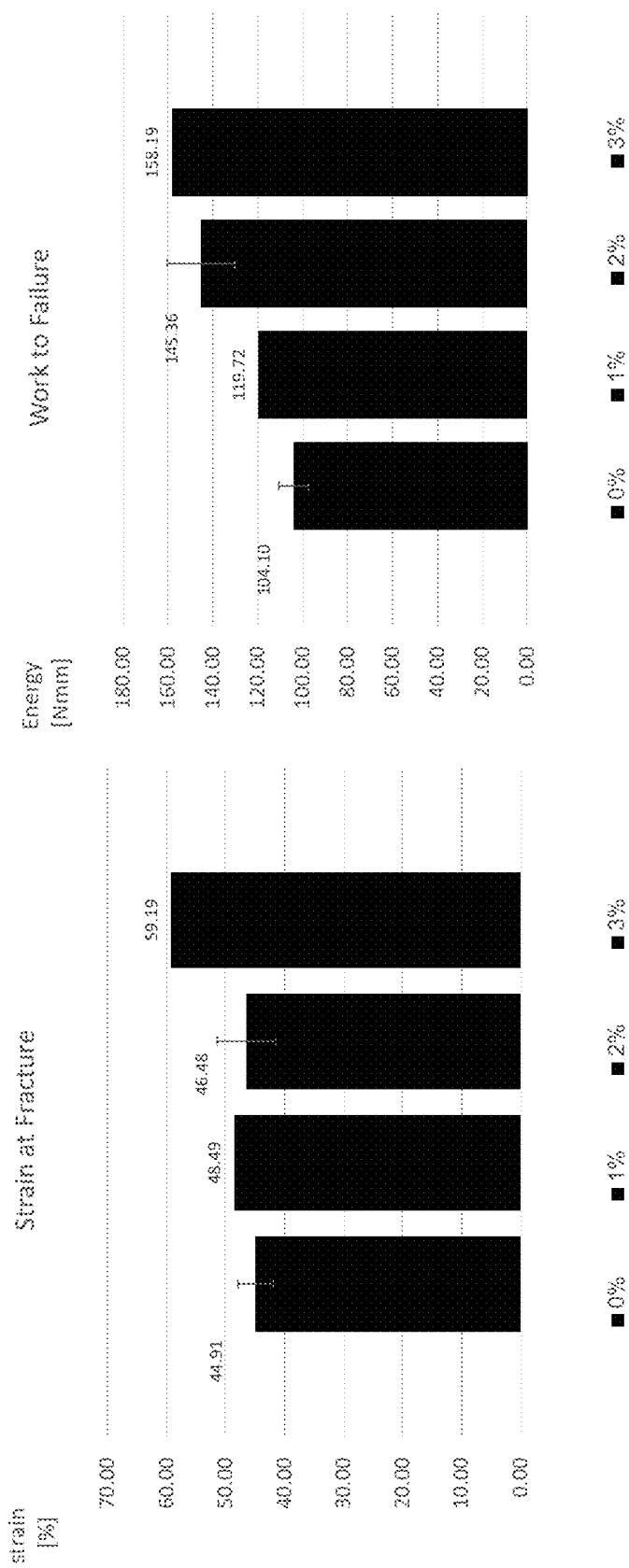
FIG. 8 presents bar graphs showing the strain at facture (left panel) and work to failure (right panel) of U-2047, being enriched 1% to 3% with the disclosed proteins, vis-à-vis a control of plain U-2047 (no protein enrichment).

The results are presented in FIGS. 7 and 8, and further summarized in Table 3 below showing the improvement rate of: Young's Modulus, tensile strength, strain at break, and work to failure.

TABLE 3

| | improvement rate | | |
|---|---|---|---|
| | 1% | 2% | 3% |
| Young's Modulus | 23%+ | 40%+ | 49%+ |
| tensile strength | 17%+ | 26%+ | 48%+ |
| strain at break | 8%+ | 3.5%+ | 32%+ |
| work to failure | 15%+ | 40%+ | 52%+ |

Tear Test: In exemplary procedures, Trouser tear test method was performed according to ASTM D-1938 protocol.

Materials: thermoset Polyurethane 2047 supplied by "Polymer G Ltd". Specimens' dimensions were 60 mm*20 mm*0.8 mm. In exemplary procedures, two control specimens were used (1% loaded specimens). The results are shown in Table 4A-B below, demonstrating 244% improvement in tear strength of the loaded specimens.

TABLE 4A

|  | Control | 1% loaded | Improvement Rate [%] |
|---|---|---|---|
| Tear Strength [N/mm] | 74 | 254.7 | 244%+ |

TABLE 4B

|  | Improvement rate | | |
|---|---|---|---|
|  | 1% | 2% | 3% |
| Young's Modulus | +22.5% | +39.5% | +48.5% |
| Tensile strength | +17% | +26% | +48% |
| Strain at break | +5.5% | +1% | +28.5% |
| Work to failure | +20.4% | +46.5% | +59.5% |

Example 3

Composites Comprising Nylon-Produced by Compounding and by Injection Molding

The use of Nylon 6, Nylon 6, 6 and Nylon 12 is widespread in the industry. By reinforcing nylon with spidersilk a significant improvement in mechanical properties was shown. First tests were conducted on pellets as received. This caused issues in the mixing phase when the large pellets didn't melt completely and sufficient mixing with SS was no achieved. Further tests were performed on a fine powder form of Nylon 12. In exemplary procedures, compounding was done on a DSM Xplore twin-screw micro-compounder (DSM, Heerlen, Netherlands). The preparation procedure is as follows: Filaments of about 100 µm in diameter were obtained using a micro compounder and were tested for mechanical properties. 5 specimen were tested.

The results are presented in FIGS. 9A, and the improvement of the mechanical properties of 2%, 4% fiber enrichment and CNT comparison (Young's Modulus, Stress @ 150% Elongation, and Yield Point) are presented in Table 5 below.

TABLE 5

| Young's Modulus improvement [%] | 96% |
|---|---|
| Stress @ 150% Elongation improvement [%] | 32% |
| Yield Point improvement [%] | 75% |

It is noteworthy that even though the enrichment percent indicated is 4%, the effective load percent is lower than that. In the production process some portion of the fibers remained on the feeder of the compounder. Furthermore the fibers in the composite agglomerated so their contribution to the composite strength decreased. It is assumed that the actual enrichment percent is at about 2%.

Figure 9A:
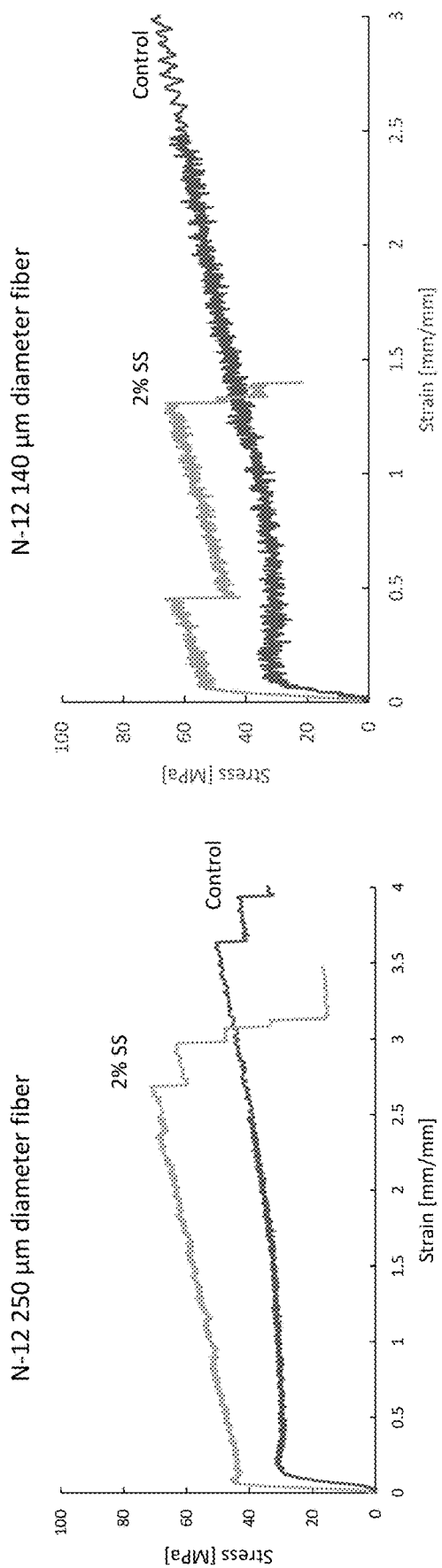
FIGS. 9A-F present graphs showing the stress-stain measurements (FIG. 9A, right and left panels, respectively) of Nylon 12 with fibers of 140 and 250 μm (2% enrichments.
Figure 9B:
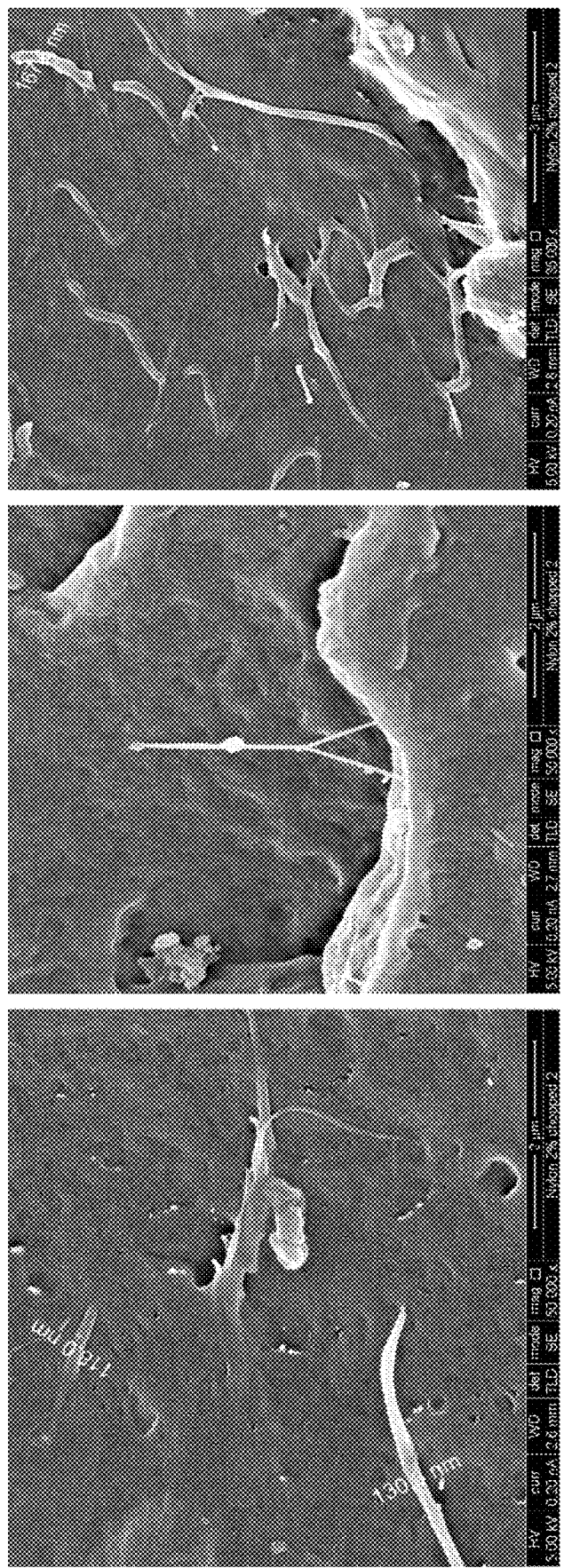
Figure 9C:
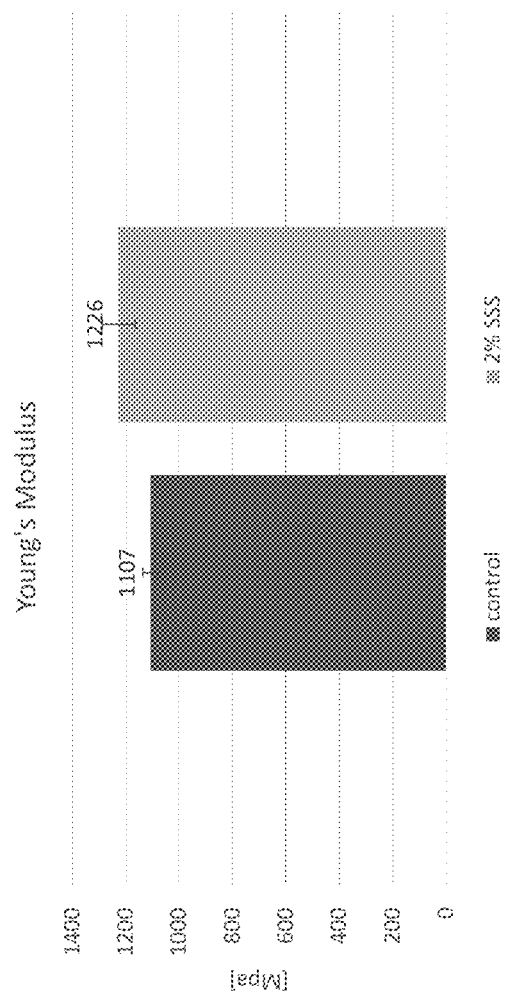
Figure 9D:
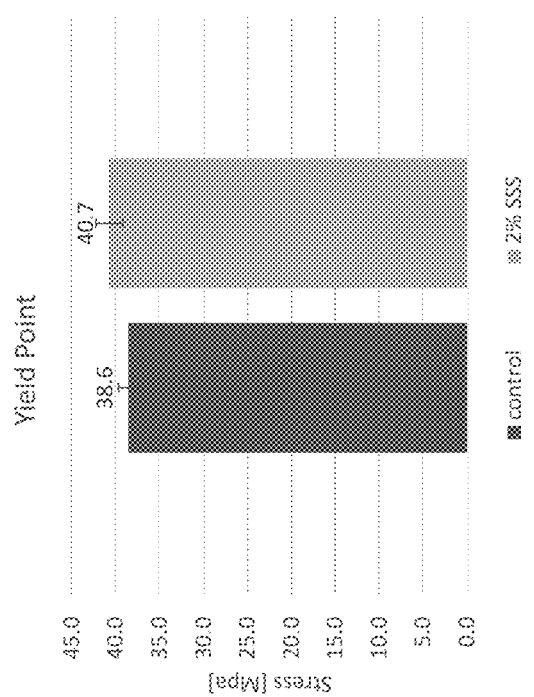
Figure 9E:
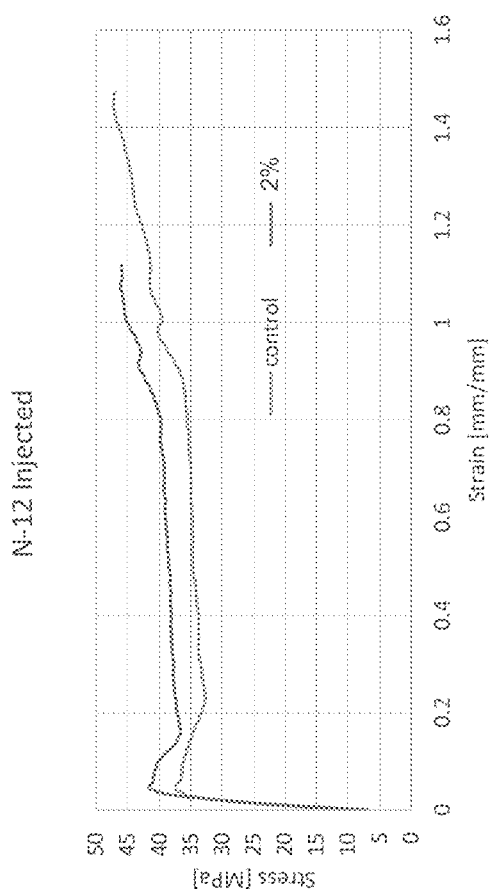

FIG. 9A presents the stress-stain measurements of Nylon 12 with fibers of diameters 140 and 250 µm (2% enrichments by extrusion). FIG. 9B presents representative SEM images of cross-section of fibers in Nylon 12 at 2% enrichment, showing SS fibers having a diameter of about 120 nm to 180 nm. It can be seen that several points in which spidersilk is well adhered, and middle panel in FIG. 9B shows a fiber in tension immersed in the polymeric matrix.

Nylon-12 was also fabricated using injection molding using Minijet Pro system by Hakke. Dog-bone specimens were injected using fine powder of Nylon 12. 2% SS enriched samples were prepared for evaluation in tensile tester system and the results are shown in FIGS. 9 C-E.

In additional procedures the compounding was performed with polylactic acid (PLA; 130 µm diameter) according to the following parameters:

| Extruder temperature | Screw speed [R.P.M.] | Collector speed [R.P.M.] | Mixing time [min.] |
|---|---|---|---|
| 185° C. | 50/30 | 250-300 | 0.5-1 |

Figure 9F:
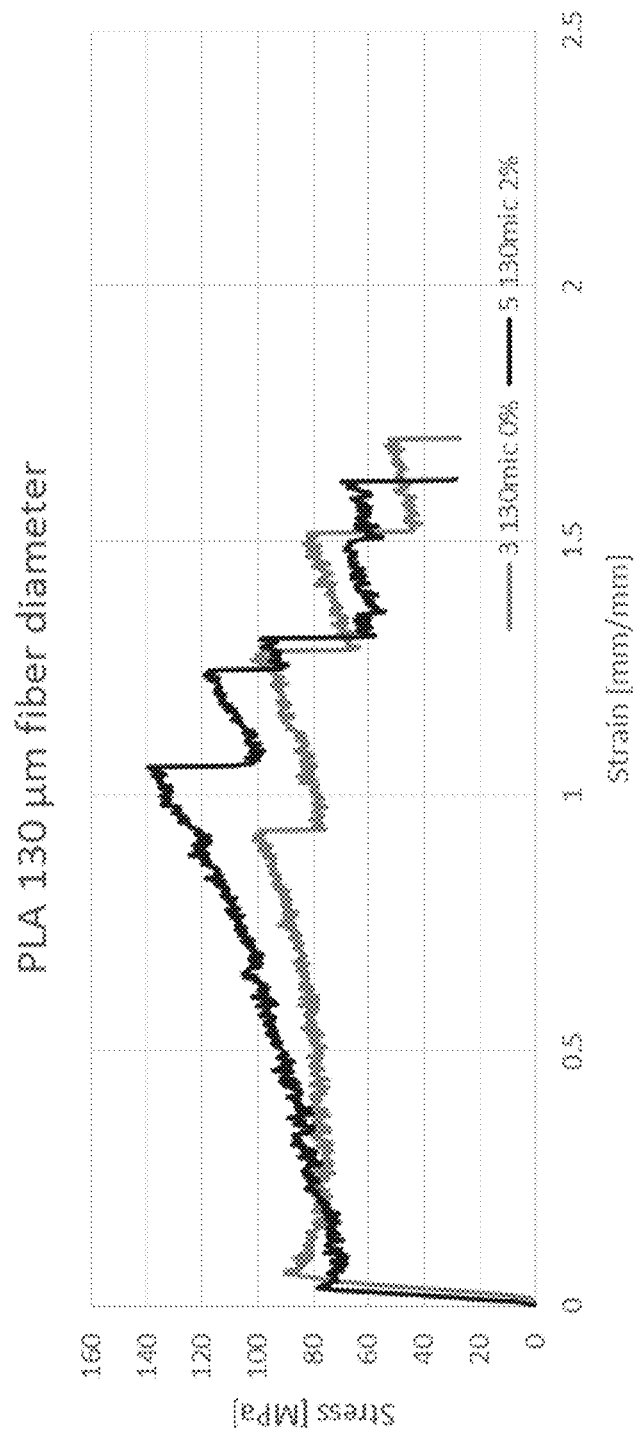

The results are presented in FIG. 9F improvement of stress-strain curve for the 2% SS enriched PLA sample.

Example 4

Covering with Spidersilk by Electrospinning

Electro-spinning is a method where very thin wires can be produced by electrical field acceleration of dissolved polymer and fibers in an organic solvent. The method works by rapid evaporation of the solvent by acceleration of the content towards the collector which is negatively charged at a voltage of 30 kV. The high electric potential difference forms electrical field that draws the droplet content of polymer and solvent towards the collector, the solvent rapidly evaporates and the polymer solidifies on the collector and allows for the formation of nano to micro fibers according to system setup parameters.

In exemplary procedures, the composite fibers were produced with diameter of 1-10 µm. Polymer matrices tested: TPU (thermoplastic polyurethane) and PCL (polycaprolactone); and Several enrichment percentages tested with varying porosity and mesh thickness received. TPU enrichment: SG-60, TPU was purchased from Tecoflex and used as received.

Dope solution preparation: In exemplary procedures, the TPU (SG60D) was dissolved in a mixture of DMF and THF (7:3 (w/w)) to obtain a 9, 11, or 13% (w/w) solutions. Each configuration was enriched with 1, 2, or 3% spidersilk percentage, building a matrix test of 12 configurations.

Spinning process: In exemplary procedures, the control solution setup was: i. flow rate 0.9 mL/h; ii. Electrostatic field ~1.2 kV/cm; iii. Temperature 26° C.; iv. Humidity ~60%; and v. Spinneret (needle 23G);

In exemplary procedures, the enriched solution setup was: i. flow rate 0.9 1.2 mL/h; electrostatic field ~1.2 kV/cm; iii. Temperature 26° C.; iv. Humidity ~60%; v. Spinneret (needle 23 G)

Mechanical properties evaluation: The electrospun mats were investigated by tensile testing at room temperature, using a tensile tester, Lloyd with a 500N load cell. Samples were approximately 20 mm-long, 5 mm-wide, and 0.15 mm-thick. Stress—strain curves were recorded at a stretching rate of 1 mm/min. The Stress was calculated according to the effective area of the sample according to the following equation:

$$\sigma = F/(A \cdot \rho_{mat}/\rho_{bulk}),$$

where F is the measured force, A is the measured cross-section, the apparent density is $\rho_{mat}/\rho_{bulk}$, where $\rho_{bulk}$ is the starch tapped powder density, and $\mu_{mat}$ is the fiber mat density.

Rheology of dope solutions: The rheology of solutions was studied by a rheometer TA Discovery 2.

PCL enrichment: PCL, 80000 Mn, was purchased from Sigma, and was used as received.

In exemplary procedures, the solutions were made with $CHCl_3$:DMF 6:4 ratio, and the following were prepared: Control—10 w/w PCL, 9.75 PCL and 0.7 spidersilk, 9.5 PCL and 1.33 spidersilk; or 9.25PCL and 1.77 spidersilk (the numbers represents wt. % in regards to the polymer solids). Electrospinning setup was similar to mentioned above for SG60D.

TPU Results:

Electrospinning process: Electrospinning process yielded TPU 12% (w/w) stable process with fibers with average diameter 0.8 um, and TPU 16% (w/w) stable process with fibers with average diameter 3.0 um. Enriched solutions were found to be too viscous so were diluted to about 10.5%.

Figure 10:
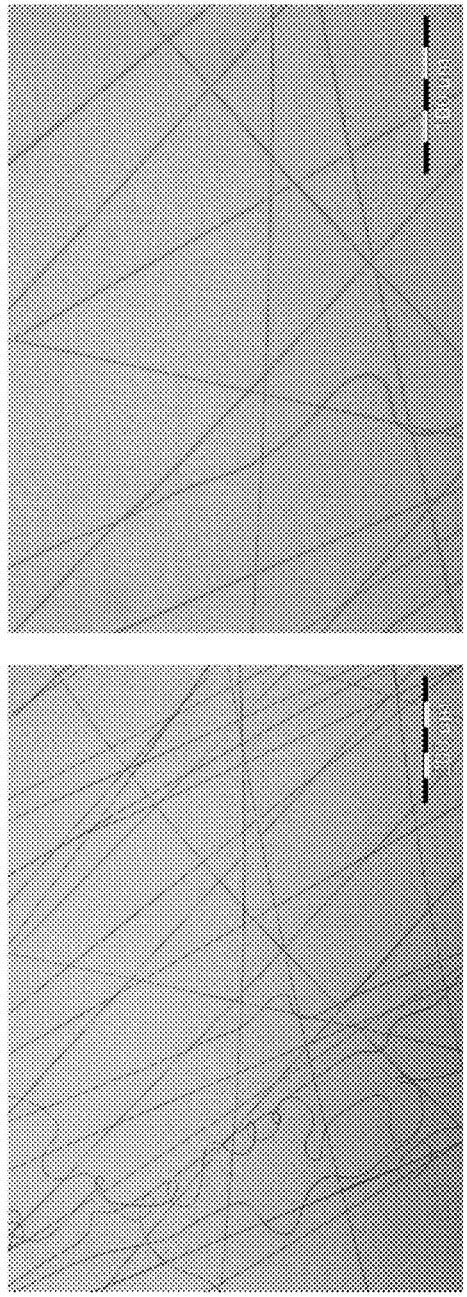
FIG. 10 presents images of electrospun 11% (w/w) thermoplastic polyurethane (TPU) fibers as control batches (bar: left panel, 200 μm; right panel, 100 μm).
Figure 12:
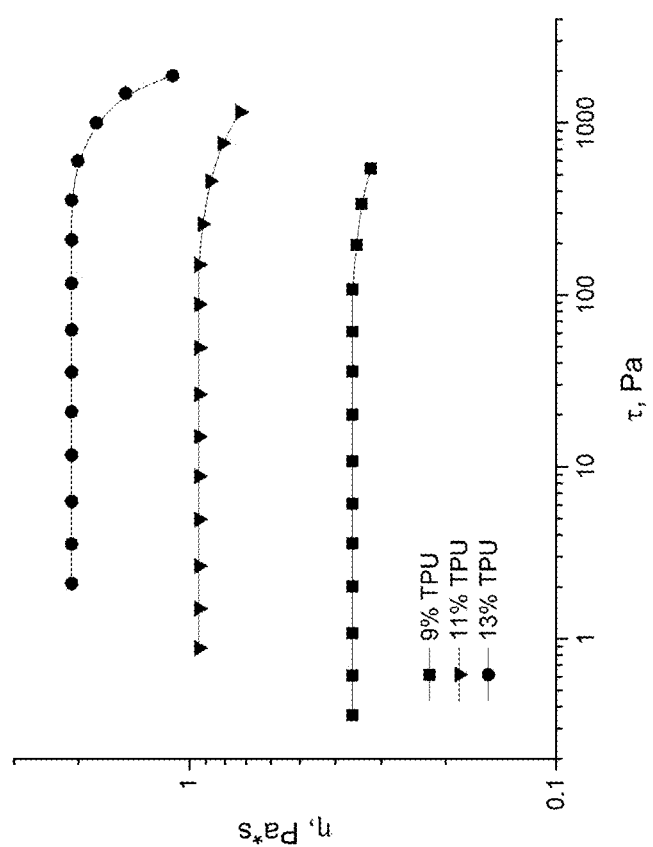
FIG. 12 presents graphs showing the rheological behavior of control batches at 9, 11, and 13% w/w of solid content of TPU (SG-60).
Figure 13A:
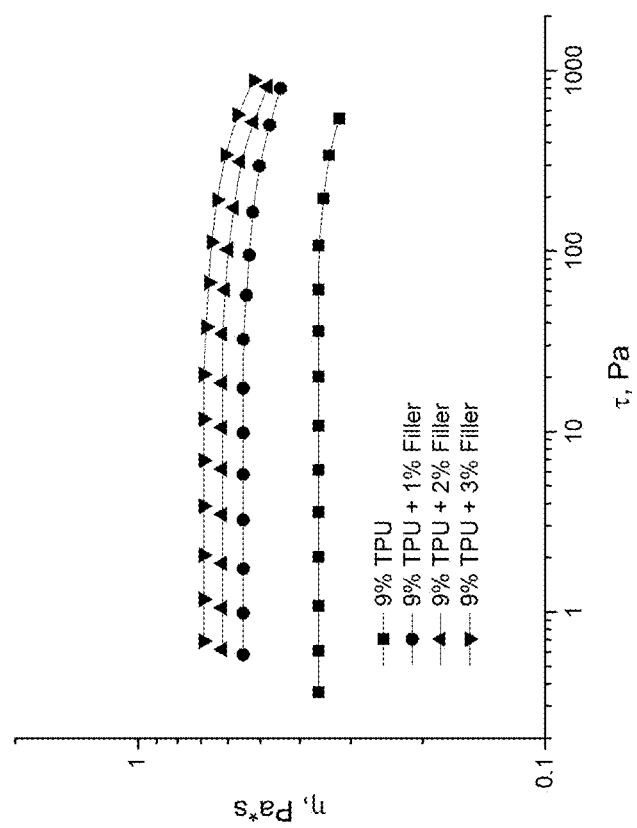
FIGS. 13A-B present graphs of rheological behavior showing that when increasing the amounts of filler added to SG-60, the viscosity increases yet the rheological behavior remains unaffected.
Figure 13B:
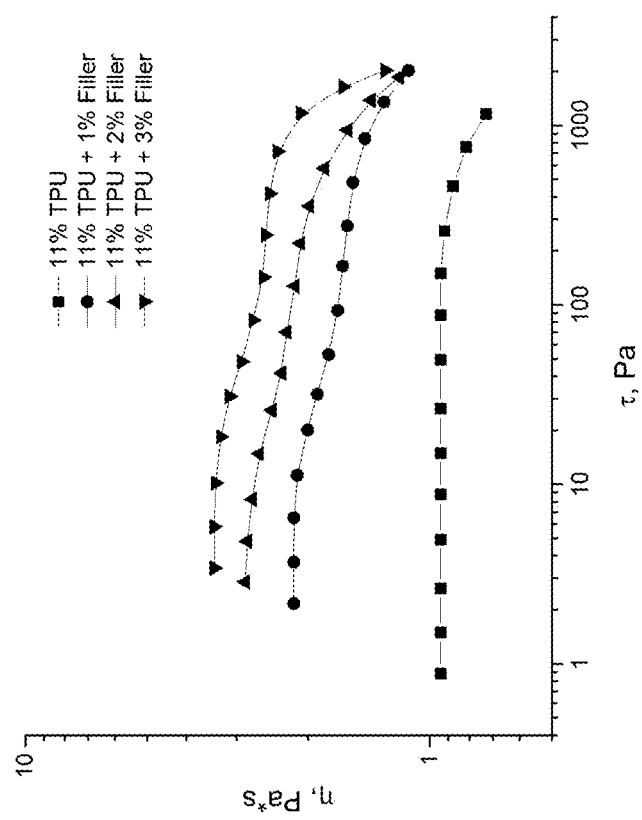

FIG. 10 presents electrospun 11% (w/w) TPU fibers as control batches. FIG. 11 presents electrospun fibers ~10.5% (w/w) TPU+~2% (w/w) fillers. FIG. 12 presents rheological behavior of control batches at 9, 11, and 13% w/w of solid content of SG-60. FIGS. 13A-B demonstrate that when increasing the amounts of filler added to SG-60, the viscosity increases yet the rheological behavior is unaffected.

The results of the mechanical properties are summarized in Table 6 showing an improvement in young's modulus.

TABLE 6

| | | Porosity | SD | Modulus (MPa) | SD | Tensile Strength (MPa) | SD | Toughness (J/mm3) | SD |
|---|---|---|---|---|---|---|---|---|---|
| 9% | Control | 43% | 4% | 19.80 | 0.08 | 36.415 | 0.377 | 25.729 | 1.856 |
| | 1% | 40% | 13% | 19.77 | 3.88 | 24.143 | 4.349 | 12.149 | 2.384 |
| | 2% | 22% | 8% | 33.79 | 1.41 | 35.101 | 1.510 | 19.739 | 2.046 |
| | 3% | 14% | 6% | 38.34 | 2.53 | 37.704 | 1.458 | 26.578 | 3.894 |
| 11% | Control | 36% | 3% | 31.26 | 8.23 | 37.222 | 2.394 | 33.795 | 6.290 |
| | 1% | 14% | 9% | 44.80 | 1.75 | 33.488 | 1.727 | 42.358 | 6.587 |
| | 2% | 20% | 7% | 50.23 | 4.65 | 27.593 | 3.063 | 33.707 | 5.494 |

Figure 14:
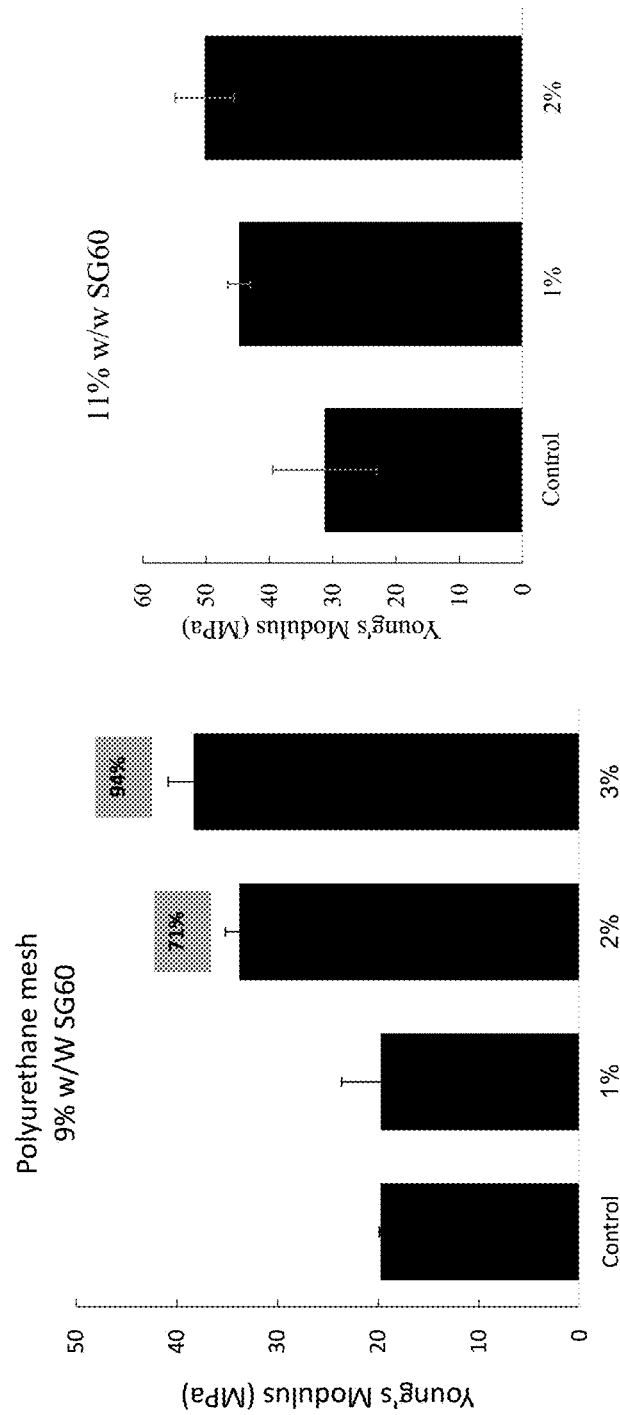
FIG. 14 presents bar graphs showing the Young's modulus measurements of electrospun meshes made of 9% w/w SG60 (left) and 11% w/w SG60 (right) with the disclosed fiber, and with filler (0, 1%, 2%, or 3%).

FIG. 14 presents the Young's modulus results Left side image presents the modulus results for 9% solid content of TPU where it is seen that significant enrichment is reached at 2% and 3% loading of SS. Right side image presents the modulus results for 11% solid content of TPU where it seen that significant enrichment is reached at 2% loading of SS.

Figure 15:
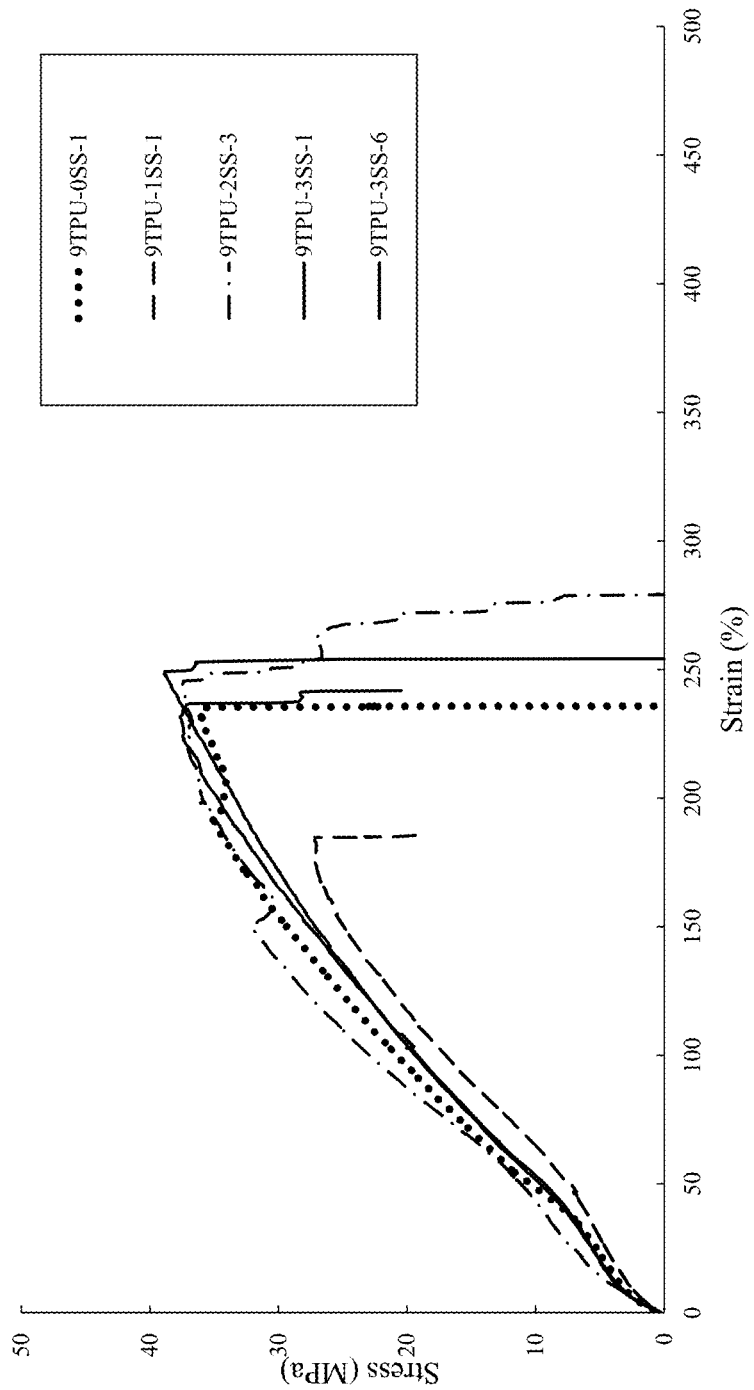
FIG. 15 presents stress-strain curve for the 9% w/w configurations.

Stress-strain curves are further presented herein: FIG. 15 presents stress-strain curve for the 9% w/w configurations.

Figure 16:
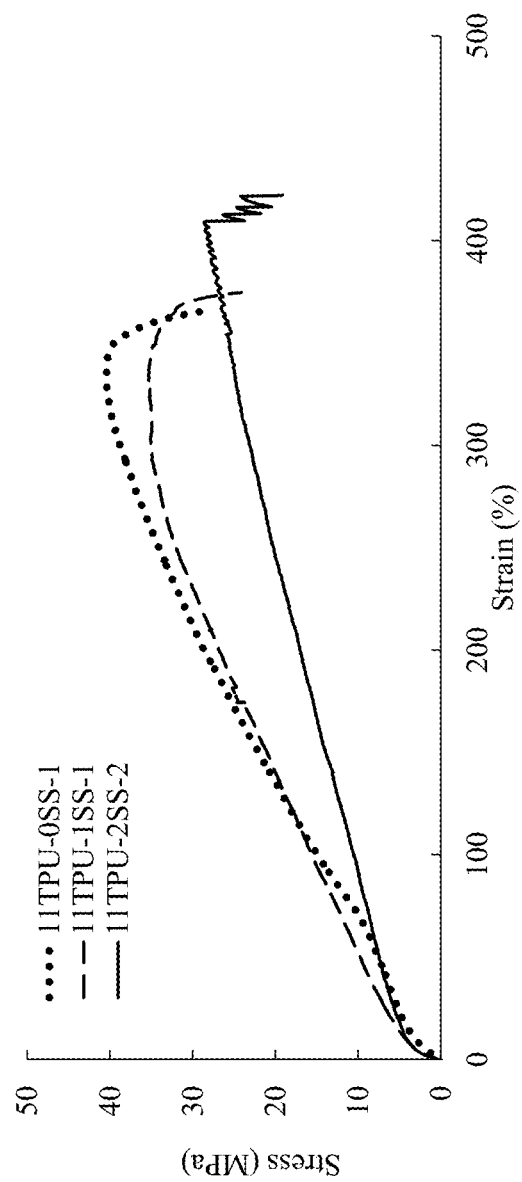
FIG. 16 presents stress-strain curve for the 11% w/w configurations.

FIG. 16 presents stress-strain curve for the 11% w/w configurations.

Figure 17:
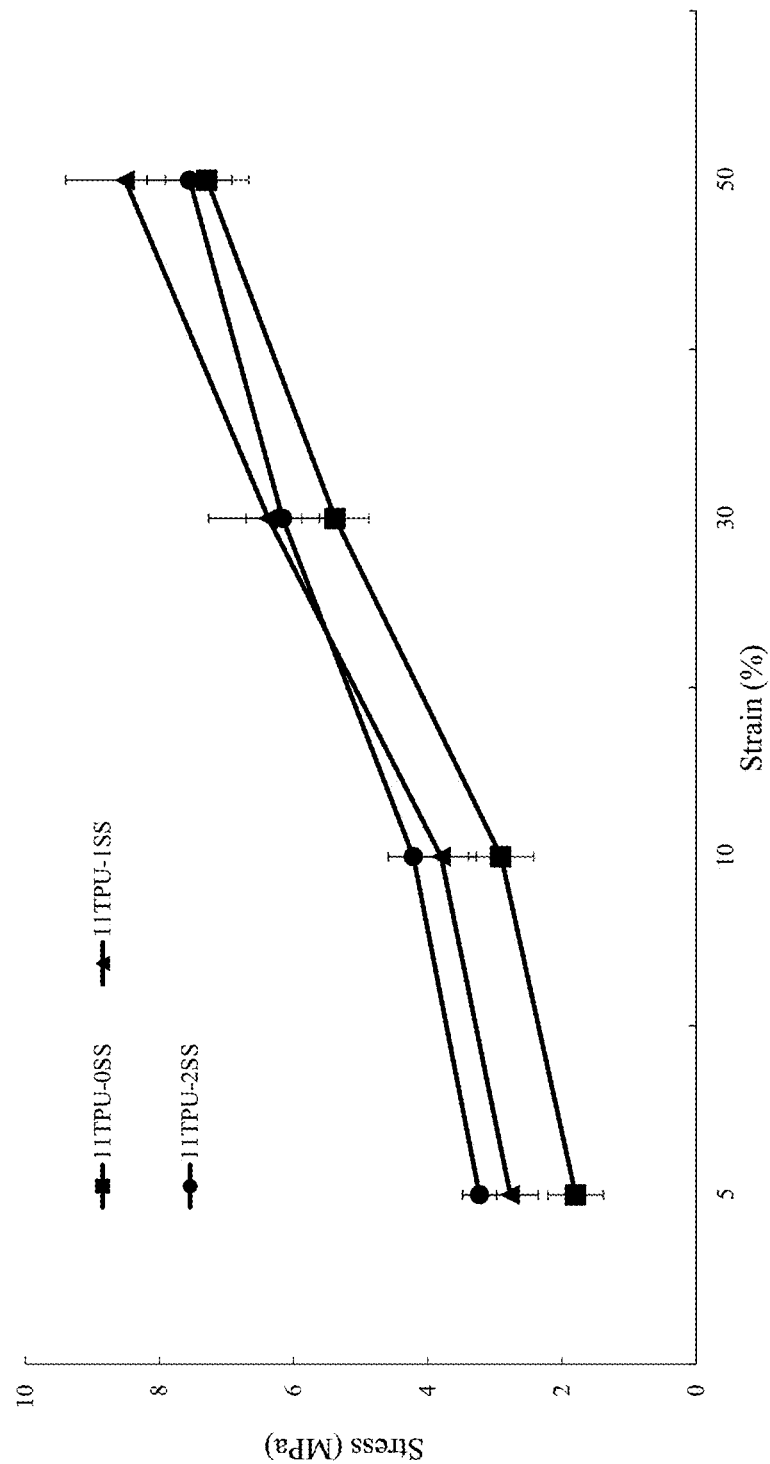
FIG. 17 presents a zoom-in graph on the elastic region of 11% w/w configuration. It is shown that in the elastic region the enriched meshes have higher values after which there is a shift and the control mesh has higher values.

FIG. 17 presents zoom-in on the elastic region of 11% w/w configuration. In the elastic region the enriched meshes have higher values after which there is a shift and the control mesh has higher values.

Figure 18:
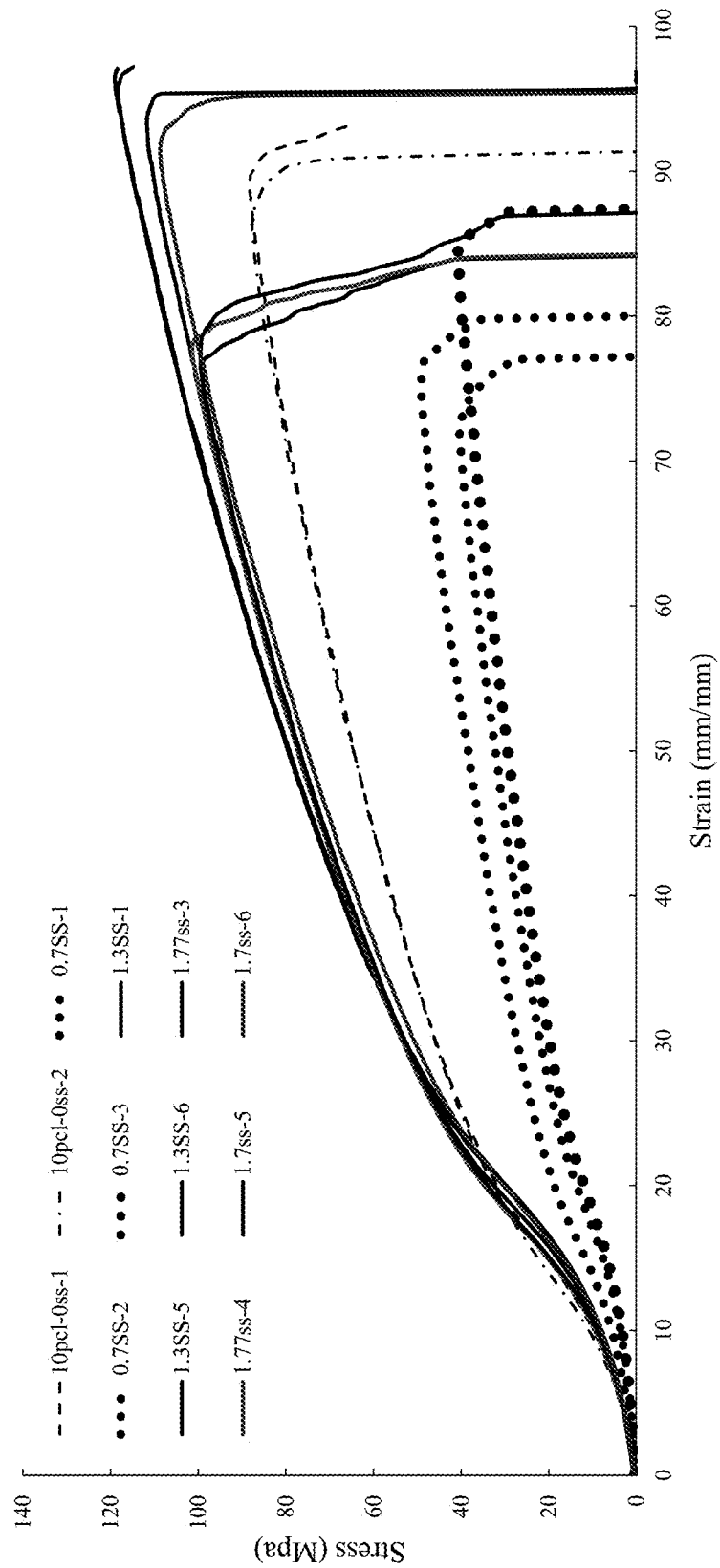
FIG. 18 shows stress-strain curves for PCL electrospun mesh material from different batches, demonstrating that 1.33% Spidersilk enrichment produced the best results.
Figure 19:
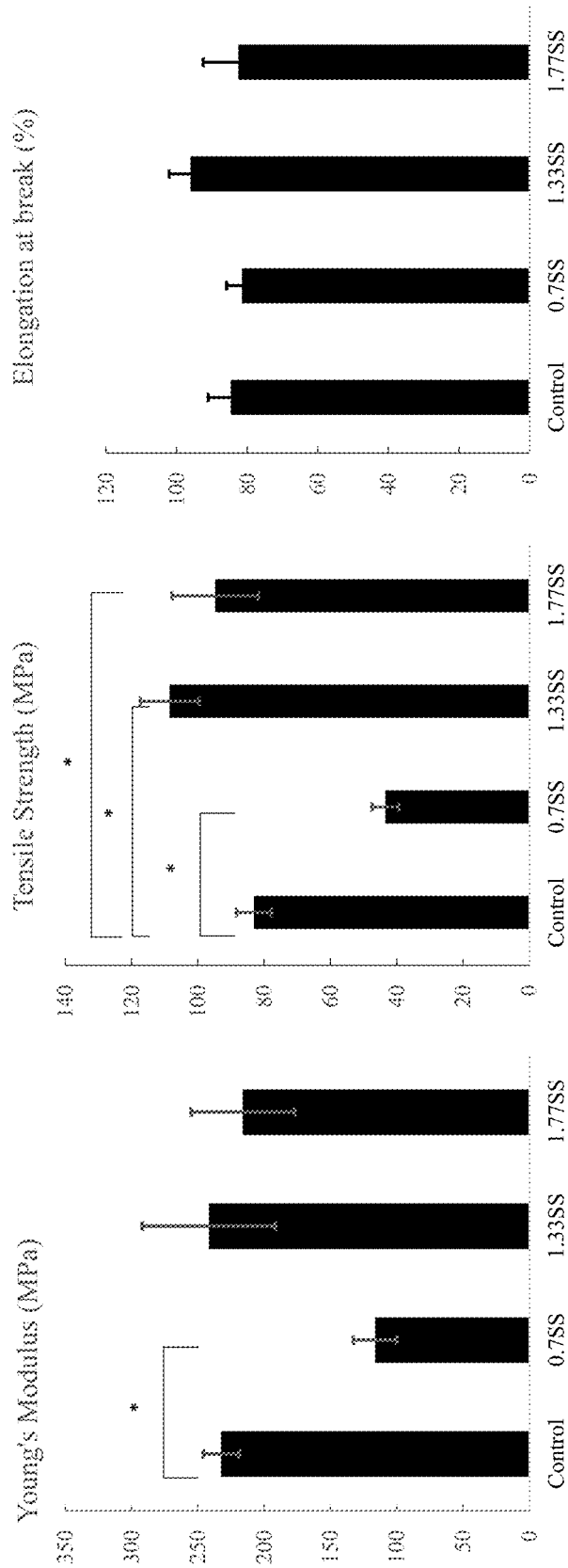
FIG. 19 presents statistics of mechanical properties for the PCL electrospinning: Young Modulus (left panel), Tensile strength (middle panel), and Elongation at break (right panel).

PCL results: The results for PCL electrospinning test are summarized in Table 7 below for the PCL electrospinning test:

Stress-strain curve is further presented herein. FIG. 18 shows stress-strain curves for PCL electrospinning batches, demonstrating that 1.33% Spidersilk enrichment produced the best results. FIG. 19 presents statistics of results for the PCL electrospinning.

Solvent system, polarity, fiber dissolution and evaporation: The fiber is soluble in Hexafluoroisopropanol (HFIP), concentrated sulfuric acid or meta-cresol. This is due to the strong hydrogen bonds and dense crystalline fiber morphology. Based on experimental data, the selected solvent used for fully dissolving the fibers is HFIP, due to its high vapor pressure, and polarity, making it excellent carrier for electrospinning. After full dissolution the samples were placed in syringe connected with Luer lock 22G needle.

Syringe pump speed: The syringe pump speed was examined between the ranges of 0.001-1.0 ml/min. In exemplary procedures, a solution of 4-5% (wt/vol) of lyophilized fibers in HFIP was made. The dissolution process took about 2 h, to dissolve and to form clear a viscous solution. The HFIP was then evaporated in the hood, until the volume was reduced and the concentration was at 8-13% (wt/vol). The voltage was set to 30 kV.

In additional exemplary procedures, the fibers solutions were electrospun, to initially form a mesh collected on aluminum foil or on rotating mandrel. Next, the fibers were collected on stents, to demonstrate the coating feasibility on medical devices. Two types of fiber solutions were made. The reference was of *Bombyx mori* (BM) fibers, dissolved in HFIP, and the other was of synthetic spider silk (SS) fibers, lyophilized post production and re-dissolved in HFIP for electrospinning.

Figure 20:
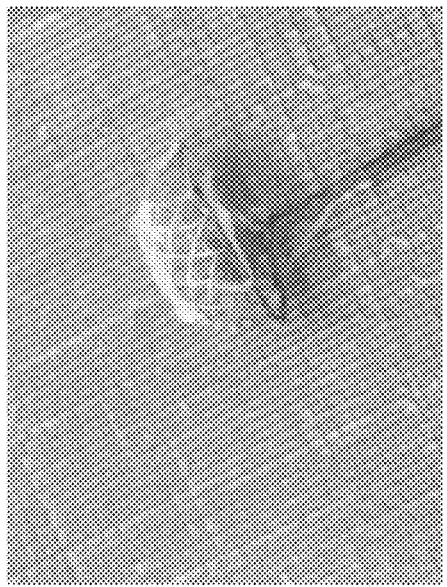
FIG. 20 presents a photograph of electrospun *Bombyx mori* (BM) coated stent, showing the nano fibers between the stent metallic rods, forming a nano mesh.

FIG. 20 presents a photograph image showing a basket (emerges from a thin hollow duct inserted to the arteries while folded) coated with nano fibers, forming nano mesh. The coating was performed using the *Bombyx mori* fibers, on stating stent.

Figure 21:
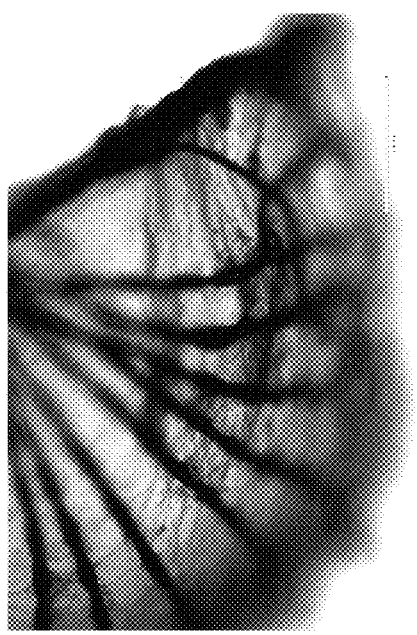
FIG. 21 presents an optical microscopy image of electrospun *Bombyx mori* (BM) coated stent, showing the nano fibers between the stent metallic rods, forming a nano mesh.

FIG. 21 presents an optical microscopy images showing the basket coated with nano fibers, forming nano mesh.

Figure 22:
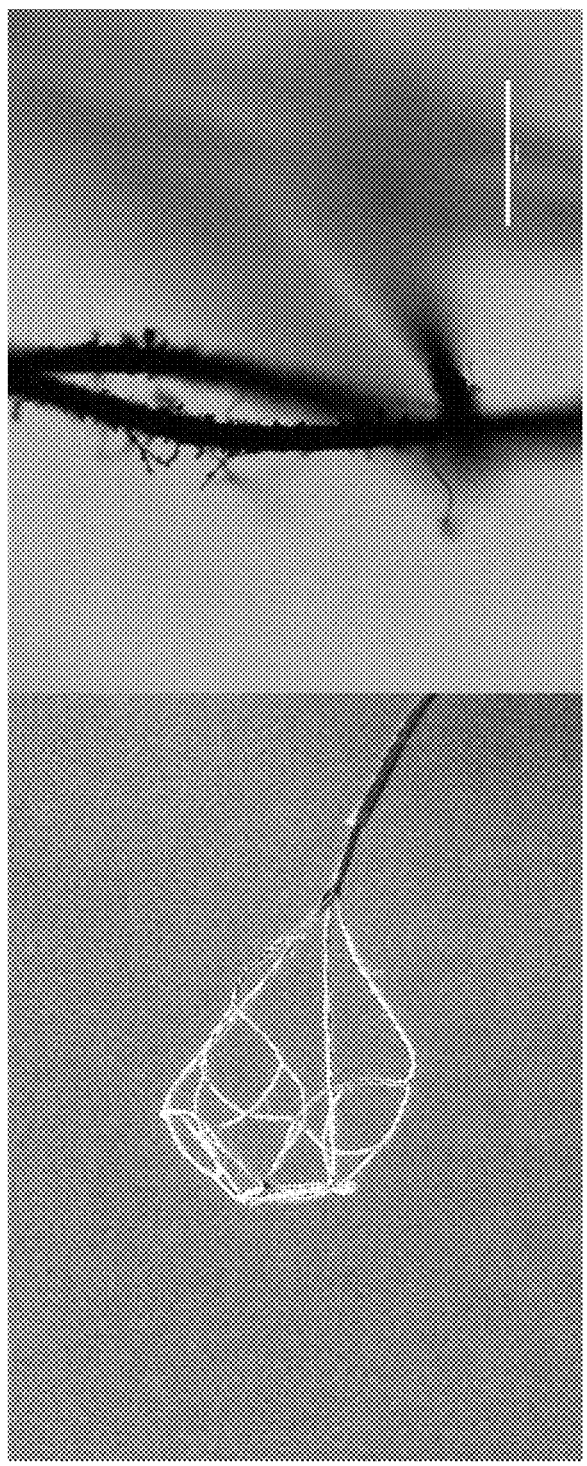
FIG. 22 presents a photograph (left) and an optical microscopy of electrospun Spider silk (SS) coated stent, showing the nano fibers formation on the stent metallic rods, and forming the coating.

In additional exemplary procedures, a coating technique was applied using the spider silk (SS) solution to coat the basket rods. As shown in FIG. 22, micro coating was formed

TABLE 7

| | Control | | 9.75PCL-0.7SS | | 9.5PCL-1.33SS | | 9.25PCL-1.77SS | |
|---|---|---|---|---|---|---|---|---|
| | | SD | | SD | | SD | | SD |
| Effective Young's modulus (MPa) | 232.337 | 13.390 | 116.230 | 16.538 | 241.661 | 50.347 | 216.090 | 38.934 |
| Percentage Strain at Break | 84.669 | 6.374 | 81.470 | 4.352 | 96.075 | 6.009 | 82.534 | 9.934 |
| Effective Tensile Strength (MPa) | 83.069 | 5.297 | 43.421 | 4.040 | 108.467 | 8.908 | 94.747 | 13.028 | using the electrospinning coating technique, and as can be seen by the optical microscopy, the co-ting is composed of nano fibers.

In additional exemplary procedures, another technique of dip coating the stent in the fibers HFIP solution was examined.

Figure 23:
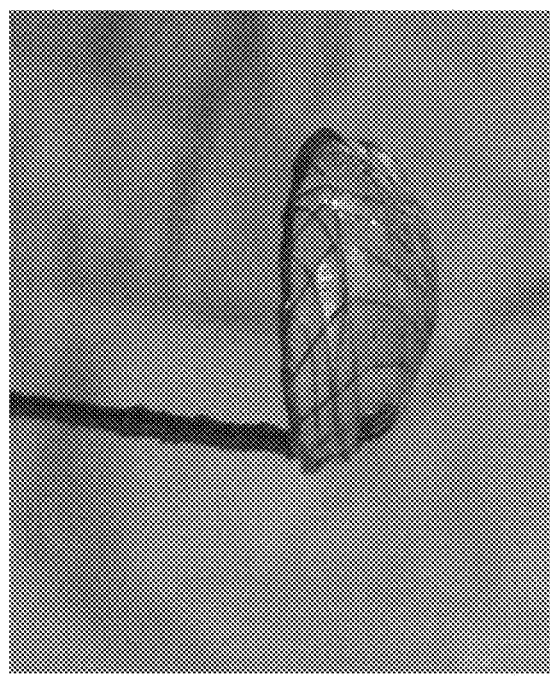
FIG. 23 presents a photograph showing a film coated stent using dip coating of the stent in BM Hexafluoroisopropanol (HFIP) solution.

FIG. 23 presents a film coated stent using dip coating of the basket. in BM HFIP solution, demonstrating a uniform thin film which coats the whole stent.

Figure 24:
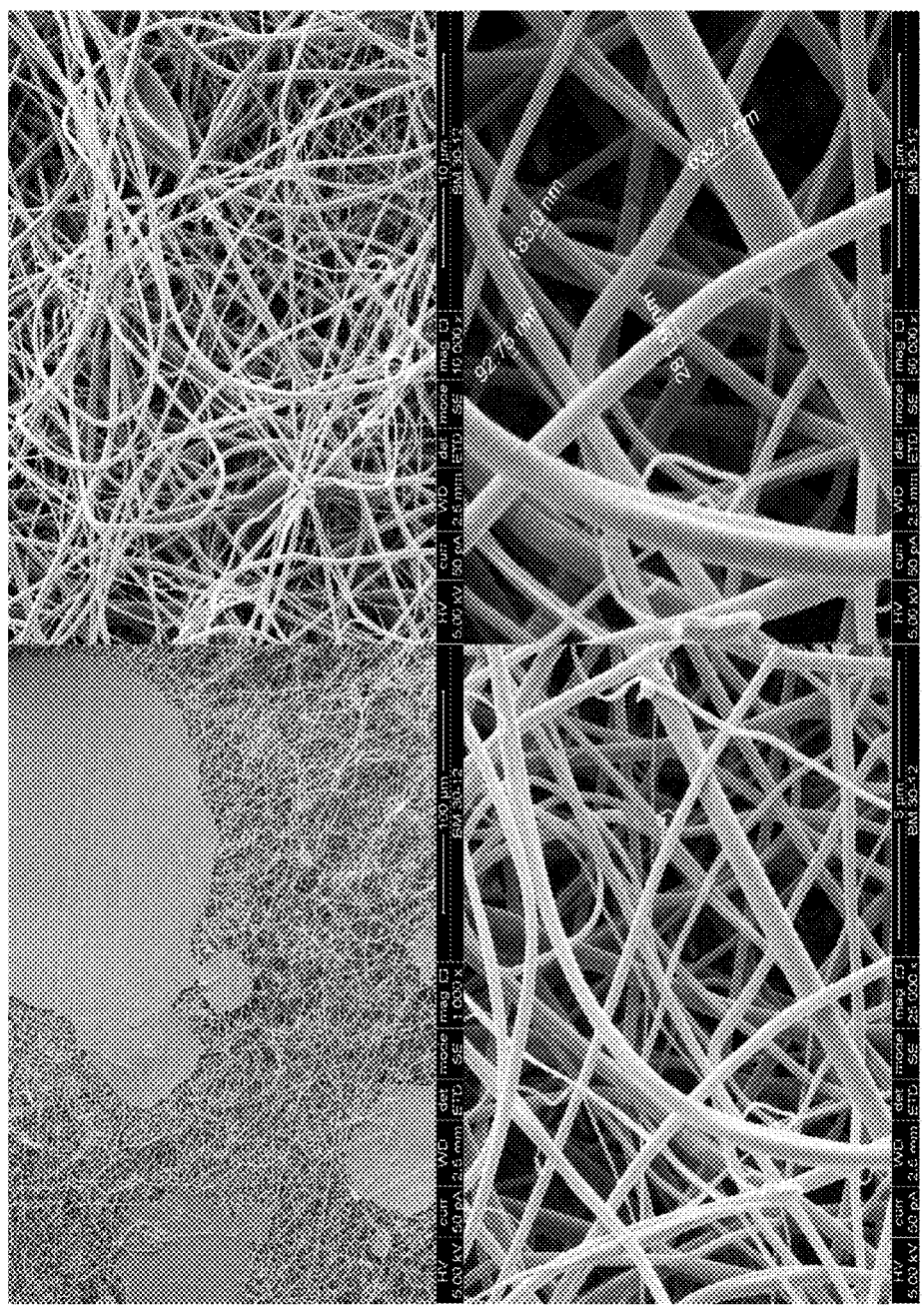
FIG. 24 presents SEM images showing an electrospun mesh of nano fibers (about 90 to 630 nm) made of solution of *Bombyx mori* fibers dissolved in HFIP, at various scales. Scale bars in μm, clockwise from upper left: 100, 10, 2, and 5.
Figure 25:
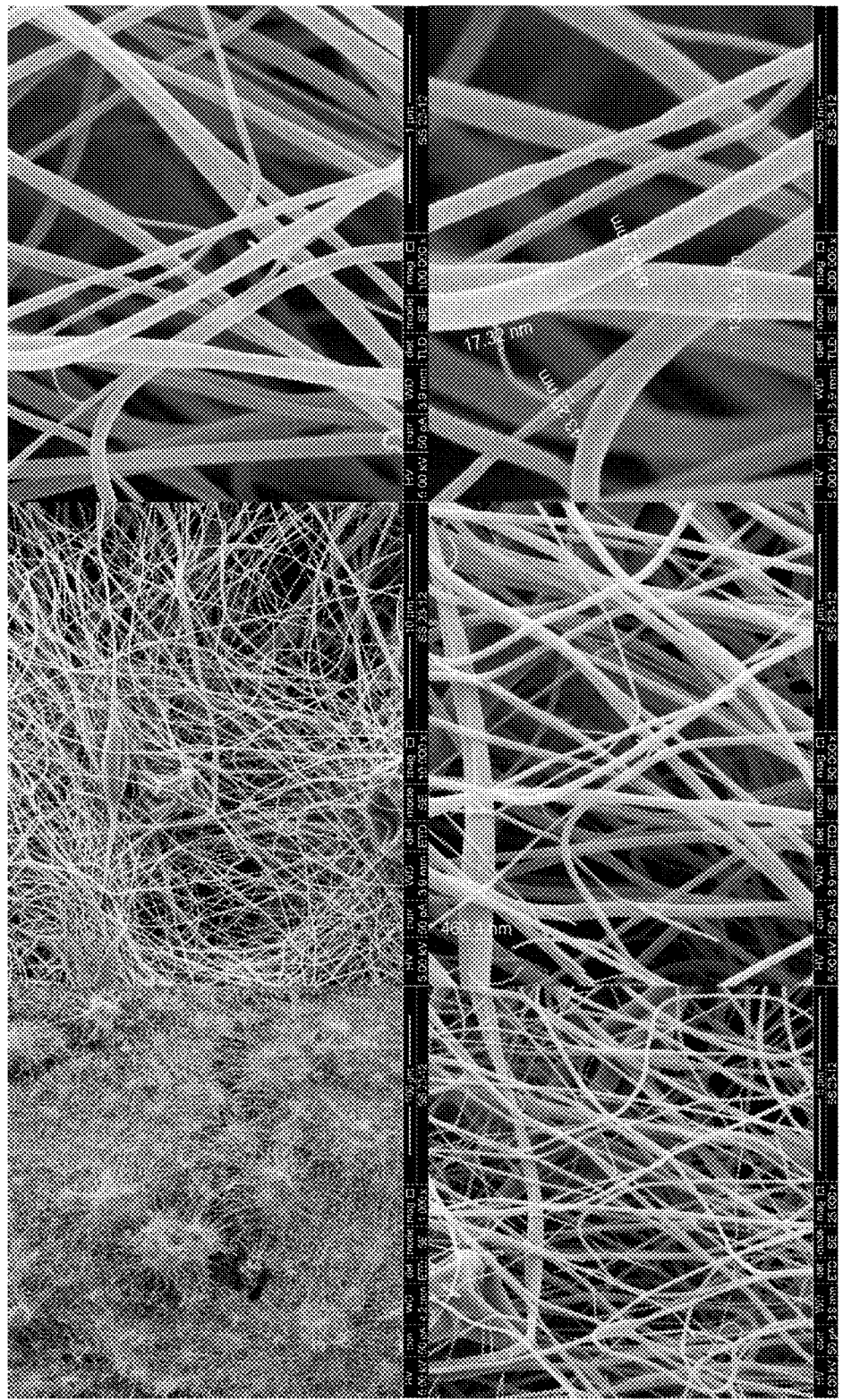
FIG. 25 presents SEM images showing electrospun mesh of nano fibers made of solution of spider silk fibers dissolved in HFIP. Scale bars in μm, clockwise from upper left: 100, 10, 1, 500, 2 and 5.

Scanning electron microscopy (SEM) analysis: The reference electrospinning was of *Bombyx mori* (BM) fibers, dissolved in HFIP, and the other was of synthetic spider silk (SS) fibers, lyophilized post production and re-dissolved in HFIP for electrospinning. High-resolution scanning electron microscopy (HR-SEM; Sirion, FEI Company Eindhoven, The Netherlands) was used to analyze the coating surface morphology. The HR-SEM Micrographs were taken using a voltage range of 3-7 kV for the polymeric samples. Prior to analysis, the samples were sputter-coated for 60 seconds forming about 10 nm gold/platinum layer in order to prevent charging. Ultra-high spatial resolution was used for both structural and high-resolution analysis. An energy dispersive x-ray spectroscopy (EDAX) measurement was used in the microanalysis to detect the values of the characteristic x-rays generated within the electron microscope. The micrographs are shown in the following Figures: FIG. 24 for the *Bombyx Mori*, and FIG. 25 for the synthetic spider silk fibers. The following Table 8, summarizes the measured fibers diameter measured using the SEM micrographs.

TABLE 8

| Bombyx Mori | | SpiderSilk | |
|---|---|---|---|
| Average diameter [nm] | STDEV [nm] | Average diameter [nm] | STDEV [nm] |
| 205 | 166 | 54 | 38 |

From the HR-SEM analysis it was demonstrated that both materials allow the formation of uniform fibers. The BM fibers are thicker, with average diameter of 205±166 nm and the SS fibers display average diameter of 54±38 nm. The SS fiber mesh was composed of high density small diameter fibers, and can function with high performance for variety of applications.

It can be concluded that this technique can be utilized for making fiber coating for stents and meshes, being an efficient tool for the coating and remaking the fibers from the solution, and displaying good adhesion to the surface. The outcome was fibers at thickness in the nanometer scale, with the fibers density being high enough to perform a beneficial coating for various applications. It is to note that for coating of such devices the composite of electrospun fibers is more beneficial than pure BM silk or SS dissolved in HFIP since the mechanical properties of the fibers may be damaged during HFIP solubilization.

Example 5

Composites Comprising Butvar, EVOH, pHEMA, and UV-Curable Acrylate Formulation

In order to characterize the mechanical properties of the Synthetic fibers samples of polymer matrices reinforced by the synthetic fibers were prepared. The polymer matrices chosen to be studied were:
  pHEMA (Polyhydroxyethylmethacrylate)
  polyvinyl butyral resin (Butvar B-98)
  Vero Clear (Inkjet material, UV-cured supplied by Stratasys)

The fibers were dispersed in the polymer solution & then the solution cured by polymerization. The samples were enriched with various enrichment percent between 0-5%. After curing, the samples were sliced to strips of 80 mm length 8 mm width and thickness of 0.9 mm. The VeroClear samples were injected on a mold held between 2 glass sheets. UV-cured process was held by a mercury lamp at 150 W for 10-15 minutes cure time. After curing, the sample released from the mold and sliced to a strips of 80 mm length 8 mm width and thickness of 1-2 mm. The specimens were stretched by tensile tester (Instron 4502 according to the ASTM D628 with the required modification). The results are detailed in the following Tables 9 A-E.

TABLE 9A (pHEMA 48%)

| | |
|---|---|
| Young's Modulus improvement [%] | 44% |
| Tensile Strength improvement [%] | 78% |
| Elongation improvement [%] | 59% |

TABLE 9B (pHEMA 50%)

| | |
|---|---|
| Yield Point improvement [%] | 100% |
| Tensile Strength improvement [%] | 38% |
| Elongation improvement [%] | 47% |

TABLE 9C (pHEMA 60%)

| | |
|---|---|
| Young's Modulus improvement [%] | 55% |

TABLE 9D (Butvar)

| | |
|---|---|
| Young's Modulus improvement [%] | 37% |
| Tensile Strength improvement [%] | 71% |

TABLE 9E (Vero Clear)

| Test | Parameter | Enrichment Result |
|---|---|---|
| Tensile test | Modulus (MPa) | 33% |
| | Tensile Strength at break (MPa) | −17% |
| | Elongation at break | −55% |
| Flexural test | Modulus (MPa) | 15% |
| | Tensile Strength at break (MPa) | 38% |
| | Elongation at break | −67% |

The young modulus is calculated in the base of the Vero Clear results and according to the Rule of Mixtures:

$$E_c = E_M V_M + E_F V_F$$

Because of the random dispersion of the fibers in the matrix its can be assumed that with 1% enrichment approximately only 0.7% contribute in the tension axis. According to that the calculation will be:

$$E_F = \frac{561 - (420 * 0.993)}{0.007} = 14143 \text{ MPa}$$

The value obtained for the fibers young modulus is 14 GPa.

Figure 26:
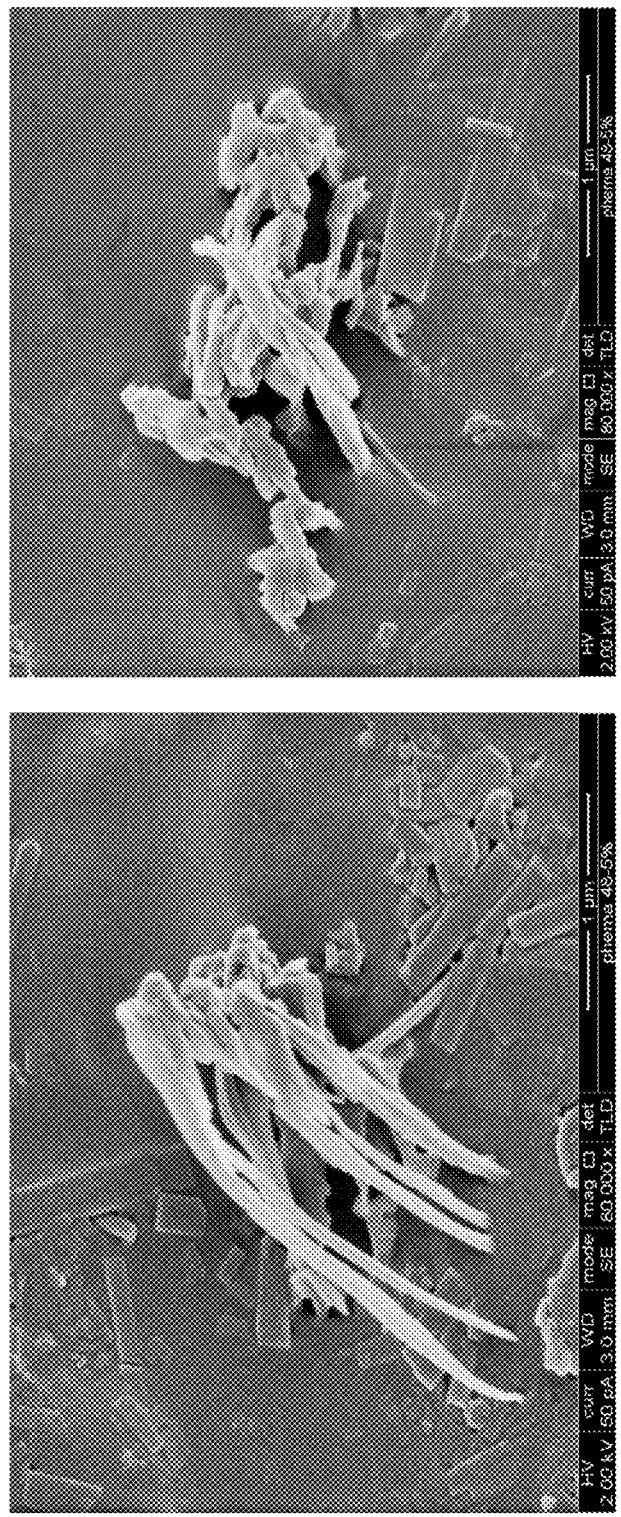
FIG. 26 presents SEM images showing an agglomerate of protein fibers in Poly (2-hydroxyethyl methacrylate) (P-HEMA). Scale bars are 1 μm.
Figure 27:
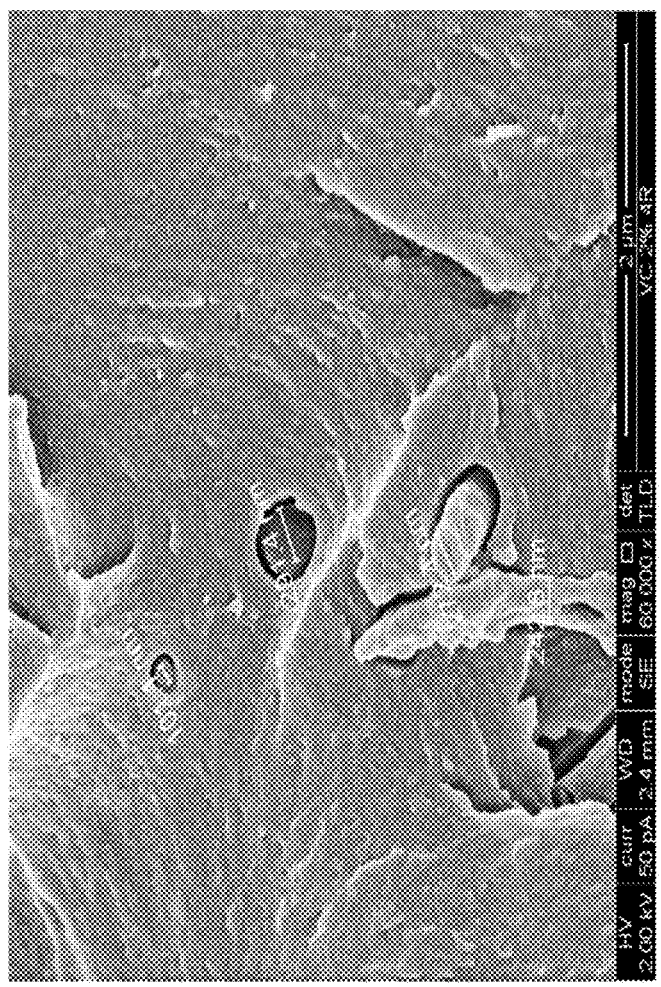
FIG. 27 presents a SEM image showing protein fibers in VeroClear having 2% enrichment. Scale bar is 2 μm.
Figure 29C:
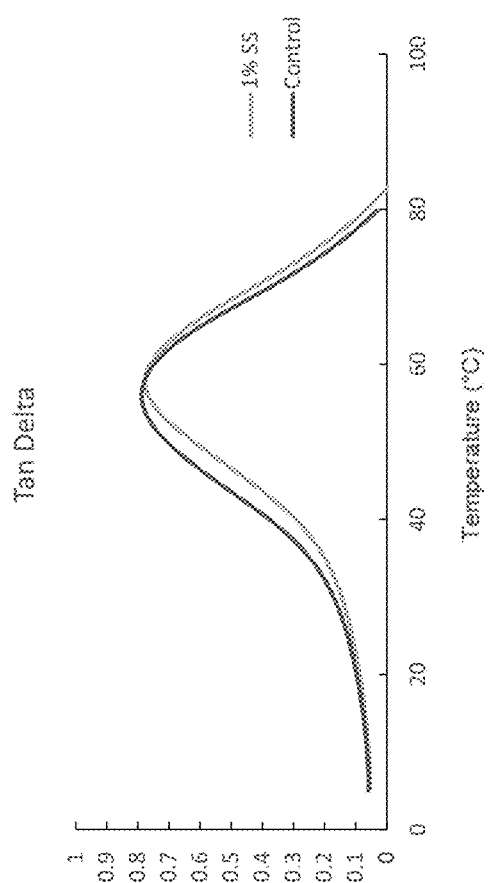

FIG. 26 presents an agglomerate of fibers in pHEMA. FIG. 27 presents fibers in VeroClear 2% enrichment. FIG. 28 presents SEM images of lyophilized fibers. FIGS. 29A-C present a dynamic mechanical analysis (DMA) of VeroClear enrichment of a sample reference (storage modulus vs Temp). The graphs show a shift in glass transition of ~3° as seen on the peak of the Tan Delta graph. The same Overall behavior is derived from small enrichment amount. Overall an improved modulus is derived from enrichment.

Example 6

Cross-Linking of the Synthetic Fibers

Additional exemplary procedures were aimed at creating longer continuous fiber based on spider-silk in order to reach textile end properties to allow weaving into threads, cables etc. The process is based on wet chemistry, using cross-linkers in a solution based on inorganic buffers in different pH levels. The fibers are added to the buffer for dispersion, cross-linking agent is then added. Process parameters such as pH level, cross-linker concentration, temperature, incubation time influence the degree of cross-linking achieved. Process parameters such as injection process with varying injection speeds allow crosslinking agent contacting the fibers in order to create a continuous process for fiber production is developed. Other processes that are spinneret based processes like wet-spinning, dry-spinning, gel-spinning can also be used as production processes for fiber production. The following Cross-linking agents are utilized in water-based reactions, some are performed using organic solvents as detailed below Exemplary Procedures with EDC/NHS:

Materials: EDC (1-ethyl-3-[3-dimethylaminopropyl]carbodiimide hydrochloride); NHS (N-hydroxysuccinimide); Conjugation buffer: Phosphate-buffered saline (PBS), 100 mM sodium; phosphate, 150 mM NaCl; pH 7.2; and Activation buffer: 0.1M MES, 0.5M NaCl, pH 6.0.

Methods: In exemplary procedures, mix of proteins for cross linking was prepared by immersing amount of ~5 mg in activation buffer. EDC and NHS were then added to the buffer to create the reactive ester group which allows for amine reaction with that group resulting in an amide bond. A conjugation buffer was added to the buffer to increase the pH and the efficiency of the reaction. The reaction time was 10 minutes at RT (25° C.).

Results: As cross-linking and aggregation could lead to similar behavior, control batches were prepared and examined as well. While aggregates can be broken with Vortex or with small impact on the slide the crosslinked proteins remained stable.

Figure 30:
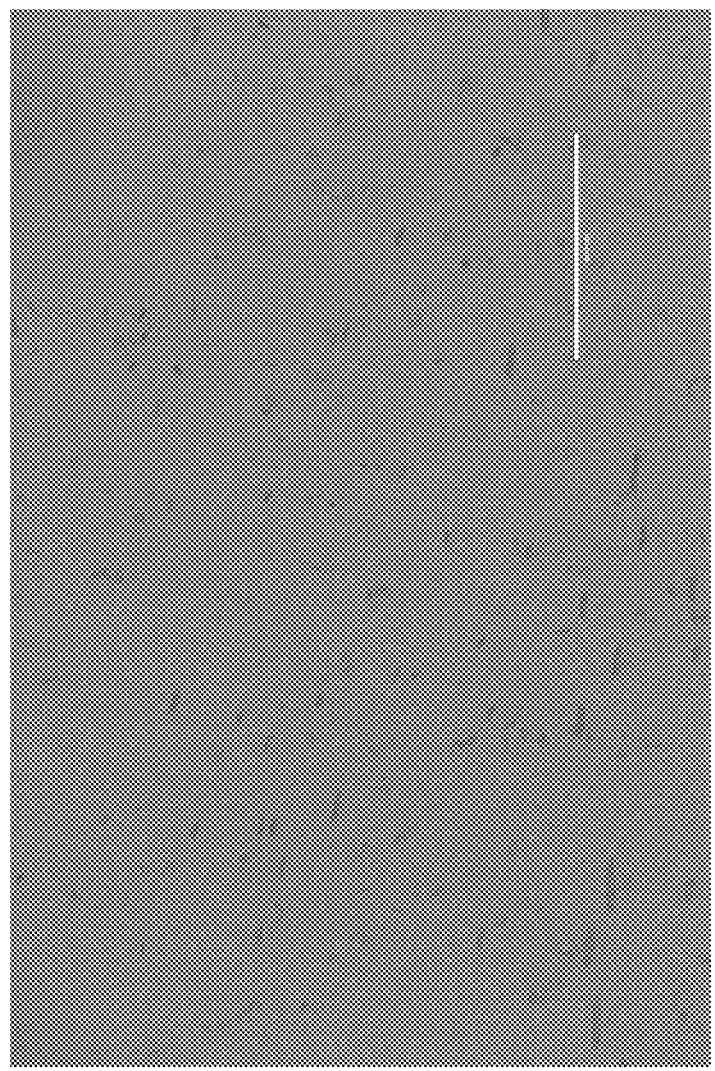
FIG. 30 presents a microscopic examination of fibers in an activation buffer before the reaction as described in Examples section (e.g., Example 6) below (bar is 400 μm).
Figure 31:
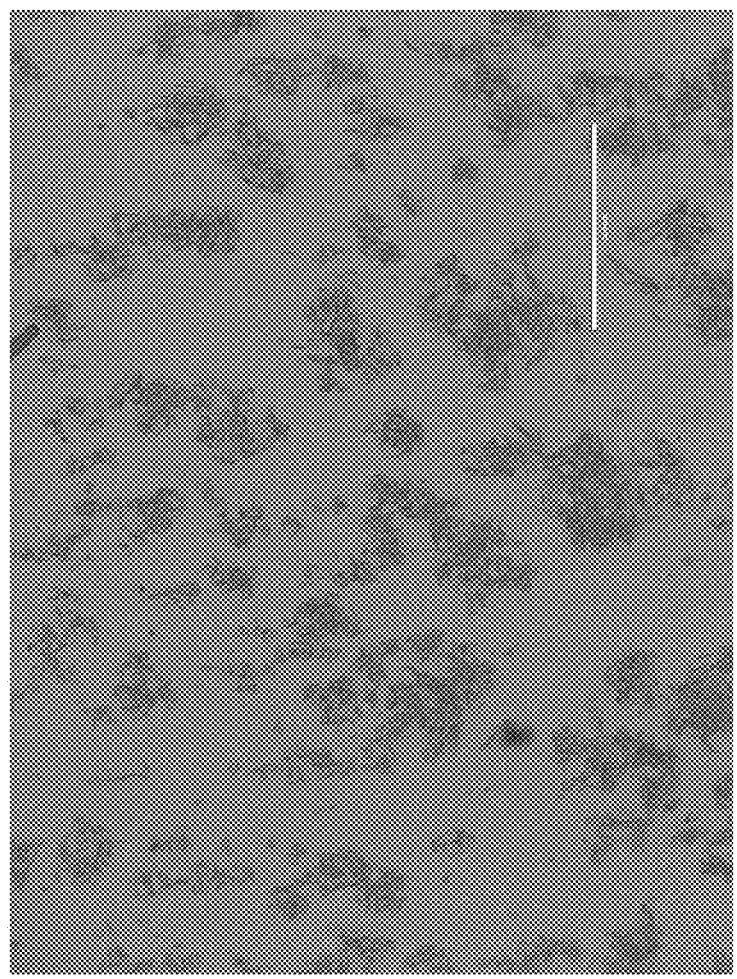
FIG. 31 presents a microscopic examination of fibers in conjugation buffer, after 10 min in reaction as described in the Examples section (e.g., Example 6) below (bar is 400 μm).
Figure 32:
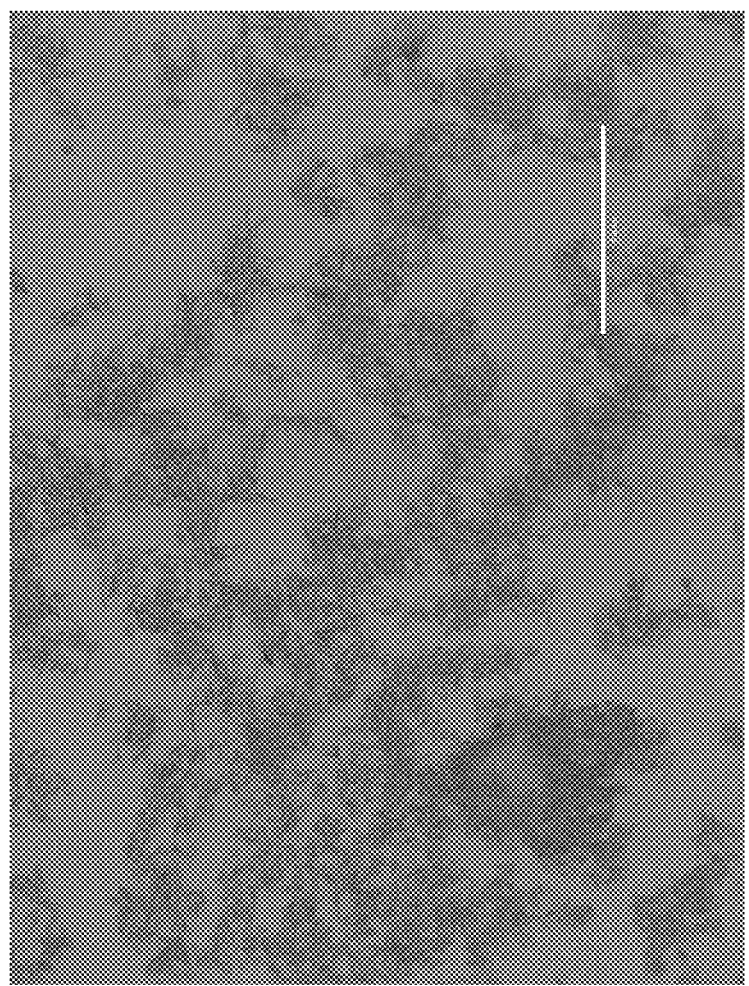
FIG. 32 presents a microscopic examination of fibers in conjugation buffer after 30 min as described in the Examples section (e.g., Example 6) below (bar is 400 μm).
Figure 33:
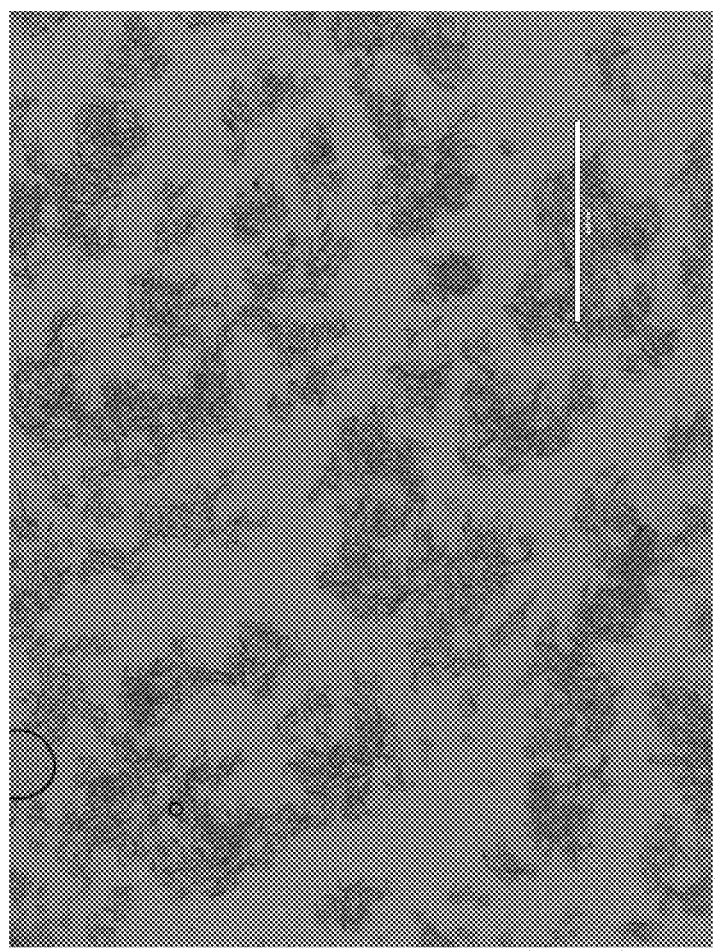
FIG. 33 presents a microscopic examination after operating vortex on the activation buffer as described in the Examples section (e.g., Example 6) below. No changes in the shape and size of the fibers are observed (bar is 400 μm).

FIG. 30 presents a microscopic examination of fibers in activation buffer before the reaction (bar is 400 µm). FIG. 31 presents a microscopic examination of fibers in conjugation buffer, after 10 min in reaction (bar is 400 µm). FIG. 32 presents a microscopic examination of fibers in conjugation buffer after 30 min (bar is 400 µm). FIG. 33 presents a microscopic examination after operating vortex on the activation buffer. No change in the shape and size of the fibers are observed (bar is 400 µm).

Example 7

Covalent Coating

Materials and Methods:

| Material | Manufacturer |
|---|---|
| EDC, (1-ethyl-3-[3-dimethylaminopropyl]carbodiimide hydrochloride), | Merck Milipore |
| NHS, (N-hydroxysuccinimide) | Merck Milipore |
| CDI | Merck Milipore |
| MES buffer, 0.1M, 0.15% NaCl | Self-prepared |
| PBS buffer, 0.1M | BI |

A substrate's surface was coated with covalently bonded Spidersilk. In exemplary procedures, silicon surface was activated by piranha solution followed by 3-Aminopropyl triethoxysilane (APTES) treatment, for amine group anchoring. In exemplary procedures, piranha solution was prepared by mixing 30 ml $H_2SO_4$ 98% and 10 ml $H_2O_2$ (30%) slowly. Surfaces were immersed to be treated to the piranha solution for surface activation for 30 minutes and were then washed with double distilled water (DDW). Surface activation was tested by water droplet test.

APTES surface treatment: solution was prepared by the following recipe: 68.25 ml of Ethanol; 3.75 ml of DDW; 3 ml of acetic acid. Right before immersing the slides 2 ml of APTES was added. Surfaces were immersed to be treated to the solution followed by putting in vacuum oven at 60° C., 100 mbar for 20 minutes, vacuum oven at 120° C., 100 mbar for 1 h and then washing with ethanol, drying and putting back in oven. In additional exemplary procedures, the substrate's surface was thereafter inserted in double distilled water (DDW), as described below.

Water phase Fiber Dope Solution: 10 mg of Spidersilk fibers were put in 5 ml PBS 0.1M buffer. 3 slides were immersed 30 min with continuous stirring.

Organic phase Fiber Dope Solution: 10 mg of Spidersilk fibers were inserted in in 5 ml DMSO. 3 slides were immersed for 30 min with continuous stirring.

Crosslinking water phase solution: 5 ml of IVIES 0.1M+ 0.15M NaCl, pH6 were added to 200 mg of EDC and 130 mg Sulfo-NHS.

EDC, NHS or sulfo-NHS were equilibrated to room temperature before opening containers. 3 slides were immersed overnight with continuous stirring.

Crosslinking organic phase solution: In 5 ml of Dimethyl sulfoxide (DMSO) 50 mg of CDI were added. CDI was equilibrated to room temperature before opening container. 3 slides were then immersed overnight with continuous stirring.

Figure 35:
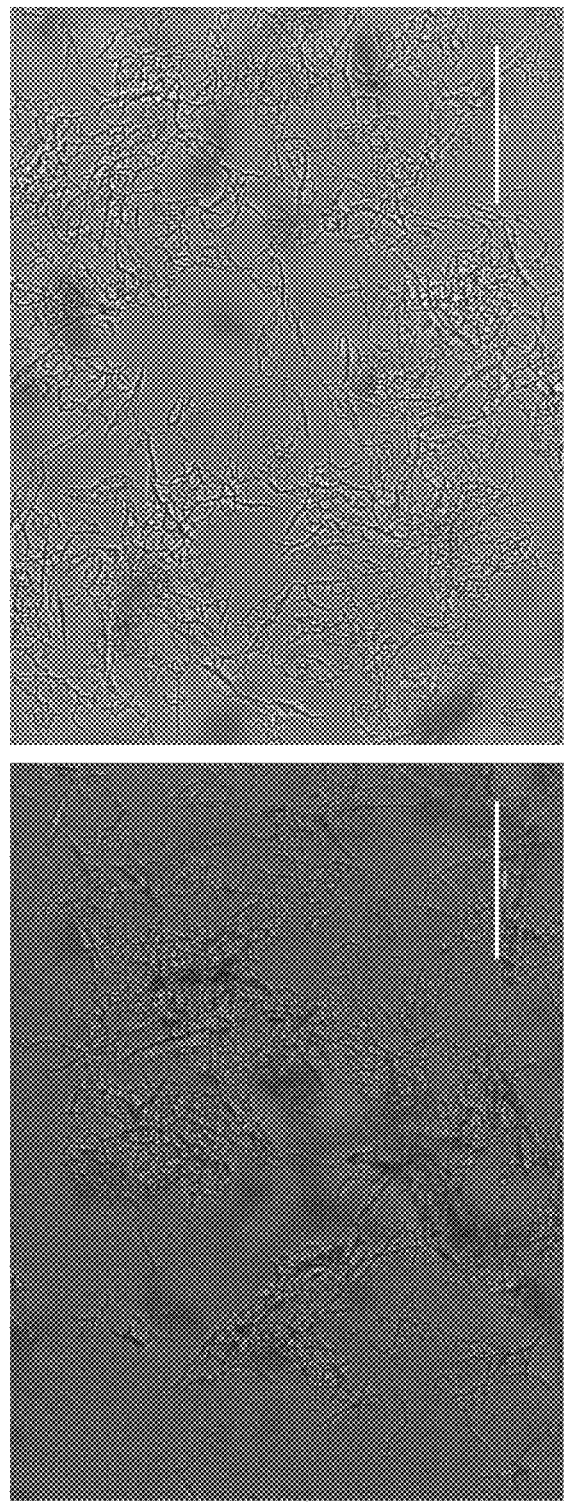
FIG. 35 presents a closer look at microscopic images of the coated silicon (organic phase on the left, aqueous phase on the right).

FIG. 34 presents microscopic images of the coated silicon (organic phase on the left, aqueous phase on the right). FIG. 35 presents a closer look at microscopic images of the coated silicon (organic phase on the left, aqueous phase on the right).

Example 8

Wetting Study of SS in ESEM

Materials and methods: Several samples were prepared: Lyophilized SS fibers dispersed in ethanol, and deposited on cover slip and air-dried; Lyophilized SS fibers spread on carbon tape; Lyophilized SS fibers spread on quartz sheet; and cellulose fibers dispersed in ethanol and deposited on a cover slip as a control experiment.

Measurement was performed on FEI Quanta 200F ESEM, where water droplets were spread around the sample upon entering the vacuum chamber. By increasing the chamber pressure water was evaporated and condensed on the sample holder allowing to measure dynamic wetting behavior.

Results: The two main imaging methods for wettability study at high spatial resolution are the atomic force microscopy (AFM) and the environmental scanning electron microscopy (ESEM). The AFM provides wettability study of nano-scale droplets over solid surfaces being limited to time resolution of a few minutes while wetting study by ESEM is usually restricted to micron-size droplets over bulk surfaces with 1 s time resolution.

In-situ condensation and evaporation experiments in ESEM on smooth and textured bulk surfaces provides static contact angles as well as retarding and advancing angles by analysis of reflected secondary electrons due to electron-specimen interaction.

The ESEM provides a high spatial resolution and a relatively large depth of field of tens microns, which has been required for characterization of the rough surface of fibrous materials before and after in-situ droplet condensation. By dropping a few water droplets in the vicinity of the sample and by increasing the chamber pressure one can condense water on the sample during the measurement enabling the measurement of contact angle on small surface. The viewing angle of the water droplets is critical in order to correctly analyze the shape and angle of the drop. The droplets are not equal in volume however when enough drops are used for the calculation one can study the variation.

To correctly calculate the contact angle, the angle of the image is sideways viewed and not exactly above the drop. Also, several assumptions are taken in consideration including spherical shape of the drop which is not always the case.

Figure 36:
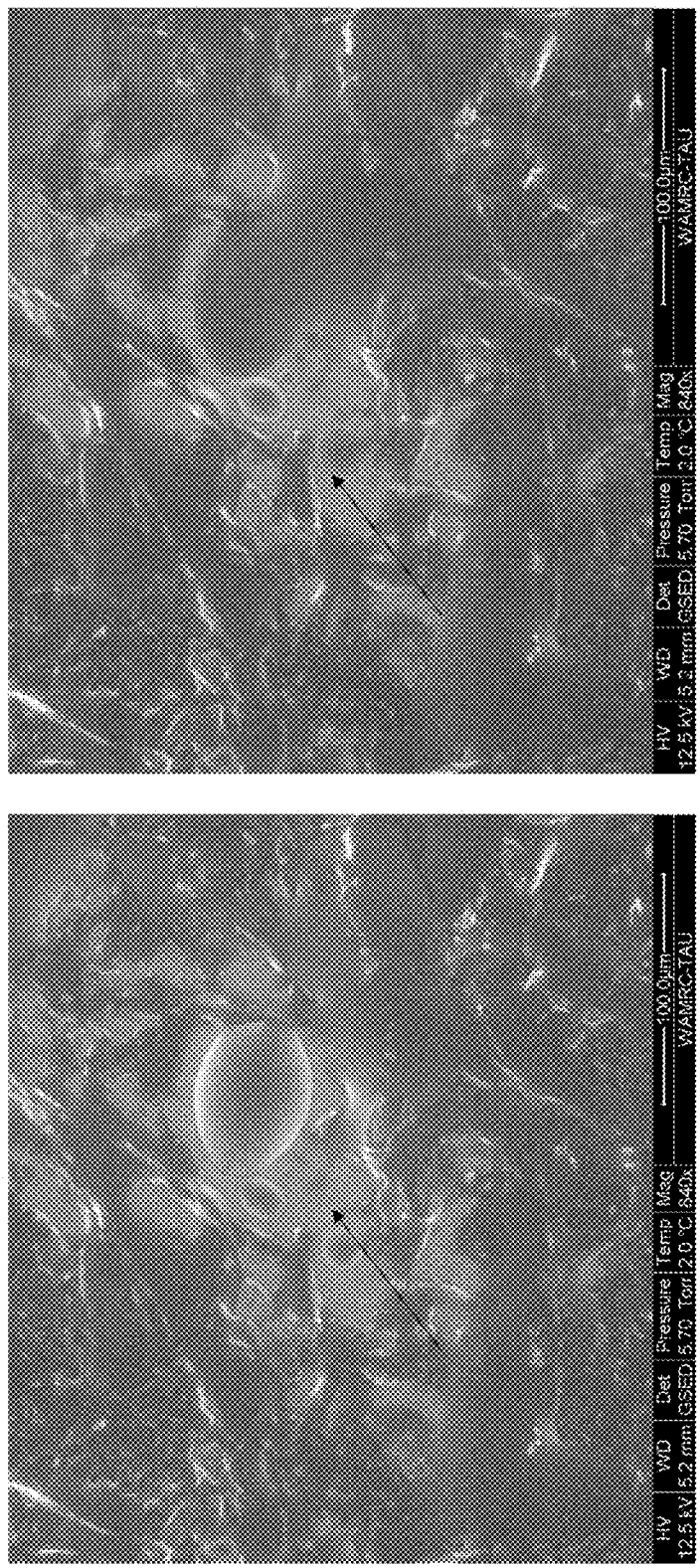
FIG. 36 presents environmental scanning electron microscopy (ESEM) images showing a large droplet before (left) and upon reaching a fiber coated surface (right). Arrow points to one droplet in transition. White lines/ribbons are the contour, the bulk of the fiber is darker.
Figure 38:
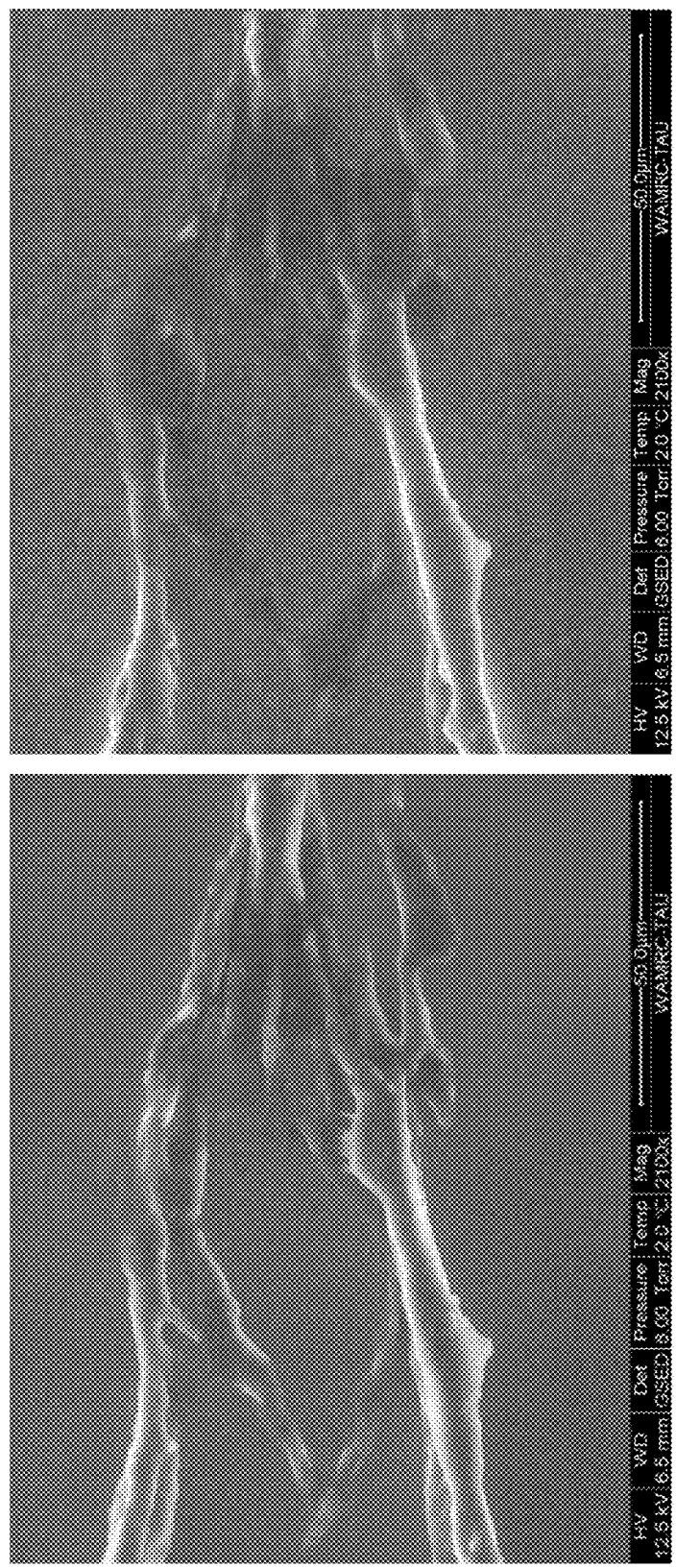
FIG. 38 presents ESEM images showing water level rising and wetting the fibers causing a darker hallo around the fibers. Water droplets are clearly seen around the fibers on the right image with no droplets formation on the surface. Bars are 50 μm.
Figure 39:
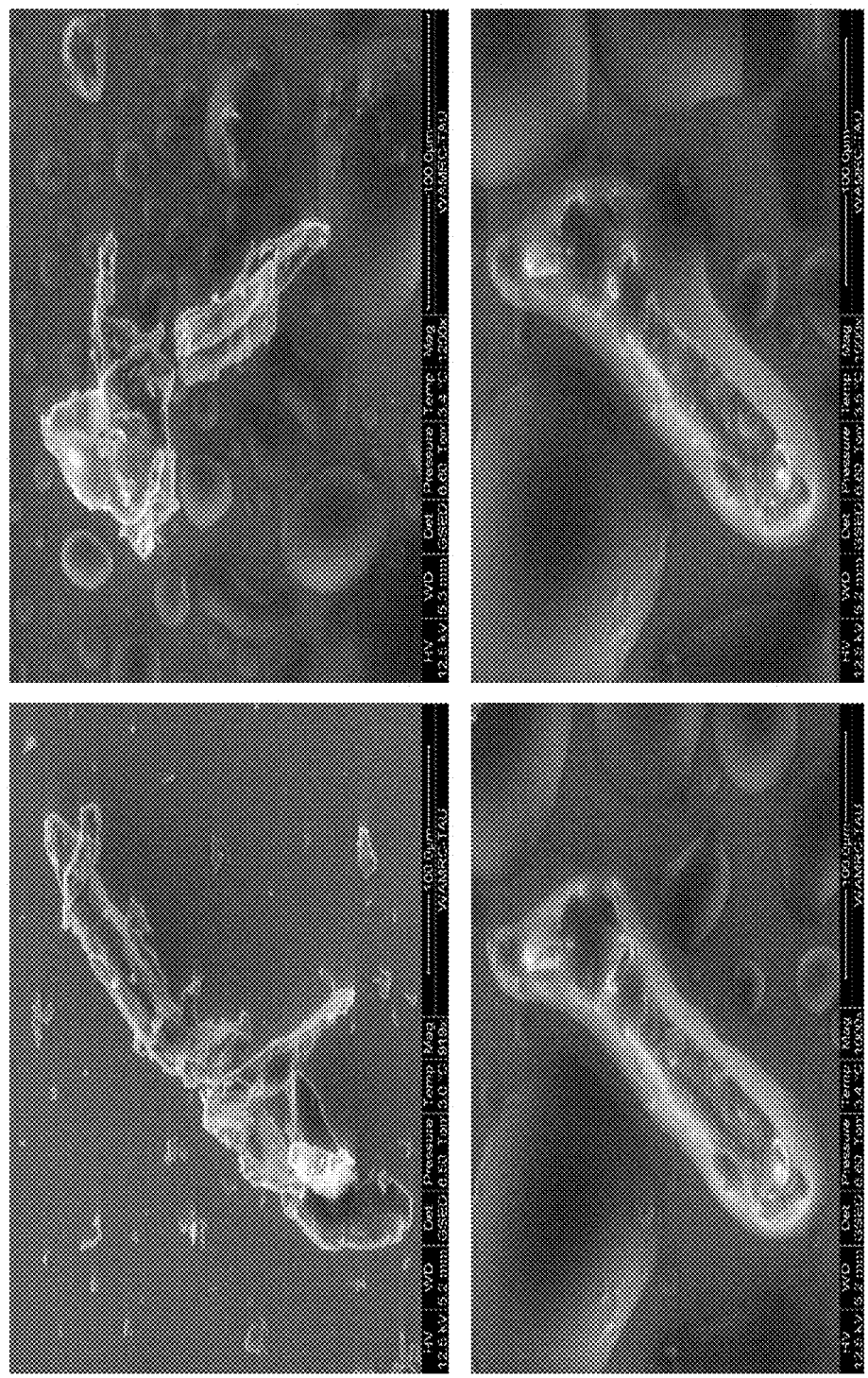
FIG. 39 presents ESEM images of cellulose fibers showing water condensation around the fibers not on the fiber surface. Lower panels demonstrate water in good wetting with cellulose and less absorption by cellulose. Bars are 100 μm.
Figure 40A:
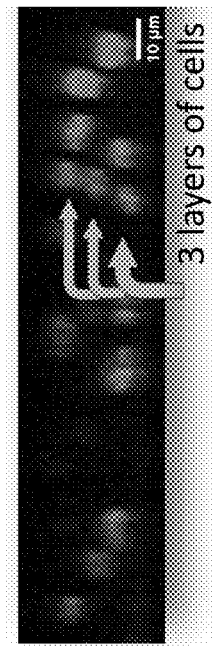
FIGS. 40A-B present steps for analysis of fiber thickness and number of cell layers: The blue channel (DAPI) was used to count the number of L929 layers in the orthogonal view of a defined cluster (FIG. 40A); 23 areas containing clusters of cells and were selected for analysis. The edges of the chosen regions were enhanced and the image was converted into binary mode. The maximal z points of each coordinates were set into a graph, and the average thickness was calculated. The upper panel of FIG. 40B presents the orthogonal view of SS coating (DAPI+bright field) in a selected area; the middle panel presents the conversion of bright field signal to binary mode, indicating the coordinates of the SS; and the graph in the lower panel shows the quantitation of binarized bright field signal indicating the thickness of the SS coating.
Figure 40B:
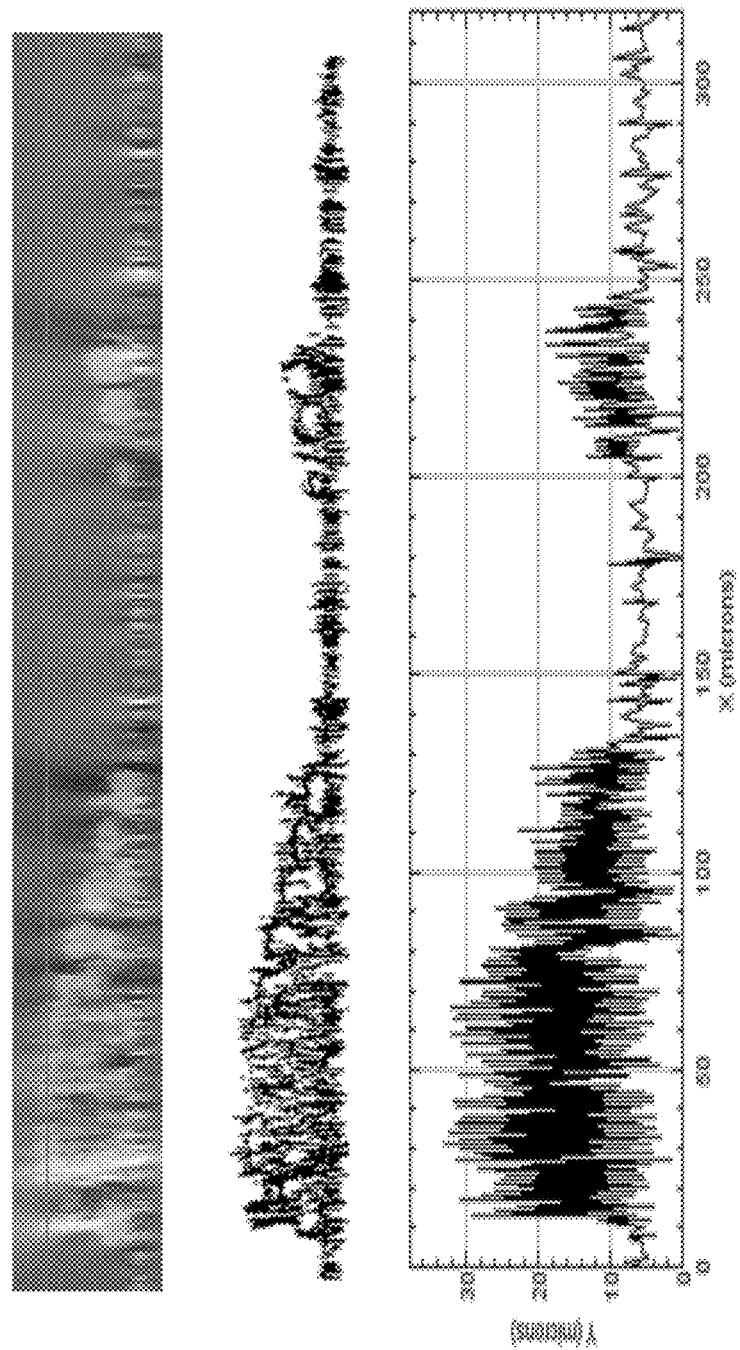
Figure 41B:
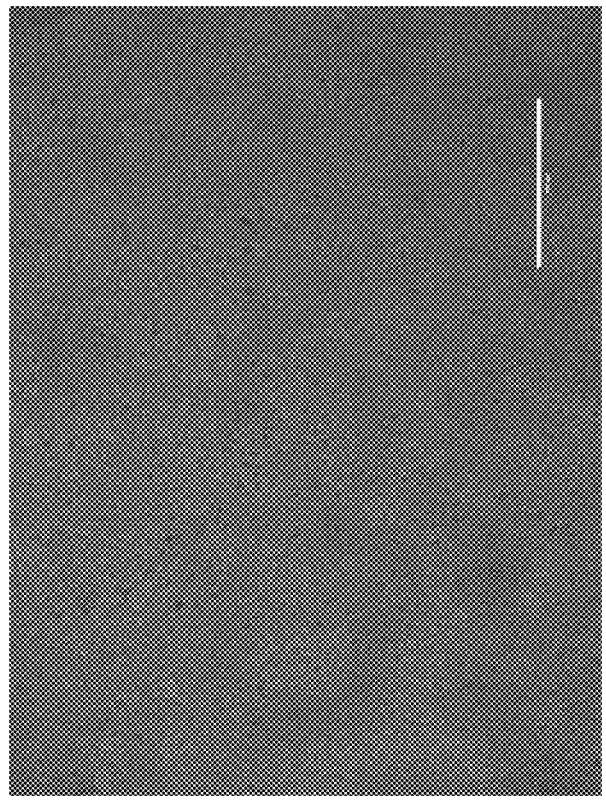
FIGS. 41A-B present HEK293 cells adopt 3D growth as well as unique migration pattern when seeded on SS at high density 5 days after seeding (FIG. 41A) vis-à-vis a control of collagen (FIG. 41B) (Bars are 400 μm).
Figure 41A:
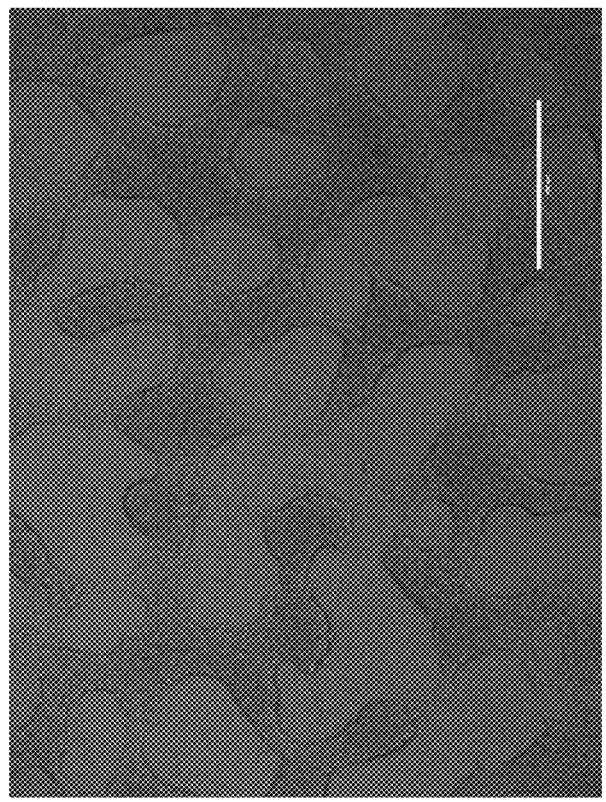
Figure 42:
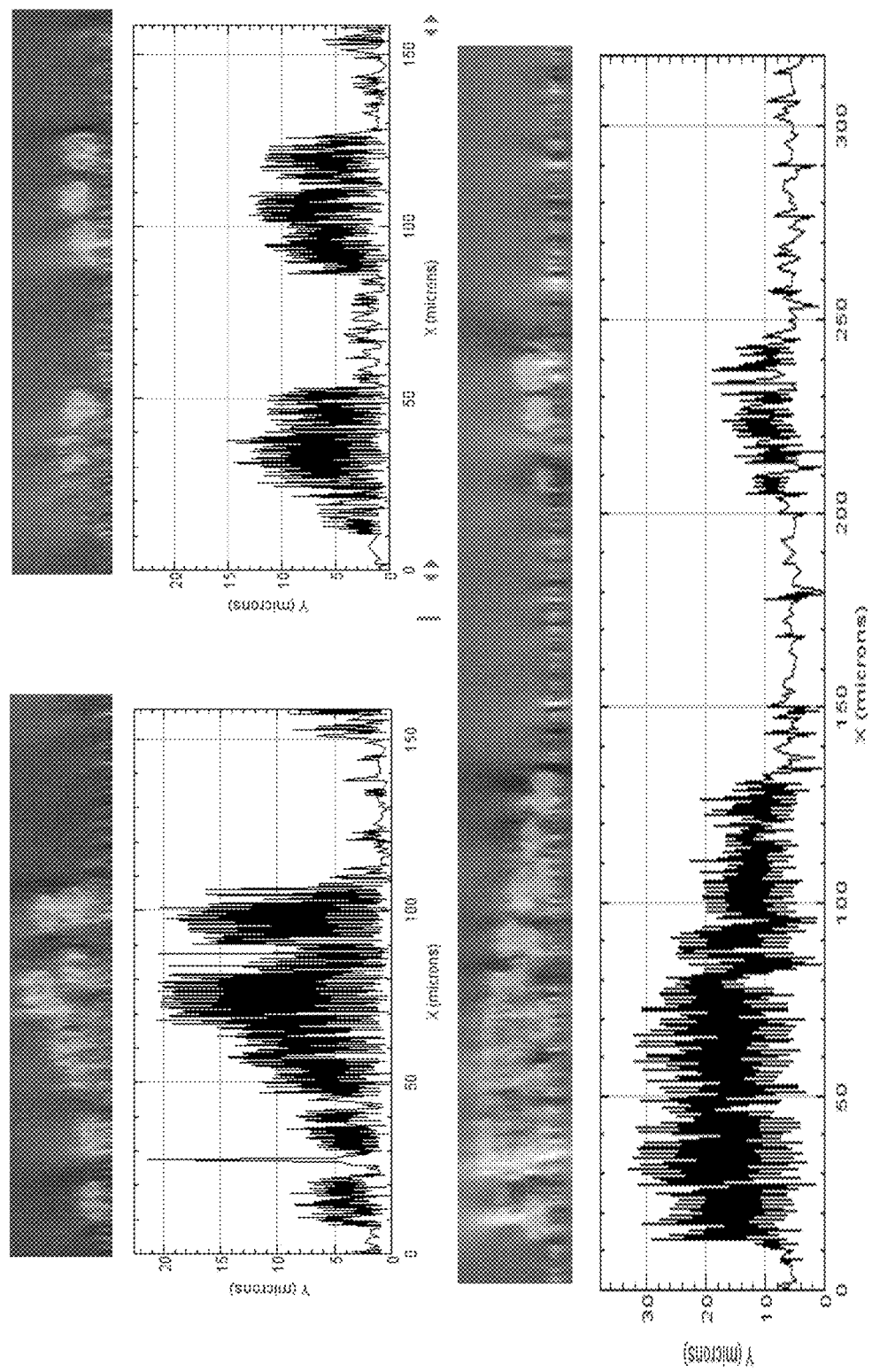
FIG. 42 presents analysis (similarly to FIG. 40B) of fiber thickness, showing representative fields used for quantification to examine the layer of cells growth of on SS.

As set upon to study the SS behavior in dynamic wetting it was observed that that no droplets formed on the fiber surface hinting at either a very small wetting angle or hygroscopic behavior of the fibers acting as a "sponge" absorbing the condensed water in the sample holder, as shown in FIG. 36. Each row in FIG. 36 represents a different time line whereas time progresses one can see the droplets increase in size. Several observations were found: As the droplets reach the surface of the fibers they immediately break and wet them; Water condensation occurs on the substrate surface and not on the fibers as seen in several images, leading to the conclusion that either the fibers are absorbing the water droplets or they are too high in volume as to condense on the nano-filament based structure of SS (see FIG. 37); As time progresses the water reaches and gathers around the fibers leading to a more dark appearance until full immersion is obtained (see FIG. 38). A similar behavior was observed for the cellulose control leading to the same conclusion can be seen in FIG. 39. The similar behavior of cellulose in the wetting stage is in agreement with this conclusion that porous structures are difficult to measure wetting angles on. However, cellulose fibers had contracted a white halo around them, while SS fibers absorbed the water seen as more darker areas as shown in the FIGS. 38 and 39. This wetting experiment shows that SS fibers are "sponge-like" fibers with very high affinity for water absorbance compared to cellulose.

Example 9

Assessment of 3D Cell Growth on Spider Silk

In exemplary procedures, the assessment of 3D cell growth on spider silk was performed in several aspects: morphology, attachment, proliferation and comparison to 2D growth of cells on uncoated culture dish and collagen coated culture dish.

Materials, Equipment and Disposables:

| Material | Manufacturer | Cat. No. |
|---|---|---|
| NCTC clone 929 (L929) | ATCC | CCL-1 |
| MEM-NEAA, Earle's salts, non-essential amino acids | Biological Industries | 01-040-1A |
| Donor Horse Serum (DHS) | Biological Industries | 04-004-1A |
| Phosphate Buffered Saline (PBS) | Biological Industries | 02-023-1A |
| Sodium Pyruvate | Biological Industries | 03-042-1B |
| L-glutamine | Biological Industries | 03-020-1B |
| Penicillin-Streptomycin-Amphotericin | Biological Industries | 03-033-1B |
| Trypsin EDTA Solution B (0.25%), EDTA (0.05%) | Biological Industries | 03-052-1B |
| Trypan Blue, 5 mg/ml in Saline | Biological Industries | 03-102-1B |

| Equipment | Manufacturer | Model/Cat No. |
|---|---|---|
| Laminar flow cabinet, Biological hazard | Labcono | Purifier class ii biosafety cabinet delta series |
| Inverse phase contrast microscope | Life Technologies | EVOS XL |
| Incubator, 37° C., humidified, 5% CO$_2$ | Heraeus | Hera Cell |
| Water bath, 37° C. | QSR Technologies | VMS-20 |
| Hemocytometer | Marienfeld | Neubauer - improved |
| Nunc ™ Cell Culture Treated EasYFlasks ™ | Thermo Fisher Scientific | 156472 |
| 96-well tissue culture microtiter plate-coated with SS | Seevix Material Sciences Ltd. | NA |
| 24-well tissue culture plate-coated with SS | Seevix Material Sciences Ltd. | NA |
| Pipettes | Eppendorf | Research Plus |
| 8-12 channel pipettes | Labnet International, Inc. | BioPette PLUS |
| Pipette aid | VMR | Accurpette |
| 1 ml, 5 ml, 10 ml Disposable Polystyrene Serological Pipettes | Greiner Bio One | 07-200-571, 07-200-573, 07-200-574 |
| 10 µl, 100 µl, 1000 µl pipette tips | Axygen | T-10-CRS, T-200-CRS, T-1000-CRS |

Culturing L929 and other cells: In exemplary procedures, L929 were cultured in MEM-NEAA medium supplemented with 10% DHS, 2 mM L-glutamine, 1 mM sodium pyruvate, 100 U/ml Penicillin, 0.1 mg/ml Streptomycin and 0.25 µg/ml Amphotericin.

Removal of cells from the culture flask dish by enzymatic digestion: In exemplary procedures, the medium was removed from cells cultured in a T75 flask with a serological pipette and discard. The cell monolayer was washed with 4 ml PBS to remove serum. 2 ml was added to trypsin/EDTA to the cell monolayer and swirl flask to cover the entire surface. The flask was returned to the incubator for 5-10 minutes until cells were detached. The cells were resuspended in 10 ml of fresh, serum-containing medium to inactivate the trypsin, and triturated 5 times with a serological pipette to separate the cells from each other.

50 μl of the cells were mixed with 50 μl 5 mg/ml trypan blue, and 10 μL of the mixture was applied to a hemocytometer. Cells were verified to be mostly separated and viability is >95% (Dead cells are distinguished from viable cells by their uptake of trypan blue stain). Cells were then counted.

Seeding Cells on Spider Silk (SS) Coated Plates:

96 well plates: Cells were diluted with fresh media to a density of 200,000 L929 cells/ml. 200 μl of the cell suspension were added to the designation wells and were placed in a humidified 37° C. incubator, 5% $CO_2$ (final seeding concentrations: 40,000 cells/well).

24 well plates: Cells were diluted with fresh media to a density of 240,000 L929 cells/ml. 1 ml of the cell suspension was added to the designation wells and was placed in a humidified 37° C. incubator, 5% $CO_2$ (final seeding concentrations: 240,000 cells/well). As a control for normal cell growth the cells were seeded at the same concentration on collagen-coated or un-coated plates.

Culture was grown up to 10 days. For long-term culture of strongly adherent cells, the cell culture medium was semi-exchanged every 2-3 days. The Plate was tilt and half of the old culture medium was very carefully aspirated with a pipette tip and discarded. An equal amount of fresh medium was added to each well.

Assessment of the 3D-Growth of Cells on SS:

Cells seeded on SS divide and grow laterally as well as in 3 dimensional structures, forming viable cell clusters. Growth and morphology of culture are examined every day using an inverted microscope. Cells are observed using a microscope under different magnifications and different focus planes. Starting from the bottom of the culture dish, the dial is slowly turned to focus on a higher plane. Clusters formed by cells seeded on SS is viewed on several focus planes, revealing the contour of different cells at each focus level.

Figure 43:
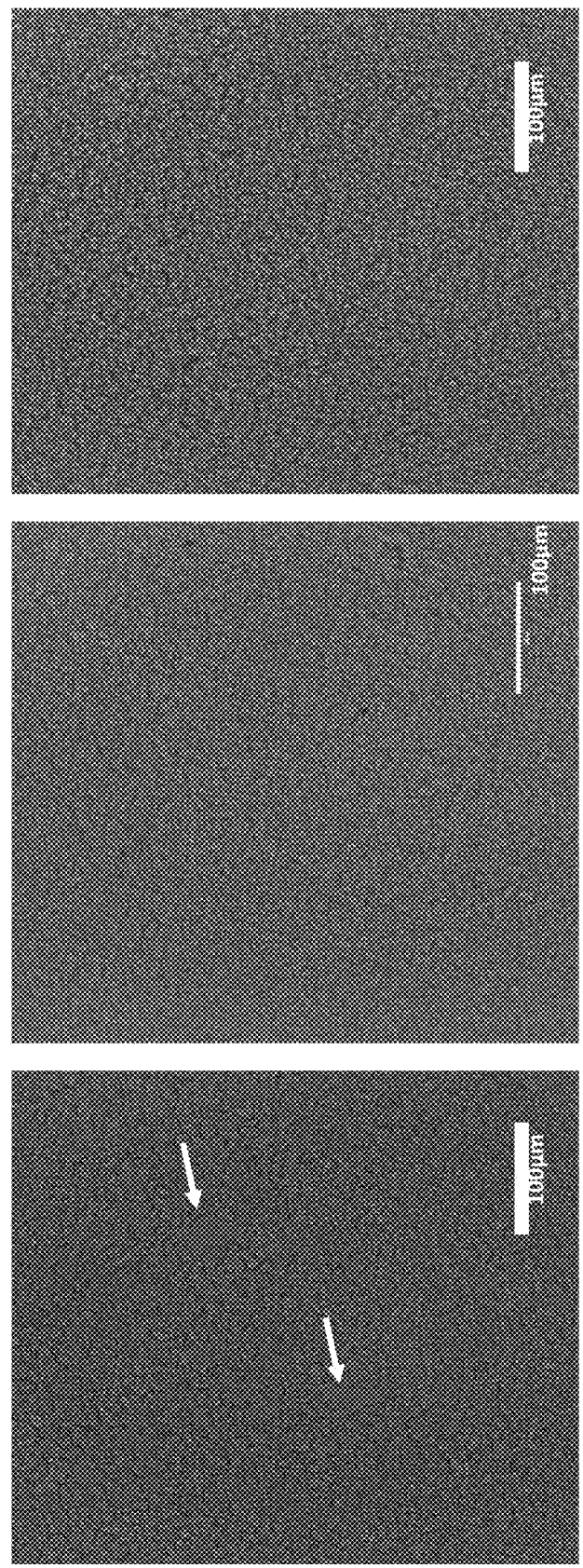
FIGS. 43A-C present microscopic examination showing TC plate coated with different concentrations of SS. left panel: 1 layer, ~6×10⁵ fibers/cm² (FIG. 43A); middle panel: 2 layers, ~12×10⁵ fibers/cm² (FIG. 43B); right panel: ~24× 10⁵ fibers/cm² (FIG. 43C). Different concentrations of fibers produce different number of layers, enabling different phenotypic growth of cells. Arrows in FIG. 43A point at holes in the surface coating, indicating coating defects caused by a limit in the number of fibers. Coating with this amount of fibers (6×10⁵/cm²) results in an average of 1 layer of fibers in the coating.

The results obtained from these experiments indicated that while collagen supported the growth of a single layer of cells SS supported the growth of 2-5 layers of cells. (See FIG. 40A, 40B and FIGS. 41A-B, 42), and depending on the thickness of SS applied to the plate (FIGS. 43A-C). Thus, the present system allows pre-fabrication of a set number of layers of cells wherein the cells cross interact. Specifically, it is shown that a plate covered with $1-6 \times 10^5$ fibers/$cm^2$ supported only a single layer wherein $12 \times 10^5$ fibers/$cm^2$ supported the growth of two layers of cells (at least 80% of the layers were organized in two layers). $24 \times 10^5$ fibers/$cm^2$ supported the growth of an average of 3.7 layers of cells (at least 80% of the layers were, organized in 3-4 layers). Again, in these settings the collagen coated plates yielded only a single layer regardless of the thickness of the collagen applied (data not shown).

Figure 44:
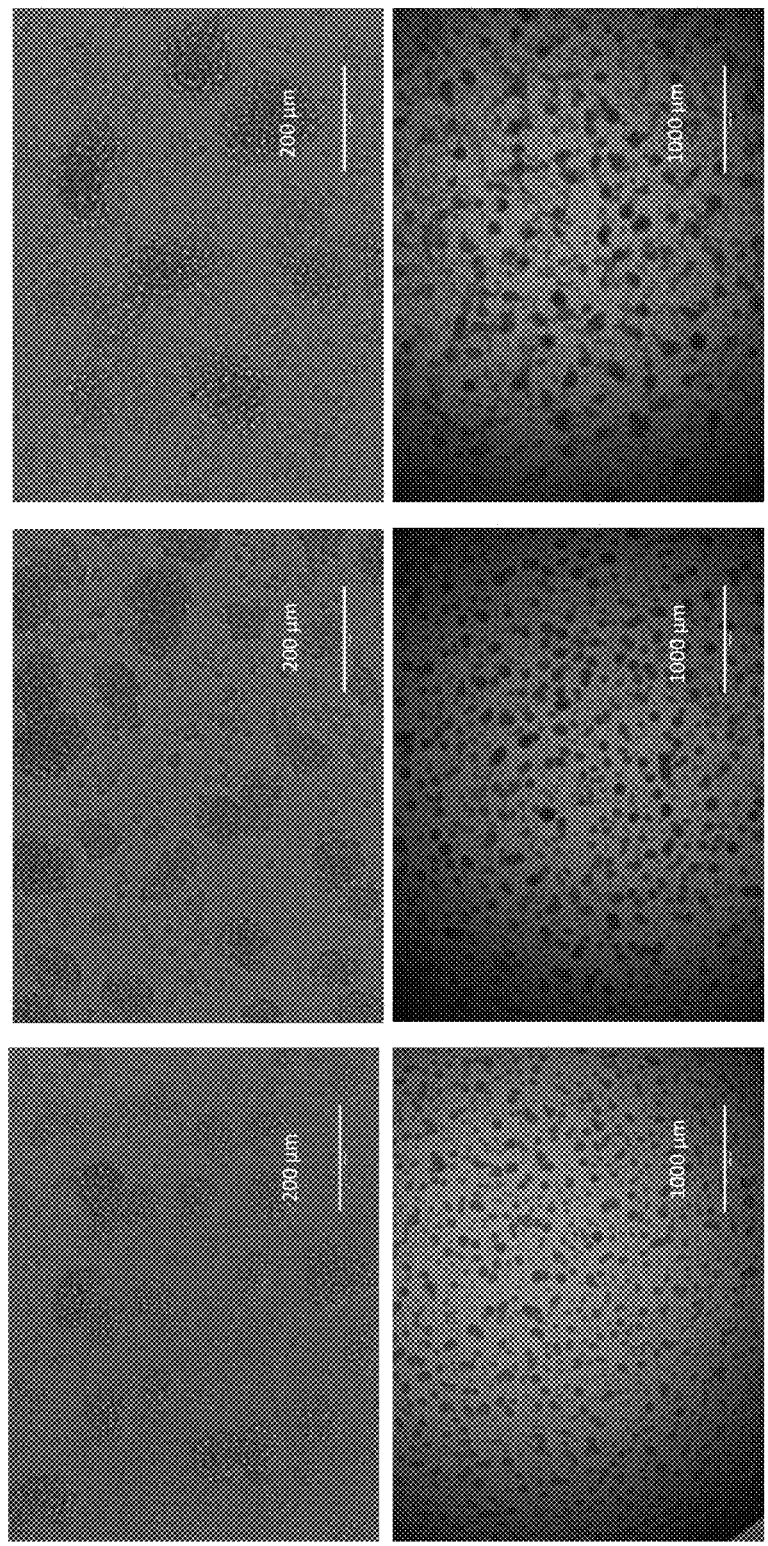
FIG. 44 presents microscopic examination showing the amount of fibers per a certain area and the resulted number of layers. 3D structures are growing and start to connect: left panels: 3$^{rd}$ day post seeding; middle panels: 5$^{th}$ day post seeding; right panels: 7$^{th}$ day post seeding. Bars: upper panel: 200 μm, lower panel: 1000 μm.

As shown in FIG. 44 cells seeded on plates coated with SS compared to solitary cell organization within control plates (seeded with the same amount of cells) not only formed multilayers with cell-to-cell interactions but actually organized in a connective tissue structure or micro-structure. In this set of experiments it was clearly shown that the motility of cells grown on SS is at least 2 times higher than cells grown on collagen coated, polystyrene tissue culture dish (see also FIGS. 49A-C).

Figure 45:
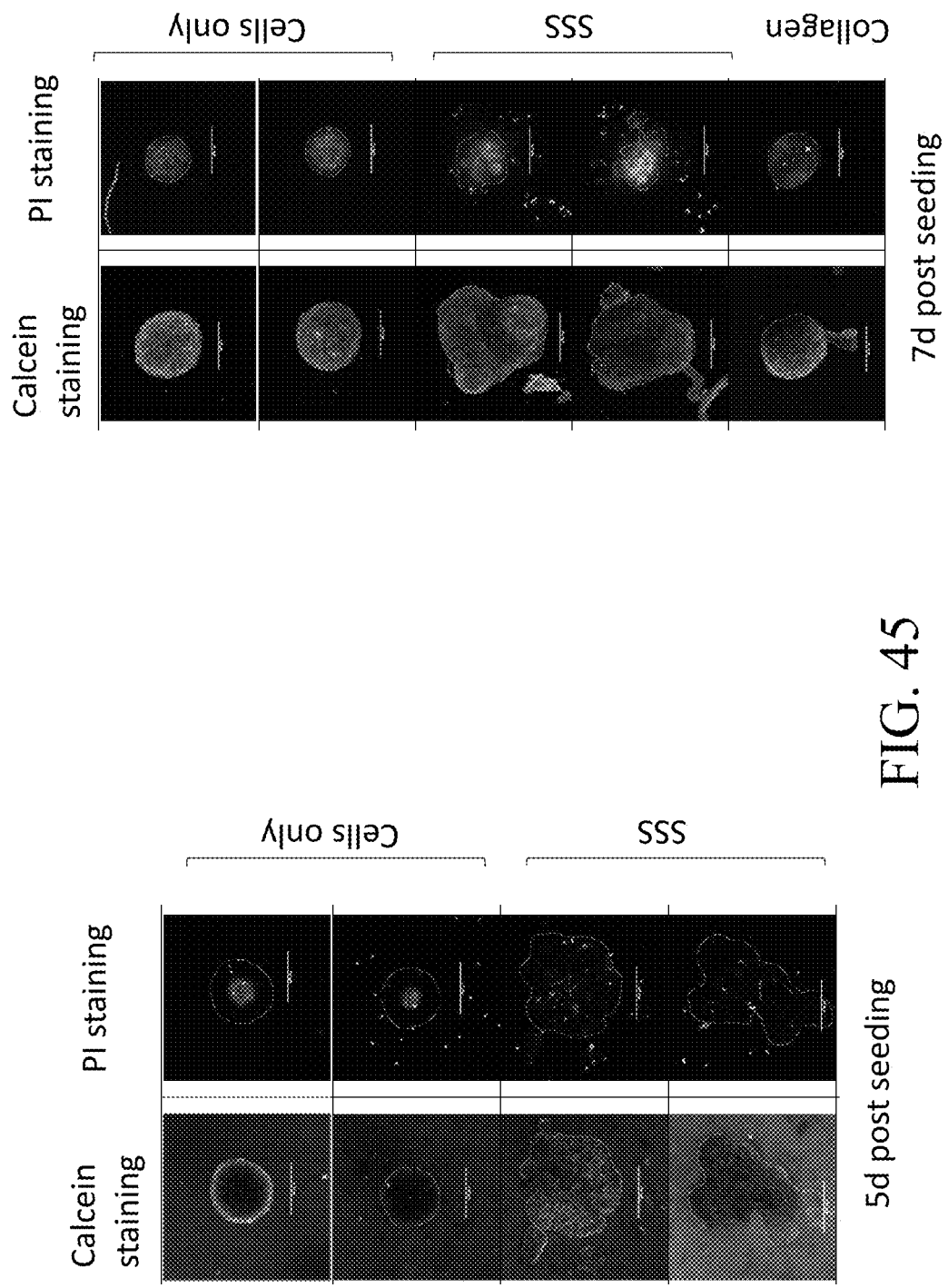
FIG. 45 is confocal imaging of spheroids stained with calcein and propidium iodide demonstrating that cells (L929) seeded on Nunclon™ Sphera™ Microplates (designed for spheroid formation) generate spheroids with unique different characteristics in the presence of SS. 5000 cells were seeded in each well. Left panel: 5 days post seeding, right panel: 7 days post seeding. The stacked pictures of each channel were analyzed to determine the maximal area of the spheroid (Calcein staining) and the area of the necrotic core (PI staining).
Figures 46A, 46B, 46C:
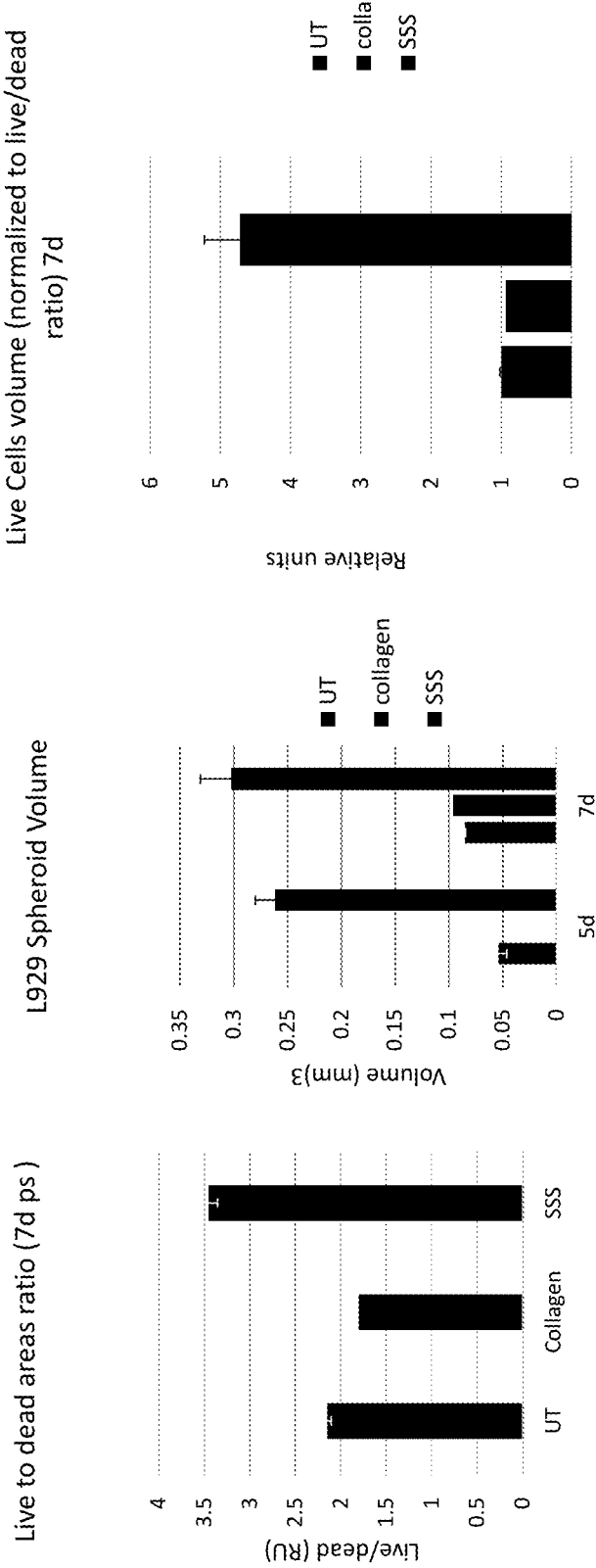
FIGS. 46A-C are bar graphs showing size and live/necrotic zones analysis of L929 cells.

As shown in FIG. 45 cells seeded on spheroids-inducing plates, in the presence of SS developed into spheroids which are significantly larger than cells seeded (with the same amount of cells) in the presence of collagen or without a supplement. After 7 days of incubation the SS-containing spheroids maintained about 4.7 more viable cells compared to the collagen-spheroids or control spheroids without a supplement. The surface area of the spheroids grown with SS was about 4.1 times bigger compared to the surface area of the spheroids cultured with collagen or without a supplement. These experiments not only show that SS strongly support proliferation of cells but also inhibit cell death within spheroids as shown in FIGS. 46A-C.

In summary, these data provide conclusive evidence regarding the unexpected benefits of SS in growing and maintaining cells. Surprisingly it was found that at least 4 repeats (n) were required in order to maintain cell viability and proliferation. The recent results also indicated that preferably 8 or more repeats should be used in order to maximize cell growth parameters.

Example 10

Seeding Cells on the Spider Silk (Ss) of Coated Plates and Seeding Cells Mixed with Ss on Uncoated Plates HEK293 cells were seeded on plates coated with SS and on naked plates wherein SS was mixed with the cell culture media.

The following cell culture materials were used:

| Material | Manufacturer | Cat. No. |
|---|---|---|
| SS- Spider Silk Suspension, Sterile, 150,000 Units/μl | Seevix Material Sciences Ltd. | NA |
| HEK293 cells | ATCC | CRL-1573 |
| Dulbecco's Modified Eagle Medium, without L-glutamine | Biological Industries | 01-055-1A |
| Phosphate Buffered Saline (PBS) | Biological Industries | 02-023-1A |
| Fetal Bovine Serum (FBS) | Biological Industries | 04-121-1A |
| L-glutamine | Biological Industries | 03-020-1B |
| Penicillin-Streptomycin-Amphotericin | Biological Industries | 03-033-1B |
| Trypsin EDTA Solution B (0.25%), EDTA (0.05%) | Biological Industries | 03-052-1B |
| Trypan Blue, 5 mg/ml in Saline | Biological Industries | 03-102-1B |

| Equipment | Manufacturer | Model/Cat No. |
|---|---|---|
| Laminar flow cabinet, Biological hazard | Labconco | Purifier class ii biosafety cabinet delta series |
| Inverse phase contrast microscope | Life Technologies | EVOS XL |
| Incubator, 37° C., humidified, 5% $CO_2$ | Heraeus | Hera Cell |
| Water bath, 37° C. | QSR Technologies | VMS-20 |
| Hemocytometer | Marienfeld | Neubauer - improved |
| Nunc ™ Cell Culture Treated EasYFlasks ™ | Thermo Fisher Scientific | 156472 |
| 96-well tissue culture microtiter plate-coated with SS | Seevix Material Sciences Ltd. | NA |
| 24-well tissue culture plate-coated with SS | Seevix Material Sciences Ltd. | NA |

| Equipment | Manufacturer | Model/Cat No. |
|---|---|---|
| Pipettes | Eppendorf | Research Plus |
| 8-12 channel pipettes | Labnet International, Inc. | BioPette PLUS |
| Pipette aid | VMR | Accurpette |
| 1 ml, 5 ml, 10 ml Disposable Polystyrene Serological Pipettes | Greiner Bio One | 07-200-571, 07-200-573, 07-200-574 |
| 10 µl, 100 µl, 1000 µl pipette tips | Axygen | T-10-CRS, T-200-CRS, T-1000-CRS |

HEK293 cell culture procedure: HEK293 were cultured in Dulbecco's Modified Eagle Medium supplemented with 10% FBS, 2 mM L-glutamine, 100 U/ml Penicillin, 0.1 mg/ml Streptomycin and 0.25 µg/ml Amphotericin. Cells were removed from the culture flask dish by enzymatic digestion. Followed by washings and resuspension in fresh serum-containing medium to inactivate the trypsin. The cells were then mixed with trypan blue and viability was assessed.

Seeding cells on SS coated plates: Cells were diluted in fresh media to a density of 50,000 HEK293 cells/ml and to a density of 200,000 cells/ml. 200 µl of the cell suspension were added to designated cell-culture wells and were placed in a humidified 37° C. incubator, 5% $CO_2$ (Final seeding concentrations: 10,000 cells/well and 40,000 cells/well). Cells were grown for up to 6 days without medium replacement.

Cells grown in SS enriched medium: Cells were diluted in fresh media to a density of 50,000 HEK293 cells/ml and to a density of 200,000 cells/ml. SS was added to the suspended cells at a final concentration of 400,000 units of SS/ml (2.5 µl S/ml). 200 µl of the SS-cell suspension were added to designated cell-culture wells and were placed in a humidified 37° C. incubator, 5% $CO_2$ (Final seeding concentrations: 10,000 cells/well and 40,000 cells/well). Cells were grown for up to 6 days without medium replacement.

Results

Figure 47A:
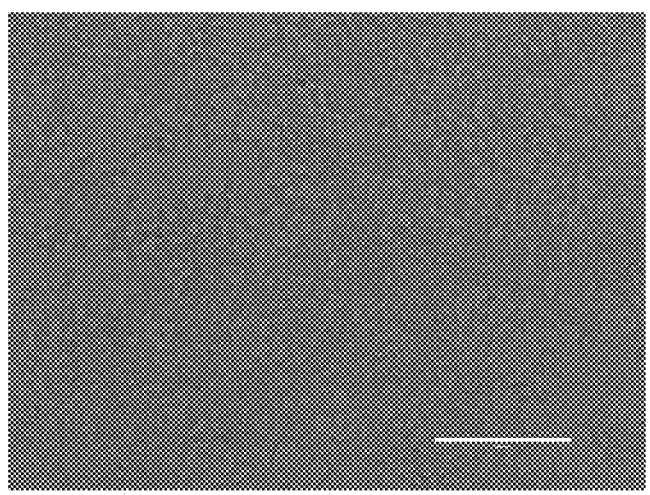
FIGS. 47A-C show microscopic images demonstrating low density seeding of HEK293 mixed with SS, (compared to control of cells seeded without SS (FIG. 47A): lower focus plane (FIG. 47B) upper focus plane (FIG. 47C). Scale bars are 200 μm.
Figure 47B:
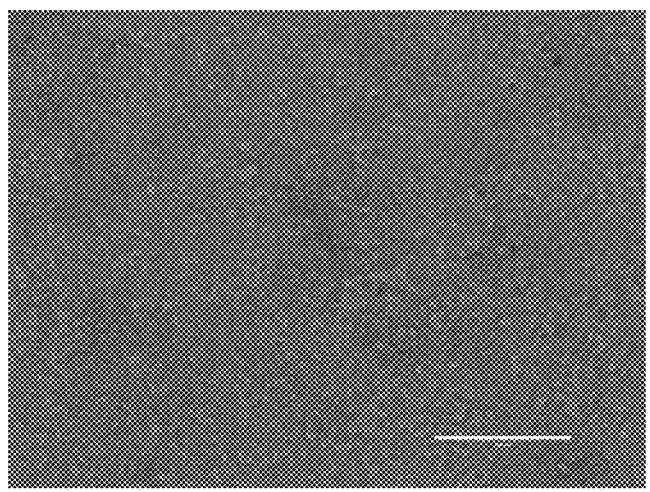
Figure 47C:
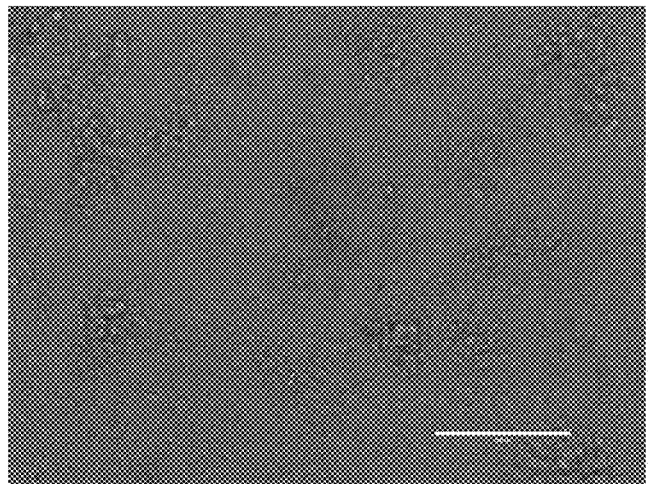

Cells seeded on SS coated plates: Clusters of HEK293 were observed 3-4 days cell seeding. Both high density and low density cells seeded on ss coating were shown to organize in a multilayer 3D structure (FIG. 47A) within 5 days after seeding. Control cells seeded on uncoated plates, grew as a monolayer (FIG. 47B). Cell death was less than 5%. In most fields 3 or more layers of cells were observed.

Figures 48A, 48B, 48C:
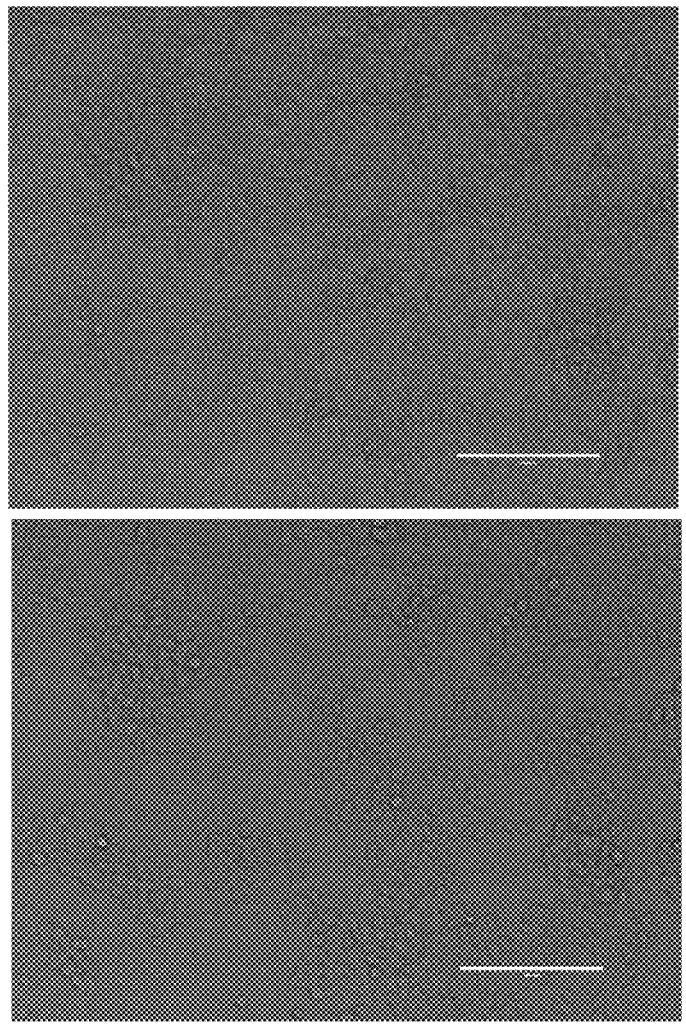
FIGS. 48A-C show images demonstrating 3D growth pattern of HEK293 cells when seeded on an SS coated plate, 5000 cells/well, 4 days post seeding: uncoated (FIG. 48A); lower plane (FIG. 48B), and upper plane (FIG. 48C).

Cells grown in media enriched with SS on "naked" plates: Clusters of HEK293 were observed 3-4 days after seeding cells were shown to adhere to the fibers. As shown in FIGS. 48A-C many cells were grown without any physical attachment to the plate. These cells were adhered to the SS. Not only that SS supported the cells attachment surface but also cells adhered to the SS proliferated through the SS fibers increasing the height of the clusters. Thus, cells which require attachment were grown on fibers which were partially attached to the plate or to other cells attached to the plate.

Figures 49A, 49B:
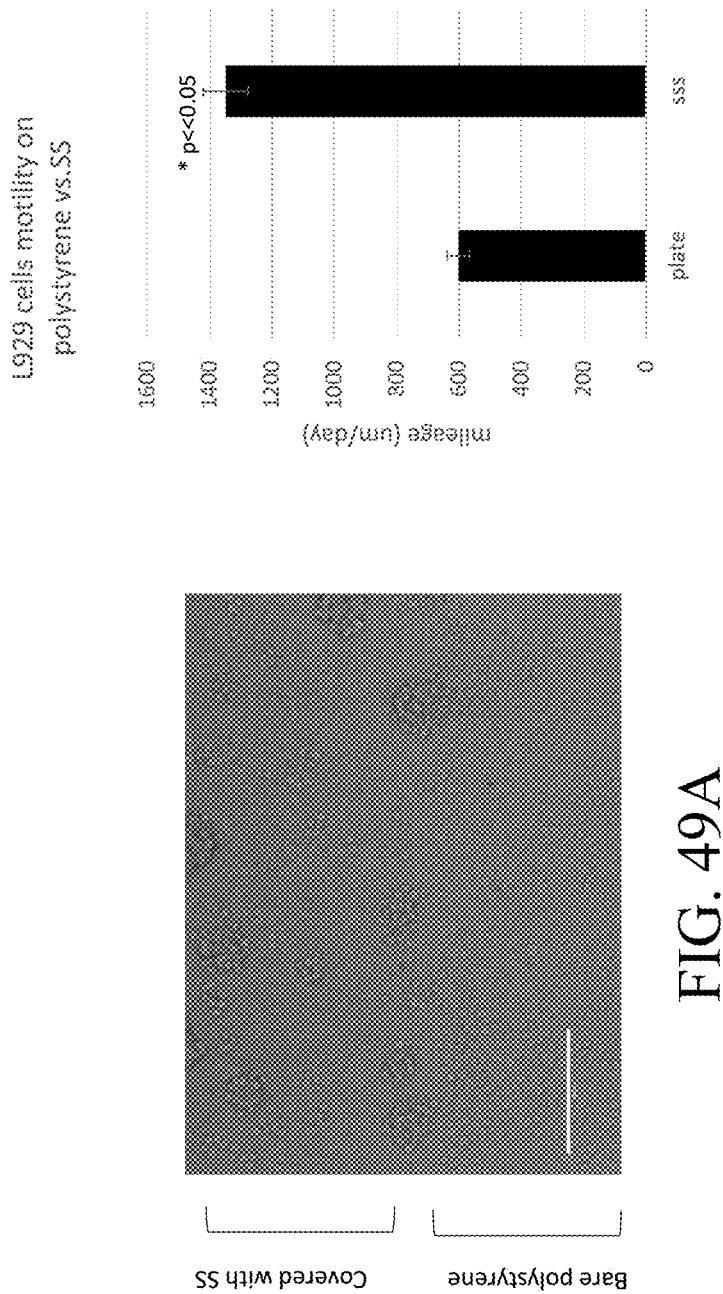
FIGS. 49A-B present cell motility quantification comparison between L929 cells seeded on polystyrene and cells seeded on SS-coated plates as visualized in microscope (FIG. 49A), and in bar graphs showing cells migration on polystyrene vs. SS (FIG. 49B).

FIGS. 49A-B present cell motility quantification—comparison between cells seeded on polystyrene and cells seeded on SS-coated plates. A tissue culture dish was partially coated with SS. L929 cells were seeded at a density of 70,000 cells/well. In the part coated with SS cell clusters were formed, while a monolayer was observed in the uncoated part. A series of time lapse pictures of the border of the two parts were taken, and motility of single cells was analyzed. The average motility of a cell cultured on SS is 2.2-fold higher than the motility of cells cultured on the uncoated polystyrene surface. Moreover, high motility of cells seeded on SS positively correlates to the density of the cell clusters.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A composition comprising: (a) a fiber comprising "m" types of proteins of differing molecular weight, wherein each protein in said "m" proteins comprises, independently, "n" repeats of a repetitive sequence of a major ampullate spidroin (MaSp) protein, wherein m and n are, independently, an integer between 2 to 70, said protein are of differing molecular weight and a different number of said repetitive sequence, said repetitive sequence comprises an amino acid sequence as set forth in SEQ ID NO: 1: $(X_1)_Z$ $X_2GPGGYGPX_3X_4X_5GPX_6GX_7GGX_8GPGGPGX_9X_{10}$, wherein $X_1$ is, independently, at each instance A or G wherein at least 50% of $(X_1)Z$ is A, Z is an integer between 5 to 30; $X_2$ is S or G; $X_3$ is G or E; $X_4$ is G, S or N; $X_5$ is Q or Y; $X_6$ is G or S; $X_7$ is P or R; $X_8$ is Y or Q; $X_9$ is G or S; and $X_{10}$ is S or G; and (b) a biocompatible material, cell culture media, cells, or any combination thereof.

2. The composition of claim 1, wherein said biocompatible material is a tissue scaffold, a medical device, wound care dressing, or a surgical suture.

3. The composition of claim 1, wherein said mixture of proteins is characterized by one or more properties selected from the group consisting of:
   a. each repeat has a molecular weight in the range of 2 kDa to 3.5 kDa; and
   b. the ratio of 'n' to 'm' is in the range of 1.5:1 to 1:1.5.

4. The composition of claim 1, wherein said repetitive region comprises the amino acid sequence as set forth in SEQ ID NO: 3 (AAAAAAAASGPGGYGPGSQGPSGPG-GYGPGGPGSS).

* * * * *

SEQUENCE LISTING

```
<160> NUMBER OF SEQ ID NOS: 17

<210> SEQ ID NO 1
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MISC_FEATURE
<222> LOCATION: (2)..(2)
<223> OTHER INFORMATION: X is S or G
<220> FEATURE:
<221> NAME/KEY: MISC_FEATURE
<222> LOCATION: (10)..(10)
<223> OTHER INFORMATION: X is G or E
<220> FEATURE:
<221> NAME/KEY: MISC_FEATURE
<222> LOCATION: (11)..(11)
<223> OTHER INFORMATION: X is G, S or N
<220> FEATURE:
<221> NAME/KEY: misc_feature
<222> LOCATION: (12)..(12)
<223> OTHER INFORMATION: Xaa can be any naturally occurring amino acid
```

```
<220> FEATURE:
<221> NAME/KEY: MISC_FEATURE
<222> LOCATION: (15)..(15)
<223> OTHER INFORMATION: X is G or S
<220> FEATURE:
<221> NAME/KEY: MISC_FEATURE
<222> LOCATION: (17)..(17)
<223> OTHER INFORMATION: X is P or R
<220> FEATURE:
<221> NAME/KEY: MISC_FEATURE
<222> LOCATION: (20)..(20)
<223> OTHER INFORMATION: X is Y or Q
<220> FEATURE:
<221> NAME/KEY: MISC_FEATURE
<222> LOCATION: (27)..(27)
<223> OTHER INFORMATION: X is G or S
<220> FEATURE:
<221> NAME/KEY: MISC_FEATURE
<222> LOCATION: (28)..(28)
<223> OTHER INFORMATION: X is S or G

<400> SEQUENCE: 1

Xaa Xaa Gly Pro Gly Gly Tyr Gly Pro Xaa Xaa Xaa Gly Pro Xaa Gly
1               5                   10                  15
Xaa Gly Gly Xaa Gly Pro Gly Gly Pro Gly Xaa Xaa
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic

<400> SEQUENCE: 2

Ser Gly Pro Gly Gly Tyr Gly Pro Gly Ser Gln Gly Pro Ser Gly Pro
1               5                   10                  15
Gly Gly Tyr Gly Pro Gly Gly Pro Gly Ser Ser
            20                  25

<210> SEQ ID NO 3
<211> LENGTH: 35
<212> TYPE: PRT
<213> ORGANISM: Artificial Sequence
<220> FEATURE:
<223> OTHER INFORMATION: Synthetic

<400> SEQUENCE: 3

Ala Ala Ala Ala Ala Ala Ala Ser Gly Pro Gly Gly Tyr Gly Pro
1               5                   10                  15
Gly Ser Gln Gly Pro Ser Gly Pro Gly Gly Tyr Gly Pro Gly Gly Pro
            20                  25                  30
Gly Ser Ser
        35

<210> SEQ ID NO 4
<211> LENGTH: 35
<212> TYPE: PRT
<213> ORGANISM: Artificial Sequence
<220> FEATURE:
<223> OTHER INFORMATION: Synthetic

<400> SEQUENCE: 4

Ala Ala Ala Ala Ala Ala Ala Ser Gly Pro Gly Gly Tyr Gly Pro
1               5                   10                  15
Glu Asn Gln Gly Pro Ser Gly Pro Gly Gly Tyr Gly Pro Gly Gly Pro
            20                  25                  30
```

Gly Ser Ser
        35

<210> SEQ ID NO 5
<211> LENGTH: 40
<212> TYPE: PRT
<213> ORGANISM: Artificial Sequence
<220> FEATURE:
<223> OTHER INFORMATION: Synthetic

<400> SEQUENCE: 5

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val
        35                  40

<210> SEQ ID NO 6
<211> LENGTH: 50
<212> TYPE: PRT
<213> ORGANISM: Artificial Sequence
<220> FEATURE:
<223> OTHER INFORMATION: Synthetic

<400> SEQUENCE: 6

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val Arg Pro Leu Ser Asn Leu Asp Asn
        35                  40                  45

Ala Pro
    50

<210> SEQ ID NO 7
<211> LENGTH: 54
<212> TYPE: PRT
<213> ORGANISM: Artificial Sequence
<220> FEATURE:
<223> OTHER INFORMATION: Synthetic

<400> SEQUENCE: 7

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val Asp Pro Pro Gly Cys Arg Asn Ser
        35                  40                  45

Ala Arg Ala Gly Ser Ser
    50

<210> SEQ ID NO 8
<211> LENGTH: 97
<212> TYPE: PRT
<213> ORGANISM: Artificial Sequence
<220> FEATURE:
<223> OTHER INFORMATION: Synthetic

<400> SEQUENCE: 8

Val Ala Ala Ser Arg Leu Ser Ser Pro Ala Ala Ser Ser Arg Val Ser
1               5                   10                  15

```
Ser Ala Val Ser Ser Leu Val Ser Ser Gly Pro Thr Asn Gly Ala Ala
            20                  25                  30

Val Ser Gly Ala Leu Asn Ser Leu Val Ser Gln Ile Ser Ala Ser Asn
            35                  40                  45

Pro Gly Leu Ser Gly Cys Asp Ala Leu Val Gln Ala Leu Leu Glu Leu
 50                  55                  60

Val Ser Ala Leu Val Ala Ile Leu Ser Ser Ala Ser Ile Gly Gln Val
 65                  70                  75                  80

Asn Val Ser Ser Val Ser Gln Ser Thr Gln Met Ile Ser Gln Ala Leu
                85                  90                  95

Ser
```

<210> SEQ ID NO 9
<211> LENGTH: 114
<212> TYPE: PRT
<213> ORGANISM: Artificial Sequence
<220> FEATURE:
<223> OTHER INFORMATION: Synthetic

<400> SEQUENCE: 9

```
Gly Pro Ser Gly Pro Gly Ala Tyr Gly Pro Ser Pro Ser Ala Ser Ala
 1               5                  10                  15

Ser Val Ala Ala Ser Arg Leu Ser Ser Pro Ala Ala Ser Ser Arg Val
            20                  25                  30

Ser Ser Ala Val Ser Ser Leu Val Ser Gly Pro Thr Asn Gly Ala Ala
            35                  40                  45

Ala Val Ser Gly Ala Leu Asn Ser Leu Val Ser Gln Ile Ser Ala Ser
 50                  55                  60

Asn Pro Gly Leu Ser Gly Cys Asp Ala Leu Val Gln Ala Leu Leu Glu
 65                  70                  75                  80

Leu Val Ser Ala Leu Val Ala Ile Leu Ser Ser Ala Ser Ile Gly Gln
                85                  90                  95

Val Asn Val Ser Ser Val Ser Gln Ser Thr Gln Met Ile Ser Gln Ala
                100                 105                 110

Leu Ser
```

<210> SEQ ID NO 10
<211> LENGTH: 555
<212> TYPE: PRT
<213> ORGANISM: Artificial Sequence
<220> FEATURE:
<223> OTHER INFORMATION: Synthetic

<400> SEQUENCE: 10

```
Ala Ala Ala Ala Ala Ala Ser Gly Ser Gly Gly Tyr Gly Pro Glu
 1               5                  10                  15

Asn Gln Gly Pro Ser Gly Pro Val Ala Tyr Gly Pro Gly Gly Pro Val
            20                  25                  30

Ser Ser Ala Ala Ala Ala Ala Ala Gly Ser Gly Pro Gly Gly Tyr
            35                  40                  45

Gly Pro Glu Asn Gln Gly Pro Ser Gly Pro Gly Gly Tyr Gly Pro Gly
 50                  55                  60

Gly Ser Gly Ser Ser Ala Ala Ala Ala Ala Ala Ala Ser Gly Pro
 65                  70                  75                  80

Gly Gly Tyr Gly Pro Gly Ser Gln Gly Pro Ser Gly Pro Gly Gly Ser
                85                  90                  95
```

Gly Gly Tyr Gly Pro Gly Ser Gln Gly Pro Ser Gly Pro Gly Ala Ser
            100                 105                 110

Ser Ala Ala Ala Ala Ala Ala Ala Ser Gly Pro Gly Gly Tyr Gly
        115                 120                 125

Pro Gly Ser Gln Gly Pro Ser Gly Pro Gly Ala Tyr Gly Pro Gly Gly
            130                 135                 140

Pro Gly Ser Ser Ala Ala Ala Ser Gly Pro Gly Gly Tyr Gly Pro Gly
145                 150                 155                 160

Ser Gln Gly Pro Ser Gly Pro Gly Gly Tyr Gly Pro Gly
        165                 170                 175

Ser Gln Gly Pro Ser Gly Pro Gly Pro Gly Ala Ser Ala Ala Ala
        180                 185                 190

Ala Ala Ala Ala Ala Ala Ser Gly Pro Gly Gly Tyr Gly Pro Gly Ser
        195                 200                 205

Gln Gly Pro Ser Gly Pro Gly Ala Tyr Gly Pro Gly Gly Pro Gly Ser
210                 215                 220

Ser Ala Ala Ala Ser Gly Pro Gly Gly Tyr Gly Pro Gly Ser Gln Gly
225                 230                 235                 240

Pro Ser Gly Pro Gly Ala Tyr Gly Pro Gly Gly Pro Gly Ser Ser Ala
            245                 250                 255

Ala Ala Ala Ala Ala Gly Ser Gly Pro Gly Gly Tyr Gly Pro Gly
        260                 265                 270

Asn Gln Gly Pro Ser Gly Pro Gly Tyr Gly Pro Gly Gly Pro Gly
            275                 280                 285

Ser Ser Ala Ala Ala Ala Ala Ala Ser Gly Pro Gly Gly Tyr Gly
290                 295                 300

Pro Gly Ser Gln Gly Pro Ser Gly Pro Gly Val Tyr Gly Pro Gly Gly
305                 310                 315                 320

Pro Gly Ser Ser Ala Ala Ala Ala Ala Ala Gly Ser Gly Pro Gly
        325                 330                 335

Gly Tyr Gly Pro Gly Asn Gln Gly Pro Ser Gly Pro Gly Tyr Gly
            340                 345                 350

Pro Gly Gly Ser Gly Ser Ser Ala Ala Ala Ala Ala Ala Ala Ser
        355                 360                 365

Gly Pro Gly Gly Tyr Gly Pro Gly Ser Gln Gly Pro Ser Gly Pro Gly
    370                 375                 380

Gly Ser Gly Gly Tyr Gly Pro Gly Ser Gln Gly Pro Ser Gly Pro Gly
385                 390                 395                 400

Ala Ser Ser Ala Ala Ala Ala Ala Ala Ser Gly Pro Gly Gly
            405                 410                 415

Tyr Gly Pro Gly Ser Gln Gly Pro Ser Gly Pro Gly Ala Tyr Gly Pro
            420                 425                 430

Gly Gly Pro Gly Ser Ser Ala Ala Ala Ser Gly Pro Gly Gly Tyr Gly
        435                 440                 445

Pro Gly Ser Gln Gly Pro Ser Gly Pro Gly Ala Tyr Gly Pro Gly Gly
        450                 455                 460

Pro Gly Ser Ser Ala Ala Ala Ala Ala Ala Ser Gly Pro Gly Gly
465                 470                 475                 480

Tyr Gly Pro Gly Ser Gln Gly Pro Ser Gly Pro Gly Gly Ser Arg Gly
            485                 490                 495

Tyr Gly Pro Gly Ser Gln Gly Pro Gly Gly Pro Gly Ala Ser Ala Ala
            500                 505                 510

Ala Ala Ala Ala Ala Ala Ala Ser Gly Pro Gly Gly Tyr Gly Pro Gly

```
            515                 520                 525
Ser Gln Gly Pro Ser Gly Pro Gly Tyr Gln Gly Pro Ser Gly Pro Gly
        530                 535                 540

Ala Tyr Gly Pro Ser Pro Ser Ala Ser Ala Ser
545                 550                 555
```

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

```
His His His His His His
1               5
```

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

```
Tyr Pro Tyr Asp Val Pro Asp Tyr Ala
1               5
```

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

```
Met Ala Ser Met Thr Gly Gly Gln Gln Met Gly
1               5                   10
```

<210> SEQ ID NO 14
<211> LENGTH: 35
<212> TYPE: PRT
<213> ORGANISM: Artificial Sequence
<220> FEATURE:
<223> OTHER INFORMATION: Synthetic

<400> SEQUENCE: 14

```
Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
            20                  25                  30

Ala Ala Ala
        35
```

<210> SEQ ID NO 15
<211> LENGTH: 105
<212> TYPE: DNA
<213> ORGANISM: Artificial Sequence
<220> FEATURE:
<223> OTHER INFORMATION: Synthetic

<400> SEQUENCE: 15

```
tctggtcctg gaggttatgg cccaggaagc caaggaccat ctggtccagg aggatatggt    60
ccaggcggac ctggctctag tgcagcagct gccgcagcag ctgca                  105
```

```
<210> SEQ ID NO 16
<211> LENGTH: 28
<212> TYPE: DNA
<213> ORGANISM: Artificial Sequence
<220> FEATURE:
<223> OTHER INFORMATION: Synthetic

<400> SEQUENCE: 16
atatgctgca ggccctagtg gtcctgga                                          28

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
tcgacaagct tggtaccgca                                                   20
```